United States Patent
Nakagawa et al.

(10) Patent No.: US 7,622,270 B2
(45) Date of Patent: Nov. 24, 2009

(54) METHODS OF ISOLATING DOPAMINERGIC NEURON PRECURSOR CELLS

(75) Inventors: Yasuko Nakagawa, Kyoto (JP); Yuichi Ono, Kyoto (JP); Yoshimasa Sakamoto, Kyoto (JP); Eri Mizuhara, Kyoto (JP); Tomoya Nakatani, Kyoto (JP); Yoshimi Takai, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 319 days.

(21) Appl. No.: 10/532,264

(22) PCT Filed: Oct. 21, 2003

(86) PCT No.: PCT/JP03/13420

§ 371 (c)(1),
(2), (4) Date: Dec. 28, 2005

(87) PCT Pub. No.: WO2004/038018

PCT Pub. Date: May 6, 2004

(65) Prior Publication Data

US 2006/0239978 A1    Oct. 26, 2006

(30) Foreign Application Priority Data

Oct. 22, 2002    (JP)    ............... 2002-307573

(51) Int. Cl.
*G01N 33/567*    (2006.01)
*C07K 16/28*    (2006.01)
(52) U.S. Cl. .................................. 435/7.21; 530/387.9
(58) Field of Classification Search ....................... None
See application file for complete search history.

(56) References Cited

U.S. PATENT DOCUMENTS

| 7,304,145 B2 | 12/2007 | Goddard et al. |
| 2002/0068045 A1 | 6/2002 | Reubinoff et al. |
| 2002/0127584 A1 | 9/2002 | Baker et al. |
| 2002/0155423 A1 | 10/2002 | Okano et al. |
| 2003/0036150 A1 | 2/2003 | Baker et al. |
| 2003/0109039 A1* | 6/2003 | Buck et al. .................. 435/368 |
| 2004/0241170 A1* | 12/2004 | Jensen et al. ............. 424/178.1 |
| 2007/0254281 A1 | 11/2007 | Ono et al. |

FOREIGN PATENT DOCUMENTS

| CA | 2 315 538 A1 | 7/1999 |
| JP | 2001-526884 A | 12/2001 |
| WO | WO 94/23754 A1 | 10/1994 |
| WO | WO 01/92482 A1 | 12/2001 |
| WO | WO 01/98360 A2 | 12/2001 |
| WO | WO 01/98360 A3 | 12/2001 |
| WO | WO 2004/065599 A1 | 8/2004 |

OTHER PUBLICATIONS

Sun (2003) Genomics 82(2):130-142.*
Genbank Accession No. AF296764, "Mus musculus nephrin (Nphs1) gene, 5' flanking region, 5' UTR.", Aug. 16, 2000.
Genbank Accession No. AC002133, "Human DNA from chromosome 19 cosmid R33502, genomic sequence.", Jun. 3, 1997.
Genbank Accession No. BCO52773, "Mus musculus kin of IRRE like 2 (Drosophila), mRNA (cDNA clone MGC:56936 Image:6314924)", May 23, 2003.
Björklund, Lars M. et al.; "Embryonic stem cells develop into functional dopaminergic neurons after transplantation in a Parkinson rat model"; *PNAS;* Feb. 19, 2002; pp. 2344-2349; vol. 99, No. 4.
Björklund, Anders et al.; "Neural transplantation for the treatment of Parkinson's disease"; *The Lancet: Neurology;* Jul. 2003; pp. 437-445; vol. 2.
Kim, Tai Eun et al.; "Cloning and cell type-specific regulation of the human tyrosine hydroxylase gene promoter"; *Biochemical and Biophysical Research Communications;* 2003; pp. 1123-1131; vol. 312.
Yan, Jun et al.; "Ascorbic acid increases the yield of dopaminergic neurons derived from basic fibroblast growth factor expanded mesencephalic precursors"; *Journal of Neurochemistry;* 2001; pp. 307-311; vol. 76.
Alberts, B., et al., *Molecular Biology of the Cell,* pp. 104-111, Third Edition (1994).
Huber, Tobias B. et al.; "The carboxyl terminus of Neph family members binds to teh PDZ domain protin zolula occludens-1"; *The Journal of Biological Chemistry;* Apr. 11, 2003; pp. 13417-13421; vol. 278, No. 15.
Ihalmo, Pekka et al.; "Filtrin is a novel member of nephrin-like proteins"; *Biochemical and Biophysical Research Communications;* 2003; pp. 364-370; vol. 300.
Kawasaki, Hiroshi et al.; "Induction of midbrain dopaminergic neurons from ES cells by stromal cell-derived inducing activity"; *Neuron;* Oct. 2000; pp. 31-40; vol. 28.
Kim, Jong-Hoon et al.; "Dopamine neurons derived from embryonic stem cells function in an animal model of Parkinson's disease"; *Nature;* Jul. 4, 2002; pp. 50-56; vol. 418.
Kordower, J. H. et al.; "Neuropathological evidence of graft survival and striatal reinnervation after the transplantation of fetal mesencephalic tissue in a patient with Parkinson's disease"; *N. Engl. J. Med.;* Apr. 27, 1995; pp. 1118-1124; vol. 332, No. 17.
Lisitsyn, N. A.; "Representational difference analysis: finding the differences between genomes"; *Trends Genet.;* Aug. 1995; pp. 303-307; vol. 11, No. 8.

(Continued)

*Primary Examiner*—Daniel E. Kolker
(74) *Attorney, Agent, or Firm*—Townsend and Townsend and Crew LLP

(57) ABSTRACT

A novel gene 65B13 expressed specifically and transiently in dopaminergic neuron precursor cells immediately after cell cycle exit was obtained by the present invention. The cellular expression of 65B13 can be used as an index to select cells that are suitable in terms of their safety, survival rate, and network formation ability, for transplant therapy of neurodegenerative diseases such as Parkinson's disease.

10 Claims, 14 Drawing Sheets

OTHER PUBLICATIONS

Sakurada, Kazuhiro et al.; "Seitai Shinkei Kansaibo Bunka no Bunshi Mechanism"; *Cell Technology;* 2000; pp. 398-405; vol. 19, No. 3 (In Japanese).

Sakurada, Kazuhiro et al.; "Seitai Shinkei Kansaibo o Hyoteki to shita Saisei Iryo"; *The Tissue Culture Engineering;* 2000; pp. 303-306; vol. 26, No. 8 (In Japanese).

Sawamoto, Kazunobu et al.; "Generation of dopaminergic neurons in the adult brain from mesencephalic precursor cells labeled with *nestin-GFP* transgene"; *The Journal of Neuroscience;* Jun. 1, 2001; pp. 3895-3903; vol. 21, No. 11.

Sawamoto, Kazunobu et al.; "Visualization, direct isolation, and transplantation of midbrain dopaminergic neurons"; *PNAS;* May 22, 2001; pp. 6423-6428; vol. 98, No. 11.

Sellin, Lorenz etal.; "NEPH1 defines a novel family of podocin interacting proteins"; *FASEB J.;* Jan. 2003; pp. 115-117; vol. 17.

Studer, Lorenz et al.; "Transplantation of expanded mesencephalic precursors leads to recovery in parkinsonian rats"; *Nature Neuroscience;* Aug. 1998; pp. 290-295; vol. 1, No. 4.

Di Porzio, et al., "Dopaminergic neurons from embryonic mouse mesencephalon are enriched in culture through immunoreaction with monoclonal antibody to neural specific protein 4 and flow cytometry," *Proc Natl Acad Sci U.S.A.,* 1987, vol. 84, No. 20, pp. 7334-8.

Shinmura, Comprehensive Dictionary of the Japanese Language (Kojien), 1998, 5th Ed. pp. 1466.

\* cited by examiner

FIG. 1

| | | | | | | | | | | | | | | | | | |
|---|---|---|---|---|---|---|---|---|---|---|---|---|---|---|---|---|---|
|GAT|GAG|CCA|GAT|TTC|GGG|GAC|TCT|GGG|CCA|GAC|ATA|AAA|TCT|TCC|AGC|CCG|GAG|54|
|AGA|ATT|GTG|TGC|AGA|GAG|GGG|CTC|CAG|TCC|AGC|GTG|GTG|TGA|GAG|GCG|TGC|TAT|108|
|CAA|GAA|AGA|AGT|TGG|AGG|GGA|ACC|AGT|GCA|ACC|CTA|ACT|CTA|CGA|GAT|CTT|GGG|162|
|GTA|CAC|ACA|CTC|GGG|ATG|CTG|GCC|TCC|GCC|CTC|CTC|GTT|TTC|CTT|TGC|TGT|TTC|216|
| | | | | |M|L|A|S|A|L|L|V|F|L|C|C|F| |
|AAA|GGA|CAT|GCA|GGC|TCA|TCG|CCC|CAT|TTC|CTA|CAA|CAG|CCA|GAG|GAC|ATG|GTG|270|
|K|G|H|A|G|S|S|P|H|F|L|Q|Q|P|E|D|M|V| |
|GTG|CTG|TTG|GGG|GAG|GAA|GCC|CGG|CTG|CCC|TGC|GCT|CTG|GGC|GCG|TAC|AGG|GGG|324|
|V|L|L|G|E|E|A|R|L|P|C|A|L|G|A|Y|R|G| |
|CTC|GTG|CAG|TGG|ACT|AAG|GAT|GGG|CTG|GCT|CTA|GGG|GGC|GAA|AGA|GAC|CTT|CCA|378|
|L|V|Q|W|T|K|D|G|L|A|L|G|G|E|R|D|L|P| |
|GGG|TGG|TCC|CGG|TAC|TGG|ATA|TCG|GGG|AAT|TCA|GCC|AGT|GGC|CAG|CAT|GAC|CTC|432|
|G|W|S|R|Y|W|I|S|G|N|S|A|S|G|Q|H|D|L| |
|CAC|ATT|AAG|CCT|GTG|GAA|TTG|GAA|GAT|GAG|GCA|TCG|TAT|GAG|TGC|CAG|GCT|TCG|486|
|H|I|K|P|V|E|L|E|D|E|A|S|Y|E|C|Q|A|S| |
|CAA|GCA|GGT|CTC|CGA|TCA|CGA|CCA|GCC|CAA|CTG|CAC|GTG|ATG|GTC|CCC|CCA|GAA|540|
|Q|A|G|L|R|S|R|P|A|Q|L|H|V|M|V|P|P|E| |
|GCT|CCC|CAG|GTA|CTA|GGC|GGC|CCC|TCT|GTG|TCT|CTG|GTT|GCT|GGA|GTT|CCT|GGA|594|
|A|P|Q|V|L|G|G|P|S|V|S|L|V|A|G|V|P|G| |
|AAT|CTG|ACC|TGT|CGG|AGT|CGT|GGG|GAT|TCC|CGA|CCT|GCC|CCT|GAA|CTA|CTG|TGG|648|
|N|L|T|C|R|S|R|G|D|S|R|P|A|P|E|L|L|W| |
|TTC|CGA|GAT|GGG|ATC|CGG|CTG|GAT|GCG|AGC|AGC|TTC|CAC|CAG|ACC|ACG|CTG|AAG|702|
|F|R|D|G|I|R|L|D|A|S|S|F|H|Q|T|T|L|K| |
|GAC|AAG|GCC|ACT|GGA|ACA|GTG|GAA|AAC|ACC|TTA|TTC|CTG|ACC|CCT|TCC|AGT|CAT|756|
|D|K|A|T|G|T|V|E|N|T|L|F|L|T|P|S|S|H| |
|GAT|GAT|GGC|GCC|ACC|TTG|ATC|TGC|AGA|GCG|CGA|AGC|CAG|GCC|CTG|CCC|ACA|GGG|810|
|D|D|G|A|T|L|I|C|R|A|R|S|Q|A|L|P|T|G| |
|AGG|GAC|ACA|GCT|GTT|ACA|CTG|AGC|CTT|CAG|TAT|CCC|CCA|ATG|GTG|ACT|CTG|TCT|864|
|R|D|T|A|V|T|L|S|L|Q|Y|P|P|M|V|T|L|S| |
|GCT|GAG|CCC|CAG|ACT|GTG|CAG|GAG|GGA|GAG|AAG|GTG|ACT|TTC|CTG|TGT|CAA|GCC|918|
|A|E|P|Q|T|V|Q|E|G|E|K|V|T|F|L|C|Q|A| |
|ACT|GCC|CAG|CCT|CCT|GTC|ACT|GGC|TAC|AGG|TGG|GCG|AAG|GGG|GGA|TCC|CCG|GTG|972|
|T|A|Q|P|P|V|T|G|Y|R|W|A|K|G|G|S|P|V| |
|CTC|GGG|GCA|CGT|GGG|CCA|AGG|TTG|GAG|GTC|GTT|GCA|GAT|GCC|ACT|TTC|CTG|ACT|1026|
|L|G|A|R|G|P|R|L|E|V|V|A|D|A|T|F|L|T| |
|GAG|CCG|GTG|TCC|TGC|GAG|GTC|AGC|AAC|GCG|GTC|GGA|AGC|GCC|AAC|CGC|AGC|ACG|1080|
|E|P|V|S|C|E|V|S|N|A|V|G|S|A|N|R|S|T| |
|GCG|CTG|GAA|GTG|TTG|TAT|GGA|CCC|ATT|CTG|CAG|GCA|AAA|CCT|AAG|TCC|GTG|TCC|1134|
|A|L|E|V|L|Y|G|P|I|L|Q|A|K|P|K|S|V|S| |
|GTG|GAC|GTG|GGG|AAA|GAT|GCC|TCC|TTC|AGC|TGT|GTC|TGG|CGC|GGG|AAC|CCA|CTT|1188|
|V|D|V|G|K|D|A|S|F|S|C|V|W|R|G|N|P|L| |
|CCA|CGG|ATA|ACC|TGG|ACC|CGC|ATG|GGT|GGC|TCT|CAG|GTG|CTG|AGC|TCC|GGG|CCC|1242|
|P|R|I|T|W|T|R|M|G|G|S|Q|V|L|S|S|G|P| |
|ACG|CTG|CGG|CTT|CCG|TCC|GTG|GCA|CTG|GAG|GAT|GCG|GGC|GAC|TAT|GTA|TGC|AGG|1296|
|T|L|R|L|P|S|V|A|L|E|D|A|G|D|Y|V|C|R| |
|GCT|GAG|CCG|AGG|AGA|ACG|GGT|CTG|GGA|GGC|GGC|AAA|GCG|CAG|GCG|AGG|CTG|ACT|1350|
|A|E|P|R|R|T|G|L|G|G|G|K|A|Q|A|R|L|T| |
|GTG|AAC|GCA|CCC|CCT|GTA|GTG|ACA|GCC|CTG|CAA|CCT|GCA|CCA|GCC|TTT|CTG|AGG|1404|
|V|N|A|P|P|V|V|T|A|L|Q|P|A|P|A|F|L|R| |

FIG. 2

```
GGT CCT GCT CGC CTC CAG TGT GTG GTG TTT GCC TCC CCT GCC CCA GAC TCG GTG  1458
 G   P   A   R   L   Q   C   V   V   F   A   S   P   A   P   D   S   V
GTT TGG TCT TGG GAC GAG GGC TTC TTG GAG GCA GGC TCA CTG GGC AGG TTC CTA  1512
 V   W   S   W   D   E   G   F   L   E   A   G   S   L   G   R   F   L
GTG GAA GCC TTC CCA GCC CCG GAA GTG GAG GGG GGA CAG GGC CCT GGC CTT ATT  1566
 V   E   A   F   P   A   P   E   V   E   G   G   Q   G   P   G   L   I
TCT GTG CTA CAC ATT TCC GGA ACC CAG GAG TCC GAC TTT ACC ACC GGC TTC AAC  1620
 S   V   L   H   I   S   G   T   Q   E   S   D   F   T   T   G   F   N
TGC AGT GCC CGC AAC CGG CTA GGA GAG GGA CGA GTC CAG ATC CAC TTG GGC CGT  1674
 C   S   A   R   N   R   L   G   E   G   R   V   Q   I   H   L   G   R
AGA GAT TTG CTG CCT ACT GTC CGG ATT GTG GCT GGT GCA GCA TCT GCA GCC ACC  1728
 R   D   L   L   P   T   V   R   I   V   A   G   A   A   S   A   A   T
TCT CTC CTT ATG GTC ATC ACT GGA GTG GTC CTC TGC TGC TGG CGC CAT GGC TCT  1782
 S   L   L   M   V   I   T   G   V   V   L   C   C   W   R   H   G   S
CTC TCT AAG CAA AAG AAC TTG GTC CGG ATC CCA GGA AGC AGC GAG GGT TCC AGT  1836
 L   S   K   Q   K   N   L   V   R   I   P   G   S   S   E   G   S   S
TCA CGT GGC CCT GAG GAG GAG ACA GGC AGC AGT GAG GAC CGG GGT CCC ATT GTG  1890
 S   R   G   P   E   E   E   T   G   S   S   E   D   R   G   P   I   V
CAC ACC GAC CAC AGT GAT TTG GTT CTT GAG GAA AAA GAG GCT CTG GAG ACA AAG  1944
 H   T   D   H   S   D   L   V   L   E   E   K   E   A   L   E   T   K
GAT CCA ACC AAC GGT TAC TAC AAG GTT CGA GGG GTC AGT GTG AGC CTT AGC CTT  1998
 D   P   T   N   G   Y   Y   K   V   R   G   V   S   V   S   L   S   L
GGG GAA GCT CCT GGA GGA GGC CTC TTC TTG CCA CCG CCC TCT CCG ATC GGT CTC  2052
 G   E   A   P   G   G   G   L   F   L   P   P   P   S   P   I   G   L
CCA GGG ACT CCT ACT TAC TAT GAC TTC AAG CCA CAT CTG GAC TTA GTC CCT CCC  2106
 P   G   T   P   T   Y   Y   D   F   K   P   H   L   D   L   V   P   P
TGC AGA CTG TAC AGA GCG AGG GCA GGT TAT CTT ACC ACC CCC CAT CCC CGT GCC  2160
 C   R   L   Y   R   A   R   A   G   Y   L   T   T   P   H   P   R   A
TTC ACC AGC TAC ATG AAA CCC ACA TCC TTT GGA CCC CCA GAT TTG AGC TCT GGA  2214
 F   T   S   Y   M   K   P   T   S   F   G   P   P   D   L   S   S   G
ACT CCC CCC TTC CCG TAT GCT ACC TTG TCT CCA CCC AGC CAC CAG CGT CTC CAG  2268
 T   P   P   F   P   Y   A   T   L   S   P   P   S   H   Q   R   L   Q
ACT CAT GTG TGA ATC CAT CTC TCC AAG TGA AGG GTC TTG GAA TCT TCT GTT TGC  2322
 T   H   V   *
CAT ATA GTG TGT TGT CCA GAT TTC TGG GGA GTC AGA ACA AGT TGA TGA CCA ACC  2376
CCT CCA AAA CTG AAC ATT GAA GGA GGG AAA GAT CAT TAC AAG CAT CAG GAC TGT  2430
TGG TGT ACA CTC AGT TCA GCC AAA GTG GAT TCT CCA AGT GGG AGC AAT ATG GCC  2484
GCT TTC CCA TGA GAA AGA CAT TCA AGA TGG TGA CTA AAT GAC TAA ATA CTT TGC  2538
AGA GGG ACA AAG ATG GGA ACT AGG GAT ACG GAT GGA AGT AGT AGA GAA GAT ATA  2592
TGA CCA TCT GCA TCA AGA GGA AGG ATA ACA TAT GAC AAA TCA AGA TGA AAG AAA  2646
TAA TCC ACC CCA CCC CCA CCG CGT CCT GGC CAA TAA GTA TAG CCT ACA TGG CTG  2700
TTC ATT ATC TGG GAA CCA AAA TGG CCA CTA TCT TGA CTC CTT CCT TAA AGA TAC  2754
AGA AAG AAT TGA ATC CAA GGA ATG GGG TAG GGT GGA AAT AGA AGA AAT GAA GGG  2808
GAC TCT TGG GCT AAG AAT ACT TAT GTT TAA TAA TAA AAG GGG GAG GCA AAG ATG  2862
CAA AAA AAA AAA AAA AA                                                   2876
```

FIG. 3

```
GAG AGA ATT GTG TGC AGA GAG AGG CTC CAG TCC AGC GTG GTG TGA GAG GCG TGC    54
TAT CAA GAA AGA AGT TGG AGG GGA ACC AGT GCA ACC CTA ACT CTA CGA GAT CTT   108
GGG GTA CAC ACA CTC GGG ATG CTG GCC TCC GCC CTC CTC GTT TTC CTT TGC TGT   162
                         M   L   A   S   A   L   L   V   F   L   C   C
TTC AAA GGA CAT GCA GGG TGG TCC CGG TAC TGG ATA TCG GGG AAT TCA GCC AGT   216
 F   K   G   H   A   G   W   S   R   Y   W   I   S   G   N   S   A   S
GGC CAG CAT GAC CTC CAC ATT AAG CCT GTG GAA TTG GAA GAT GAG GCA TCG TAT   270
 G   Q   H   D   L   H   I   K   P   V   E   L   E   D   E   A   S   Y
GAG TGC CAG GCT TCG CAA GCA GGT CTC CGA TCA CGA CCA GCC AAC TGC ACG TG    324
 E   C   Q   A   S   Q   A   G   L   R   S   R   P   A   Q   L   H   V
ATG GTC CCC CCA GAA GCT CCC CAG GTA CTA GGC GGC CCC TCT GTG TCT CTG GTT   378
 M   V   P   P   E   A   P   Q   V   L   G   G   P   S   V   S   L   V
GCT GGA GTT CCT GGA AAT CTG ACC TGT CGG AGT CGT GGG GAT TCC CGA CCT GCC   432
 A   G   V   P   G   N   L   T   C   R   S   R   G   D   S   R   P   A
CCT GAA CTA CTG TGG TTC CGA GAT GGG ATC CGG CTG GAT GCG AGC AGC TTC CAC   486
 P   E   L   L   W   F   R   D   G   I   R   L   D   A   S   S   F   H
CAG ACC ACG CTG AAG GAC AAG GCC ACT GGA ACA GTG GAA AAC ACC TTA TTC CTG   540
 Q   T   T   L   K   D   K   A   T   G   T   V   E   N   T   L   F   L
ACC CCT TCC AGT CAT GAT GAT GGC GCC ACC TTG ATC TGC AGA GCG CGA AGC CAG   594
 T   P   S   S   H   D   D   G   A   T   L   I   C   R   A   R   S   Q
GCC CTG CCC ACA GGG AGG GAC ACA GCT GTT ACA CTG AGC CTT CAG TAT CCC CCA   648
 A   L   P   T   G   R   D   T   A   V   T   L   S   L   Q   Y   P   P
ATG GTG ACT CTG TCT GCT GAG CCC CAG ACT GTG CAG GAG GGA GAG AAG GTG ACT   702
 M   V   T   L   S   A   E   P   Q   T   V   Q   E   G   E   K   V   T
TTC CTG TGT CAA GCC ACT GCC CAG CCT CCT GTC ACT GGC TAC AGG TGG GCG AAG   756
 F   L   C   Q   A   T   A   Q   P   P   V   T   G   Y   R   W   A   K
GGG GGA TCC CCG GTG CTC GGG GCA CGT GGG CCA AGG TTG GAG GTC GTT GCA GAT   810
 G   G   S   P   V   L   G   A   R   G   P   R   L   E   V   V   A   D
GCC ACT TTC CTG ACT GAG CCG GTG TCC TGC GAG GTC AGC AAC GCG GTC GGA AGC   864
 A   T   F   L   T   E   P   V   S   C   E   V   S   N   A   V   G   S
GCC AAC CGC AGC ACG GCG CTG GAA GTG TTG TAT GGA CCC ATT CTG CAG GCA AAA   918
 A   N   R   S   T   A   L   E   V   L   Y   G   P   I   L   Q   A   K
CCT AAG TCC GTG TCC GTG GAC GTG GGG AAA GAT GCC TCC TTC AGC TGT GTC TGG   972
 P   K   S   V   S   V   D   V   G   K   D   A   S   F   S   C   V   W
CGC GGG AAC CCA CTT CCA CGG ATA ACC TGG ACC CGC ATG GGT GGC TCT CAG GTG  1026
 R   G   N   P   L   P   R   I   T   W   T   R   M   G   G   S   Q   V
CTG AGC TCC GGG CCC ACG CTG CGG CTT CCG TCC GTG GCA CTG GAG GAT GCG GGC  1080
 L   S   S   G   P   T   L   R   L   P   S   V   A   L   E   D   A   G
GAC TAT GTA TGC AGG GCT GAG CCG AGG AGA ACG GGT CTG GGA GGC GGC AAA GCG  1134
 D   Y   V   C   R   A   E   P   R   R   T   G   L   G   G   G   K   A
CAG GCG AGG CTG ACT GTG AAC GCA CCC CCT GTA GTG ACA GCC CTG CAA CCT GCA  1188
 Q   A   R   L   T   V   N   A   P   P   V   V   T   A   L   Q   P   A
```

FIG. 4

```
CCA GCC TTT CTG AGG GGT CCT GCT CGC CTC CAG TGT GTG GTG TTT GCC TCC CCT   1242
 P   A   F   L   R   G   P   A   R   L   Q   C   V   V   F   A   S   P
GCC CCA GAC TCG GTG GTT TGG TCT TGG GAC GAG GGC TTC TTG GAG GCA GGC TCA   1296
 A   P   D   S   V   V   W   S   W   D   E   G   F   L   E   A   G   S
CTG GGC AGG TTC CTA GTG GAA GCC TTC CCA GCC CCG GAA GTG GAG GGG GGA CAG   1350
 L   G   R   F   L   V   E   A   F   P   A   P   E   V   E   G   G   Q
GGC CCT GGC CTT ATT TCT GTG CTA CAC ATT TCC GGA ACC CAG GAG TCC GAC TTT   1404
 G   P   G   L   I   S   V   L   H   I   S   G   T   Q   E   S   D   F
ACC ACC GGC TTC AAC TGC AGT GCC CGC AAC CGG CTA GGA GAG GGA CGA GTC CAG   1458
 T   T   G   F   N   C   S   A   R   N   R   L   G   E   G   R   V   Q
ATC CAC TTG GGC CGT AGA GAT TTG CTG CCT ACT GTC CGG ATT GTG GCT GGT GCA   1512
 I   H   L   G   R   R   D   L   L   P   T   V   R   I   V   A   G   A
GCA TCT GCA GCC ACC TCT CTC CTT ATG GTC ATC ACT GGA GTG GTC CTC TGC TGC   1566
 A   S   A   A   T   S   L   L   M   V   I   T   G   V   V   L   C   C
TGG CGC CAT GGC TCT CTC TCT AAG CAA AAG AAC TTG GTC CGG ATC CCA GGA AGC   1620
 W   R   H   G   S   L   S   K   Q   K   N   L   V   R   I   P   G   S
AGC GAG GGT TCC AGT TCA CGT GGC CCT GAG GAG GAG ACA GGC AGC AGT GAG GAC   1674
 S   E   G   S   S   S   R   G   P   E   E   E   T   G   S   S   E   D
CGG GGT CCC ATT GTG CAC ACC GAC CAC AGT GAT TTG GTT CTT GAG GAA AAA GAG   1728
 R   G   P   I   V   H   T   D   H   S   D   L   V   L   E   E   K   E
GCT CTG GAG ACA AAG GAT CCA ACC AAC GGT TAC TAC AAG GTT CGA GGG GTC AGT   1782
 A   L   E   T   K   D   P   T   N   G   Y   Y   K   V   R   G   V   S
GTG AGC CTT AGC CTT GGG GAA GCT CCT GGA GGA GGC CTC TTC TTG CCA CCG CCC   1836
 V   S   L   S   L   G   E   A   P   G   G   G   L   F   L   P   P   P
TCT CCG ATC GGT CTC CCA GGG ACT CCT ACT TAC TAT GAC TTC AAG CCA CAT CAG   1890
 S   P   I   G   L   P   G   T   P   T   Y   Y   D   F   K   P   H   Q
GAC TTA GTC CCT CCC TGC AGA CTG TAC AGA GCG AGG GCA GGT TAT CTT ACC ACC   1944
 D   L   V   P   P   C   R   L   Y   R   A   R   A   G   Y   L   T   T
CCC CAT CCC CGT GCC TTC ACC AGC TAC ATG AAA CCC ACA TCC TTT GGA CCC CCA   1998
 P   H   P   R   A   F   T   S   Y   M   K   P   T   S   F   G   P   P
GAT TTG AGC TCT GGA ACT CCC CCC TTC CCG TAT GCT ACC TTG TCT CCA CCC AGC   2052
 D   L   S   S   G   T   P   P   F   P   Y   A   T   L   S   P   P   S
CAC CAG CGT CTC CAG ACT CAT GTG TGA ATC CAT CTC TCC AAG TGA AGG GTC TTG   2106
 H   Q   R   L   Q   T   H   V   *
GAA TCT TCT GTT TGC CAT ATA GTG TGT TGT CCA GAT TTC TGG GGA GTC AGA ACA   2160
AGT TGA TGA CCA ACC CCT CCA AAA CTG AAC ATT GAA GGA GGG AAA GAT CAT TAC   2214
AAG CAT CAG GAC TGT TGG TGT ACA CTC AG                                    2241
```

FIG. 5

```
              10         20         30         40         50
65B13-a   1  MLASALLVFL CCFKGHAGSS PHFLQQPEDM VVLLGEEARL PCALGAYRGL  50
65B13-b   1  MLASALLVFL CCFKGHAG-- ---------- ---------- ----------  50
              60         70         80         90        100
65B13-a  51  VQWTKDGLAL GGERDLPGWS RYWISGNSAS GQHDLHIKPV ELEDEASYEC 100
65B13-b  51  ---------- --------WS RYWISGNSAS GQHDLHIKPV ELEDEASYEC 100
             110        120        130        140        150
65B13-a 101  QASQAGLRSP PAQLHVMVPP EAPQVLGGPS VSLVAGVPGN LTCRSRGDSP 150
65B13-b 101  QASQAGLRSP PAQLHVMVPP EAPQVLGGPS VSLVAGVPGN LTCRSRGDSP 150
             160        170        180        190        200
65B13-a 151  PAPELLWFRL GIRLDASSFI QTTLKDKATC PVENTLFLTP SSHDDGATLI 200
65B13-b 151  PAPELLWFRL GIRLDASSFI QTTLKDKATC PVENTLFLTP SSHDDGATLI 200
             210        220        230        240        250
65B13-a 201  CRARSQALPT GRDTAVTLSL QYPPMVTLSA EPQTVQFGEK VTFLCQATAC 250
65B13-b 201  CRARSQALPT GRDTAVTLSL QYPPMVTLSA EPQTVQFGEK VTFLCQATAC 250
             260        270        280        290        300
65B13-a 251  PPVTGYRWAK GGSPVLGARG PRLEVVADAT FLTEPVSCEV SNAVGSANRS 300
65B13-b 251  PPVTGYRWAK GGSPVLGARG PRLEVVADAT FLTEPVSCEV SNAVGSANRS 300
             310        320        330        340        350
65B13-a 301  TALEVLYGPI LQAKPKSVSV DVGKDASFSC VWRGNPLPRI TWTRMGGSQV 350
65B13-b 301  TALEVLYGPI LQAKPKSVSV DVGKDASFSC VWRGNPLPRI TWTRMGGSQV 350
             360        370        380        390        400
65B13-a 351  LSSGPTLRLH SVALEDAGDY VCRAEPRRTG LGGKAQARI TVNAPPVVTA 400
65B13-b 351  LSSGPTLRLH SVALEDAGDY VCRAEPRRTG LGGKAQARI TVNAPPVVTA 400
             410        420        430        440        450
65B13-a 401  LQPAPAFLRC PARLQCVVFA SPAPDSVVWS WDEGFLEAGS LGRFLVEAFP 450
65B13-b 401  LQPAPAFLRC PARLQCVVFA SPAPDSVVWS WDEGFLEAGS LGRFLVEAFP 450
             460        470        480        490        500
65B13-a 451  APEVEGGQGI GLISVLHISE TQESDFTTGI NCSARNRLGE GRVQIHLGRP 500
65B13-b 451  APEVEGGQGI GLISVLHISE TQESDFTTGI NCSARNRLGE GRVQIHLGRP 500
             510        520        530        540        550
65B13-a 501  DLLPTVRIVA GAASAATSLL MVITGVVLCC WRIGSLSKQF NLVRIPGSSE 550
65B13-b 501  DLLPTVRIVA GAASAATSLL MVITGVVLCC WRIGSLSKQF NLVRIPGSSE 550
             560        570        580        590        600
65B13-a 551  GSSSRGPEEF TGSSEDRGPI VHTDHSDLVL EEKFALETKL PTNGYYKVRC 600
65B13-b 551  GSSSRGPEEF TGSSEDRGPI VHTDHSDLVL EEKFALETKL PTNGYYKVRC 600
             610        620        630        640        650
65B13-a 601  VSVSLSLGFA PGGGIFLPPP SPIGLPGTPT YYDFKPHLDL VPPCRLYRAR 650
65B13-b 601  VSVSLSLGFA PGGGIFLPPP SPIGLPGTPT YYDFKPHQDL VPPCRLYRAR 650
             660        670        680        690        700
65B13-a 651  AGYLTTPHPF AFTSYMKPTS FGPPDLSSGI PPFPYATLSP PSHQRLQTHV 700
65B13-b 651  AGYLTTPHPF AFTSYMKPTS FGPPDLSSGI PPFPYATLSP PSHQRLQTHV 700
```

FIG. 9
A
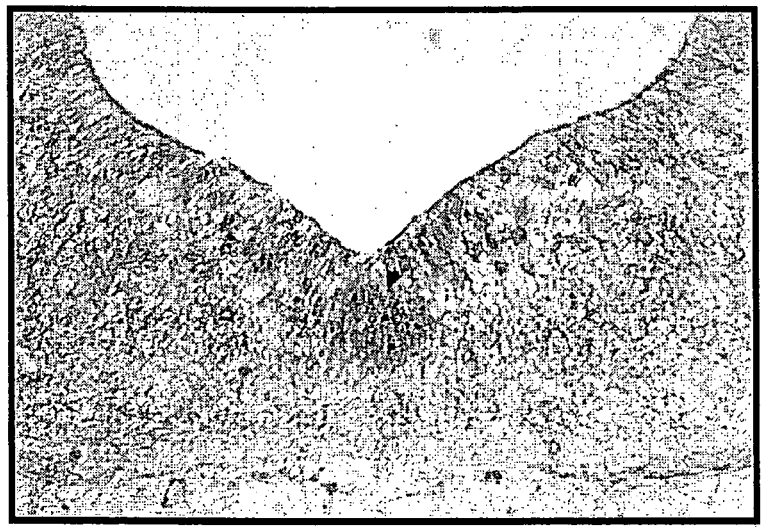
B

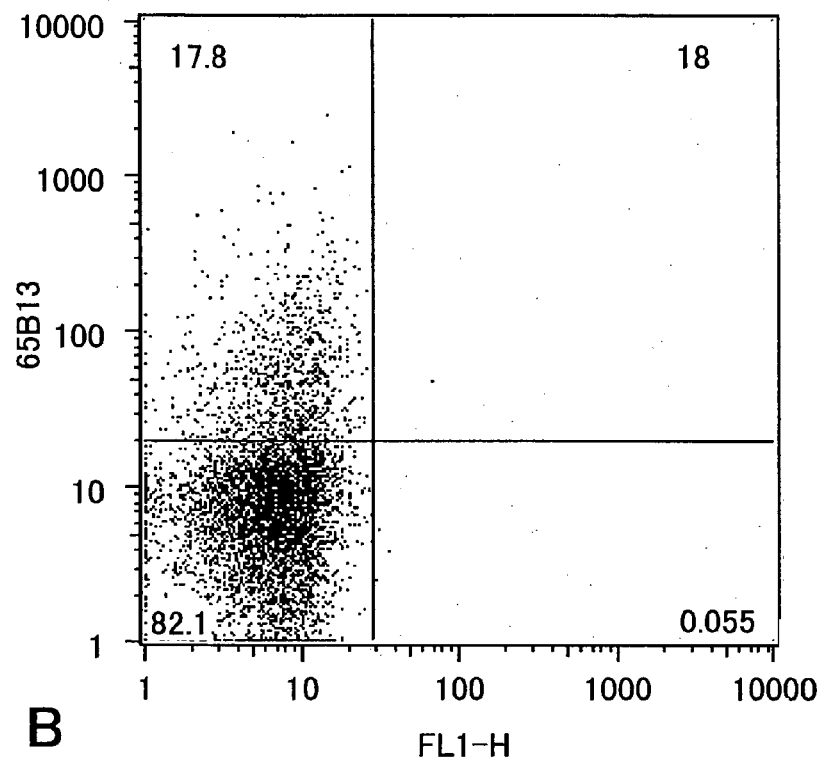
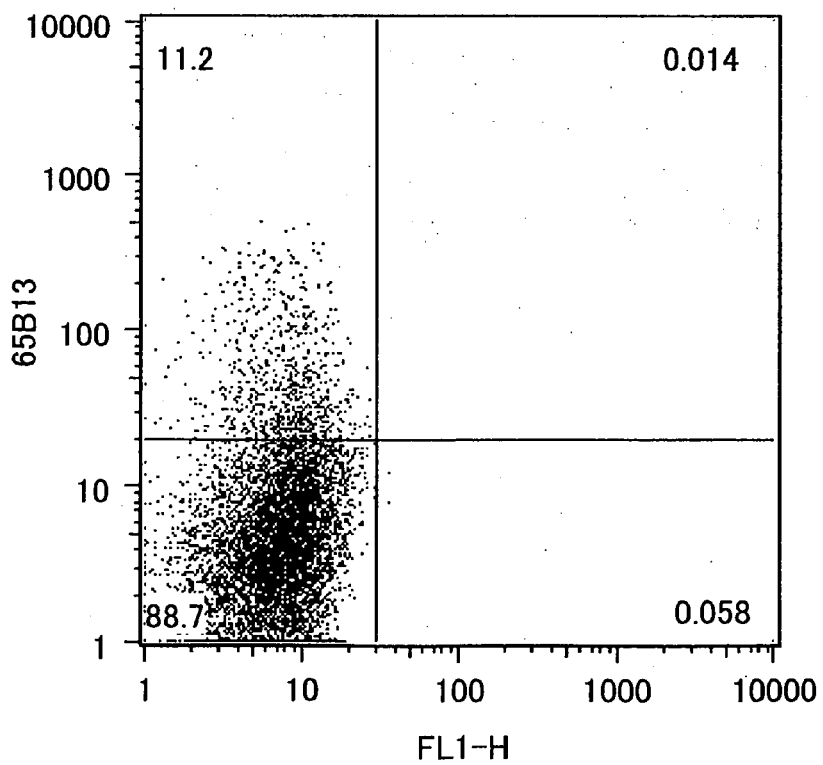
FIG. 14

METHODS OF ISOLATING DOPAMINERGIC NEURON PRECURSOR CELLS

TECHNICAL FIELD

The present invention relates to the novel 65B13 gene expressed in postmitotic dopaminergic neurons. Dopaminergic neuron precursor cells used in transplant therapy for neurodegenerative diseases such as Parkinson's disease (PD) can be efficiently isolated by detecting this gene.

BACKGROUND ART

The dopamine system is an extremely important system for essential motor regulation, hormone secretion regulation, emotion regulation, and such in the mammalian brain. Thus, abnormalities in dopaminergic neural transmission cause various neural disorders. For example, Parkinson's disease (PD) is a neurodegenerative disease of the extrapyramidal system that occurs due to specific degeneration of dopaminergic neurons in the substantia nigra of the midbrain (Harrison's Principles of Internal Medicine, Vol. 2, 23rd edition, Isselbacher et al., ed., McGraw-Hill Inc., NY (1994), pp. 2275-7). Oral administration of L-DOPA (3,4-dihydroxyphenylalanine) is performed as a primary therapeutic method to compensate for the decrease in the amount of dopamine produced; however, the duration of the effect is known to be unsatisfactory.

More recently, a therapeutic method in which the midbrain ventral zone of 6 to 9-week old aborted fetuses containing dopaminergic neuron progenitor cells are transplanted to compensate for the loss of dopaminergic neurons was attempted (U.S. Pat. No. 5,690,927; Spencer et al. (1992) N. Engl. J. Med. 327: 1541-8; Freed et al. (1992) N. Engl. J. Med. 327: 1549-55; Widner et al. (1992) N. Engl. J. Med. 327: 1556-63; Kordower et al. (1995) N. Engl. J. Med. 332: 1118-24; Defer et al. (1996) Brain 119: 41-50; Lopez-Lozano et al. (1997) Transp. Proc. 29: 977-80). However, in addition to cell supply and ethical issues (Rosenstain (1995) Exp. Neurol. 33: 106; Turner et al. (1993) Neurosurg. 33: 1031-7), this method is currently under criticism for various other problems, including risk of infection and contamination, immunological rejection of transplants (Lopez-Lozano et al. (1997) Transp. Proc. 29: 977-980; Widner and Brudin (1988) Brain Res. Rev. 13: 287-324), and low survival rates due to fetal tissues' primary dependence on the lipid metabolism rather than glycolysis (Rosenstein (1995) Exp. Neurol. 33: 106).

In order to resolve the ethical issues and shortage of supply, methods have been proposed that use, for example, porcine cortex, stria, or midbrain cells (for example, Published Japanese Translation of International Publication No. Hei 10-508487, Published Japanese Translation of International Publication No. Hei 10-508488 or Published Japanese Translation of International Publication No. Hei 10-509034). In these methods, a complex procedure that involves the alteration of cell surface antigens (MHC class I antigens) is required. Therefore, the use of an in vitro differentiation system to generate dopaminergic neurons from non-neural cells such as embryonic stem (ES) cells and bone marrow interstitial cells instead of cells derived from aborted fetuses, is considered promising. The importance of regeneration therapy using ES cells or patient's own neural stem cells is likely to grow in the future. A method involving local immunosuppression by simultaneously transplanting Steroli's cells has been proposed as a method of eliminating transplant rejection (Published Japanese Translation of International Publication No. Hei 11-509170, Published Japanese Translation of International Publication No. Hei 11-501818, Selawry and Cameron (1993) Cell Transplant 2: 123-9). It is possible to obtain transplant cells from relatives that have matching MHCs, bone marrow from other individuals, bone marrow banks, or umbilical cord-blood banks. However, if it were possible to use the patient's own cells, the problem of rejection reactions can be overcome without any laborious procedures and trouble.

An additional problem is the possibility that neuron progenitor cells may differentiate into groups of heterogeneous cells. In treating Parkinson's disease, it is necessary to selectively transplant those catecholamine-containing neurons that produce dopamine. Examples of transplant cells that have been proposed in the past for use in the treatment of Parkinson's disease include striatum (Lindvall et al. (1989) Arch. Neurol. 46: 615-31; Widner et al. (1992) N. Engl. J. Med. 327: 1556-63), immortalized cell lines derived from human fetal neurons (Published Japanese Translation of International Publication No. Hei 8-509215; Published Japanese Translation of International Publication No. Hei 11-506930; Published Japanese Translation of International Publication No. 2002-522070), human postmitotic neurons derived from NT2Z cells (Published Japanese Translation of International Publication No. Hei 9-5050554), primordial neuron cells (Published Japanese Translation of International Publication No. Hei 11-509729), and cells and bone marrow stroma cells transfected with exogenous genes so as to produce catecholamines such as dopamines (Published Japanese Translation of International Publication No. 2002-504503; Published Japanese Translation of International Publication No. 2002-513545). However, none of these contain only the dopaminergic neurons or cells that differentiate into dopaminergic cells.

A method has been proposed for selectively concentrating and isolating dopaminergic neurons from undifferentiated cell populations. In this method, a reporter gene that expresses a fluorescent protein is introduced into each cell of the cell population, under the control of a promoter/enhancer of genes, such as the tyrosine hydroxylase expressed in dopaminergic neurons, and then cells that emit fluorescence are isolated. The dopaminergic neurons are visualized in their viable state, and concentrated, isolated, and identified (Unexamined Published Japanese Patent Application No. 2002-51775). This method requires the step of introducing an exogenous gene, and further, the presence of a reporter gene poses problems of toxicity and immunogenicity for use in gene therapy.

DISCLOSURE OF THE INVENTION

One of the major problems in Parkinson's disease (PD) transplant therapy at the moment is that in vitro differentiated dopaminergic neuron precursor cells and midbrain ventral zone of aborted fetuses are both mixtures of myriad types of cells. When considering the safety in neural circuit formation, it is preferable to use isolated cells that comprise only the cell type of interest. Furthermore, when considering the risk of tumorigenesis, it is believed that it would be better to use isolated postmitotic neuron. Moreover, when considering the survival of cells at their transplant site in the brain, and their ability to properly form a network, it is expected that therapeutic effects can be further improved by isolating precursor cells at as early a stage as possible. Therefore, the inventors of the present invention aimed to isolate a gene specific to dopaminergic neuron precursor cells.

In order to isolate a gene specific to dopaminergic neuron precursor cells, genes with differential expressions were amplified by improving the subtraction method (N-RDA; representational differential analysis method; RDA method (Listsyn NA (1995) Trends Genet. 11: 303-7)), ("Method for Homogenizing the Amount of DNA Fragments and Subtraction Method", Japanese Patent Application No. 2001-184757 (filing date: Jun. 19, 2001)) using E12.5 mouse ventral and dorsal midbrain RNA, and analyzing the sequences of the amplified genes. As a result, the novel gene 65B13 was obtained. Two alternative isoforms, named 65B13-a and 65B13-b, were also obtained from determining the gene's full-length sequence by the RACE method. The nucleotide sequences of the isoforms are designated as SEQ ID NO: 1 and SEQ ID NO: 2. The amino acid sequences of proteins encoded by the nucleotide sequences are indicated as SEQ ID NO: 3 and SEQ ID NO: 4, respectively (FIGS. 1 to 4).

Based on the expression analysis results of these genes by in situ hybridization, and expression patterns obtained by comparison with those of the spinal cord growth marker Ki67 and the maturation marker NCAM, 65B13 was thought to be expressed transiently in neural precursor cells immediately after cell cycle exit. Moreover, 65B13 expression in the midbrain overlapped with that of tyrosine hydroxylase (TH), a marker gene of dopaminergic neurons, along the dorsal-ventral axial direction. Therefore, 65B13 is thought to be expressed specifically and transiently in dopaminergic neuron precursor cells immediately after cell cycle exit (FIGS. 10 and 11).

The in situ hybridization results were further supported by immunostaining using an anti-65B13 antibody (FIG. 13). Moreover, populations of cells expressing 65B13 could be efficiently separated by flow cytometry using an anti-65B13 antibody (FIG. 14).

According to the above results, anti-65B13 antibodies can be used to obtain pure early-stage dopaminergic neuron precursor cells, by isolating 65B13-expressing cells from ventral midbrain region or cell cultures that contain in vitro-differentiated dopaminergic neurons. Cells obtained in this manner contain only postmitotic precursor cells, and since only the cell type of interest is isolated, these cells are extremely safe even when used for transplant therapy. Since the earliest possible precursor cells are used, high therapeutic efficacy can be expected in terms of their survival rate, network formation ability, and such. Further, in the cases where the best therapeutic effects cannot be achieved by these early precursor cells obtained immediately after cell cycle exit, and where the use of matured cells is required, early precursor cells obtained by this method can simply be cultured in vitro to mature into a suitable stage of differentiation. Thus, materials that are in a differentiation stage suitable for the target transplant therapy can be easily prepared (FIG. 12).

Moreover, pure dopaminergic neuron precursor cells are also useful for the search of therapeutic targets for Parkinson's disease, isolation of genes specific for dopaminergic neurons precursor cells or stage-specific genes during the maturation of dopaminergic neuron precursor cells, and the like. In addition, the earliest possible precursor cells obtained using the methods of the present invention can also be used to unravel the maturation process of dopaminergic neurons, to screening systems using maturation as an indicator, and such.

More specifically, the present invention relates to:

[1] a polynucleotide that comprises a sequence selected from the nucleotide sequences of (1) to (5), wherein the nucleotide sequences encode 65B13 polypeptide expressed specifically in dopaminergic neuron precursor cells immediately after cell cycle exit, or antigenic fragment thereof:

(1) a nucleotide sequence that comprises the 177th to 2280th nucleotides of SEQ ID NO: 1 or the 127th to 2079th nucleotides of SEQ ID NO: 2, or sequence complementary to said nucleotide sequence;

(2) a nucleotide sequence that encodes the amino acid sequence of SEQ ID NO: 3 or 4, or sequence complementary to said nucleotide sequence;

(3) a nucleotide sequence that encodes the amino acid sequence of SEQ ID NO: 3 or 4, wherein a signal sequence portion is deleted, or sequence complementary to said nucleotide sequence;

(4) a nucleotide sequence that encodes the amino acid sequence of SEQ ID NO: 3 or 4, wherein one or more amino acids have been deleted, inserted, substituted, or added, or sequence complementary to said nucleotide sequence; and, (5) a nucleotide sequence that hybridizes with the nucleotide sequence (1) under stringent conditions;

[2] a vector that comprises the polynucleotide of [1];

[3] a host cell that comprises the polynucleotide of [1] or the vector of [2];

[4] a polypeptide that is encoded by the polynucleotide of [1];

[5] a fragment of the polypeptide of [4], wherein the polypeptide fragment comprises at least eight amino acid residues;

[6] an antibody against the polypeptide of [4] or the polypeptide fragment of [5];

[7] a nucleotide chain that encodes the polypeptide fragment of [5];

[8] a method for selecting a dopaminergic neuron, wherein the method comprises the step of contacting the antibody of [6] with a cell sample thought to comprise a dopaminergic neuron precursor cell;

[9] a method for selecting a dopaminergic neuron, wherein the method comprises the step of contacting a peptide comprising at least the extracellular portion of the polypeptide of [4] with a cell sample thought to comprise a dopaminergic neuron precursor cell;

[10] a Dopaminergic neuron precursor cell immediately after cell cycle exit, wherein the cell is selected by the method of [8] or [9];

[11] a method for isolating a gene specific to a dopaminergic neuron precursor cell, and a gene specific to each stage of maturation into a dopaminergic neurons, wherein the method comprises the step of: detecting and isolating a gene specifically expressed in the precursor cell of [10] or a cell differentiated, induced, or proliferated from said precursor cell; and

[12] a method for screening using maturation as an indicator, wherein the method comprises the steps of: contacting a test substance with the precursor cell of [10]; and detecting the differentiation or proliferation of the precursor cell resulting from the contacting step.

<Polynucleotides>

Polynucleotides of the present invention can be applied to generate antigens by genetic engineering techniques to produce antibodies that can be used for the selection of dopaminergic neuron precursor cells. A polynucleotide of the present invention encodes the 65B13 polypeptide specifically expressed in dopaminergic neuron precursor cells immediately after cell cycle exit, and comprises nucleotides 177 to 2280 of SEQ ID NO: 1 (FIGS. 1 and 2), nucleotides 127 to 2079 of SEQ ID NO: 2 (FIGS. 3 and 4), or a sequence complementary to either of these sequences.

Here, a "polynucleotide" refers to a polymer comprising nucleotides or nucleotide pairs of multiple deoxyribonucleic acids (DNA) or ribonucleic acids (RNA), and includes DNA, cDNA, genomic DNA, chemically synthesized DNA, and RNA. If needed, polynucleotides can also contain non-naturally-occurring nucleotides such as 4-acetylcytidine, 5-(carboxyhydroxymethyl)uridine, 2'-O-methylcytidine, 5-carboxymethylaminomethyl-2-thiouridine, 5-carboxyrethylaminomethyluridine, dihydrouridine, 2'-O-methylpseudouridine, β-D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueuosine, 5-methoxycarbonylmethyl-2-thiouridine, 5-methoxycarbonylmethyluridine, 5-methoxyuridine, 2-methylthio-N-6-isopentenyladenosine, N-((9-β-D-ribofuranosyl-2-methylthiopurin-6-yl)carbamoyl)threonine, N-((9-β-D-ribofuranosylpurin-6-yl)N-methylcarbamoyl) threonine, uridine-5-oxyacetic acid-methyl ester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-β-D-ribofuranosylpurin-6-yl)carbamoyl)threonine, 2'-O-methyl-5-methyluridine, 2'-O-methyluridine, wybutosine, and 3-(3-amino-3-carboxy propyl)uridine.

Moreover, a polynucleotide of the present invention encodes the 65B13 polypeptide specifically expressed in dopaminergic neuron precursor cells immediately after cell cycle exit, and comprises an amino acid sequence described in SEQ ID NO: 3 (FIGS. 1, 3 and 5) or SEQ ID NO: 4 (FIGS. 2, 4 and 5), or a complementary sequence thereof. In addition to the nucleotide sequences described in SEQ ID NOs: 1 and 2, nucleotide sequences encoding such an amino acid sequences include those that differ from the sequences described in SEQ ID NOs: 1 and 2 due to degeneracy of the genetic code. A polynucleotide of the present invention can be designed to express a polypeptide using genetic engineering techniques, by selecting a nucleotide sequence that has a high expression efficiency in view of the host's codon usage frequency (Grantham et al. (1981) Nucleic Acids Res. 9: 43-74). The polynucleotides of the present invention also comprise a nucleotide sequence encoding an amino acid sequence lacking the signal sequence portion of the amino acid sequence described in SEQ ID NO: 3 or 4. The first 17 amino acid residues of the amino acid sequence of SEQ ID NO: 3 or 4 correspond to a signal sequence.

The polynucleotides of the present invention also comprise a nucleotide sequence encoding the 65B13 polypeptide specifically expressed in dopaminergic neuron precursor cells immediately after cell cycle exit, or an antigenic fragment thereof, wherein one or more amino acids in the amino sequence of SEQ ID NO: 3 or 4 are deleted, inserted, substituted, or added, or a sequence complementary to this nucleotide sequence. It is well known that a mutant polypeptide comprising an amino acid sequence, in which one or more amino acids are deleted, inserted, substituted, or added, maintain the same biological activity as the original polypeptide (Mark et al. (1984) Proc. Natl. Acad. Sci. USA 81: 5662-6; Zoller and Smith (1982) Nucleic Acids Res. 10: 6487-500; Wang et al. (1984) Science 224: 1431-3; Dalbadie-McFarland et al. (1982) Proc. Natl. Acad. Sci. USA 79: 6409-13).

Here, an amino acid substitution refers to a mutation in which one or more amino acid residues in a sequence are changed to a different type of amino acid residue. When the amino acid sequence encoded by a polynucleotide of the present invention is altered by such a substitution, a conservative substitution is preferably carried out if the function of the protein is to be maintained. A conservative substitution means altering a sequence so that it encodes an amino acid that has properties similar to those of the amino acid before substitution. Amino acids can be classified, based on their properties, into non-polar amino acids (Ala, Ile, Leu, Met, Phe, Pro, Trp, Val), non-charged amino acids (Asn, Cys, Gln, Gly, Ser, Thr, Tyr), acidic amino acids (Asp, Glu), basic amino acids (Arg, His, Lys), neutral amino acids (Ala, Asn, Cys, Gln, Gly, Ile, Leu, Met, Phe, Pro, Ser, Thr, Trp, Tyr, Val), aliphatic amino acids (Ala, Gly), branched amino acids (Ile, Leu, Val), hydroxyamino acids (Ser, Thr), amide-type amino acids (Gln, Asn), sulfur-containing amino acids (Cys, Met), aromatic amino acids (His, Phe, Trp, Tyr), heterocyclic amino acids (His, Trp), imino acids (Pro, 4Hyp), and such. In particular, substitutions among Ala, Val, Leu, and Ile; Ser and Thr; Asp and Glu; Asn and Gln; Lys and Arg; and Phe and Tyr, are preferable in order to maintain protein properties. There are no particular limitations on the number and sites of the mutated amino acids, as long as the amino acid encoded by the polynucleotide has 65B13 antigenicity.

A polynucleotide encoding an amino acid sequence, in which one or more amino acids are deleted, inserted, substituted, or added to the sequence of SEQ ID NO: 3 or 4, can be prepared according to methods such as site-directed mutagenesis described in (Molecular Cloning, A Laboratory Manual $2^{nd}$ ed. (Cold Spring Harbor Press (1989)), Current Protocols in Molecular Biology (John Wiley & Sons (1987-1997); especially Section 8.1-8.5), Hashimoto-Goto et al. (1995) Gene 152: 271-5, Kunkel (1985) Proc. Natl. Acad. Sci. USA 82: 488-92, Kramer and Fritz (1987) Method. Enzymol. 154: 350-67, Kunkel (1988) Method. Enzymol. 85: 2763-6), and others.

Moreover, a polynucleotide of the present invention is a polynucleotide comprising a nucleotide sequence that hybridizes under stringent conditions with a nucleotide sequence comprising nucleotides 177 to 2280 of SEQ ID NO: 1 or nucleotides 127 to 2079 of SEQ ID NO: 2, or a sequence complementary to either of these sequences, wherein the polynucleotide encodes a 65B13 polypeptide specifically expressed in dopaminergic neuron precursor cells immediately after cell cycle exit, or an antigenic fragment thereof. In addition to the two 65B13 isoforms having sequences represented by SEQ ID NOs: 1 and 2 obtained in the Examples of the present invention, alternative isoforms and allelic mutations may also exist. Thus, such alternative isoforms and allelic mutations are also included in polypeptides of the present invention. Such polypeptides can be obtained from cDNA libraries or genomic libraries derived from animals such as humans, mice, rats, rabbits, hamsters, chickens, pigs, cows, goats, and sheep, by using a polynucleotide probe consisted of a nucleotide sequence comprising nucleotides 177 to 2280 of SEQ ID NO: 1 or nucleotides 127 to 2079 of SEQ ID NO: 2, in known hybridization methods such as colony hybridization, plaque hybridization, or Southern blotting. See "Molecular Cloning, A Laboratory Manual 2nd ed." (Cold Spring Harbor Press (1989)) for methods of cDNA library construction. In addition, a commercially available cDNA library or genomic library may also be used.

More specifically, in constructing a cDNA library, total RNA is first prepared from cells, organs, tissues, or such that express a polynucleotide of the present invention, by known techniques such as guanidine ultracentrifugation (Chirwin et al. (1979) Biochemistry 18: 5294-5299) or AGPC (Chomczynski and Sacchi (1987) Anal. Biochem. 162: 156-159), followed by purification of mRNA using the mRNA Purification Kit (Pharmacia), or such. A kit for direct mRNA preparation, such as the QuickPrep mRNA Purification Kit (Pharmacia), may also be used. Next, cDNA is synthesized from the resulting mRNA using reverse transcriptase. cDNA synthesis kits such as the AMV Reverse Transcriptase First-strand cDNA Synthesis Kit (Seikagaku Corporation) are also available commercially. Other methods that use the 5'-RACE method to synthesize and amplify cDNA by PCR may also be used (Frohman et al. (1988) Proc. Natl. Acad. Sci. USA 85: 8998-9002; Belyavsky et al. (1989) Nucleic Acids Res. 17: 2919-32). In addition, in order to construct cDNA libraries containing a high percentage of full-length clones, known techniques such as the oligo-capping method (Maruyama and Sugano (1994) Gene 138: 171-4; Suzuki (1997) Gene 200: 149-56) can also be employed. The cDNA obtained in this manner is then incorporated into a suitable vector.

Examples of hybridization conditions in the present invention include "2×SSC, 0.1% SDS, 50° C.", "2×SSC, 0.1% SDS, 42° C." and "1×SSC, 0.1% SDS, 37° C.". Examples of conditions of higher stringency include "2×SSC, 0.1% SDS, 65° C.", "0.5×SSC, 0.1% SDS, 42° C." and "0.2×SSC, 0.1% SDS, 65° C.". More specifically, a method that uses the Rapid-hyb buffer (Amersham Life Science) can be carried out by performing pre-hybridization at 68° C. for 30 minutes or more, adding a probe to allow hybrid formation at 68° C. for 1 hour or more, washing three times in 2×SSC/0.1% SDS at room temperature for 20 minutes each, washing three times in 1×SSC/0.1% SDS at 37° C. for 20 minutes each, and finally washing twice in 1×SSC/0.1% SDS at 50° C. for 20 minutes each. This can also be carried out using, for example, the Expresshyb Hybridization Solution (CLONTECH), by performing pre-hybridization at 55° C. for 30 minutes or more, adding a labeled probe and incubating at 37° C. to 55° C. for 1 hour or more, washing three times in 2×SSC/0.1% SDS at room temperature for 20 minutes each, and washing once at 37° C. for 20 minutes with 1×SSC/0.1% SDS. Here, conditions of higher stringency can be achieved by increasing the temperature for pre-hybridization, hybridization, or second wash. For example, a pre-hybridization and hybridization temperature of 60° C. can be raised to 68° C. for higher stringency. In addition to factors such as salt concentration of the buffer and temperature, a person with ordinary skill in the art can also integrate other factors such as probe concentration, probe length, and reaction time, to obtain murine 65B13 isoforms and allelic mutants attained in the Examples of the present invention, and corresponding genes derived from other organisms.

References such as Molecular Cloning, A Laboratory Manual $2^{nd}$ ed. (Cold Spring Harbor Press (1989); Section 9.47-9.58), Current Protocols in Molecular Biology (John Wiley & Sons (1987-1997); Section 6.3-6.4), DNA Cloning 1: Core Techniques, A Practical Approach $2^{nd}$ ed. (Oxford University (1995); Section 2.10 for conditions, in particular), can be referred to for detailed information on hybridization procedures. Examples of hybridizing polynucleotides include polynucleotides containing a nucleotide sequence that has at least 50% or more, preferably 70%, more preferably 80% and even more preferably 90% (for example, 95% or more, or 99%) identity with a nucleotide sequence comprising nucleotides 177 to 2280 of SEQ ID NO: 1 or nucleotides 127 to 2079 of SEQ ID NO: 2. Such identities can be determined by the BLAST algorithm (Altschul (1990) Proc. Natl. Acad. Sci. USA 87: 2264-8; Karlin and Altschul (1993) Proc. Natl. Acad. Sci. USA 90: 5873-7). Examples of programs that have been developed based on this algorithm include the BLASTX program for determining the identity of amino acid sequences, and the BLASTN program for nucleotide sequences (Altschul et al. (1990) J. Mol. Biol. 215: 403-10). These programs can be used for the sequences of the present invention (see http://www.ncbi.nlm.nih.gov. for a specific example of analysis methods).

65B13 isoforms or allelic mutants, and other genes with a 65B13-like structure or function, can be obtained from cDNA libraries and genome libraries of animals such as humans, mice, rats, rabbits, hamsters, chickens, pigs, cows, goats, and sheep, by designing primers based on the nucleotide sequences of SEQ ID NOs: 1 and 2, using gene amplification technology (PCR) (Current Protocols in Molecular Biology, John Wiley & Sons (1987) Sections 6.1-6.4).

For example, BLAST search results revealed three human sequences of unknown function that are 84% identical to the nucleotide sequence of mouse 65B13 of the present invention (GenBank Accession No.: XM_048304, AL136654, BC007312). The respective nucleotide sequences are listed as SEQ ID NOs: 5, 7, and 9, with their predicted amino acid sequences listed as SEQ ID NOs: 6, 8, and 10, and are considered human homologues of mouse 65B13. According to the methods of the present invention, such human homologues can be used to select human dopaminergic neuron precursor cells. All three sequences are believed to be sequences derived from the same gene on chromosome 19, based on reported information. Among them, two sequences AL136654 (SEQ ID NO: 7) and BC007312 (SEQ ID NO: 9) are cDNA fragments, while the third sequence XM_048304 (SEQ ID NO: 5) is considered an mRNA sequence predicted from the genome sequence. These predicted sequences have ORFs that are similar in size to 65B13 of the present invention, and the predicted amino acid sequences share an 84% identity with 65B13.

The polynucleotide sequences of the present invention can be confirmed by using conventional sequence determination methods. For example, the dideoxynucleotide chain termination method (Sanger et al. (1977) Proc. Natl. Acad. Sci. USA 74: 5463) can be used. In addition, sequences can also be analyzed using a suitable DNA sequencer.

<Nucleotide Chains>

Moreover, a nucleotide chain complementary to a polynucleotide of the present invention comprising at least 15 nucleotides is provided by the present invention. Here, a "complementary sequence" refers to not only cases where at least 15 consecutive nucleotides of the nucleotide sequence completely pair with the template, but also includes those that have at least 70%, preferably 80%, more preferably 90% and even more preferably 95% or more (for example, 97% or 99%) of the consecutive nucleotides paired with the template. Pair formation refers to the formation of a chain, in which T (U in the case of an RNA) corresponds to A, A corresponds to T or U, G corresponds to C, and C corresponds to G in the nucleotide sequence of the template polynucleotide. Identities can be determined by methods similar to that used in the aforementioned polynucleotide hybridization.

Such a nucleotide chain of the present invention can be used as a probe for detecting or isolating, or as a primer for amplifying the polynucleotides of the present invention. The nucleotide chain normally consists of 15 to 100, and preferably 15 to 35 nucleotides when used as a probe, or at least 15 and preferably 30 nucleotides when used as a primer. A primer can be designed to have a restriction enzyme recognition sequence, a tag or such, added to the 5'-end side thereof, and at the 3' end, a sequence complementary to a target sequence. A nucleotide chain of the present invention can hybridize with a polynucleotide of the present invention.

Moreover, mutations of a polynucleotide of the present invention within cells can be detected using these probes or primers. In some cases, such mutations may cause abnormalities in the activity or expression of the polypeptides of the present invention, therefore, nucleotide chains of the present inventions are thought to be useful for disease diagnosis and such.

In addition, the nucleotide chains of the present invention include antisense nucleic acids that suppress the cellular expression of a polynucleotide of the present invention by binding to an mRNA or DNA, and ribozymes that suppress via specific cleavage of mRNA.

Examples of antisense mechanisms to suppress target gene expression include: (1) inhibition of transcription initiation via triplex formation, (2) transcription suppression through hybrid formation at sites of local open-loop structure formed by RNA polymerases, (3) transcription inhibition through hybrid formation with RNA during synthesis, (4) suppression of splicing through hybrid formation at intron-exon junctions, (5) suppression of splicing through hybrid formation at sites of spliceosome formation, (6) suppression of mRNA migration to the cytoplasm through hybrid formation with mRNA, (7) suppression of splicing through hybrid formation at a capping site or poly A addition site, (8) suppression of translation initiation through hybrid formation at the binding sites of initiation factors, (9) translation suppression through hybrid formation at ribosome binding sites, (10) suppression of peptide chain elongation through hybrid formation at mRNA coding regions or polysome binding sites, and (11) suppression of gene expression through hybrid formation at sites of nucleic acid/protein interaction (Hirashima and Inoue, "New Biochemistry Experiment Course 2, Nucleic Acids IV, Gene Replication and Expression", Japanese Biochemical Society edit., Tokyo Kagaku Dozin Publishing, pp. 319-347 (1993)).

An antisense nucleic acid contained in a nucleotide chain of the present invention may be a nucleic acid that inhibits gene expression by any of the mechanisms described in (1) to (11) above. Namely, it may contain an antisense sequence to not only the coding region, but also to a non-coding region sequence of a target gene whose expression is to be inhibited. A DNA that encodes an antisense nucleic acid can be used by linking to a suitable regulatory sequence that allows its expression. The antisense nucleic acid does not need to be completely complementary to the coding region or non-coding region of a target gene, as long as it can effectively inhibit the expression of the gene. Such antisense nucleic acids have a chain length of at least 15 bp or more, preferably 100 bp or more, and more preferably 500 bp or more, and are normally within 3000 bp, preferably within 2000 bp and more preferably within 1000 bp. It is preferred that such antisense nucleic acids share an identity of 90% or more, and more preferably 95% or more, with the complementary chain of a target gene transcription product. These antisense nucleic acids can be prepared according to the phosphothionate method (Stein (1988) Nucleic Acids Res. 16: 3209-3221) using the polynucleotides of the present invention.

"Ribozyme" is a generic term referring to catalysts with an RNA component, and ribozymes are broadly classified into large ribozymes and small ribozymes. Large ribozymes are enzymes that cleave the phosphate-ester bonds of a nucleic acid and leave the reaction sites with 5'-phosphoric acid and 3'-hydroxyl group at the end of a reaction. Large ribozymes are further classified into (1) group I intron RNAs, which undergo guanosine-initiated trans-esterification reactions at 5'-spliced sites, (2) group II intron RNAs, which undergo two-step self-splicing reactions with a resultant lariat structure, and (3) RNA components of ribonuclease P, which cleave precursor tRNAs at their 5' side via hydrolysis reactions. In contrast, small ribozymes are comparatively small structural units (about 40 bp) that cleave RNAs, forming 5'-hydroxyl groups and 2'-3' cyclic phosphoric acids. Small ribozymes include, for example, hammerhead-type ribozymes (Koizumi et al. (1988) FEBS Lett. 228: 225) and hairpin-type ribozymes (Buzayan (1986) Nature 323: 349; Kikuchi and Sasaki (1992) Nucleic Acids Res. 19: 6571; H. Kikuchi (1992) Chemistry and Biology 30: 112). Since ribozymes are easily altered and synthesized, various modification methods are known. For example, hammerhead-type ribozymes that recognize and cleave nucleotide sequence UC, UU, or UA within a target RNA can be created, by designing the substrate binding portion of a ribozyme to be complementary to an RNA sequence near the target site (Koizumi et al. (1988) FEBS Lett. 228: 225; M. Koizumi and E. Ohtsuka (1990) Protein, Nucleic Acid, and Enzyme 35: 2191; Koizumi et al. (1989) Nucleic Acids Res. 17: 7059). Hairpin-type ribozymes can also be designed and produced using known methods (Kikuchi and Sasaki (1992) Nucleic Acids Res. 19: 6571; H. Kikuchi (1992) Chemistry and Biology 30: 112).

Antisense nucleic acids and ribozymes comprised in the nucleotide chains of the present invention can also be used as virus vectors derived from retroviruses, adenoviruses, adeno-associated viruses, and such, non-virus vectors that use liposomes, or naked DNAs, to control gene expression in cells using ex vivo or in vivo methods for gene therapy.

The nucleotide sequences of the nucleotide chains of the present invention can be confirmed by the same methods used for the aforementioned polynucleotides.

<Vectors>

Vectors comprising a polynucleotide of the present invention are provided by the present invention. A vector of the present invention is useful for carrying a polynucleotide of the present invention within host cells, or for expressing a polypeptide encoded by the polynucleotide. This vector includes various vectors such as plasmids, cosmids, viruses, bacteriophages, cloning vectors, and expression vectors (Molecular Cloning, A Laboratory Manual $2^{nd}$ ed., Cold Spring Harbor Press (1989); Current Protocols in Molecular Biology, John Wiley & Sons (1987)). In a preferred embodiment, a polynucleotide of the present invention is expressed in a host cell, into which a vector of the present invention has been introduced, by linking to the downstream of a regulatory sequence. Here, "regulatory sequence" includes promoters, ribosome binding sites, and terminators in the case of a prokaryotic host cell, and promoters and terminators in the case of a eukaryotic host cell, and in some cases, may also contain transactivators, transcription factors, poly A signals which stabilize transcription products, splicing and polyadenylation signals, and others. Such a regulatory sequence comprises all the components required for the expression of a polynucleotide linked thereto. In addition, a vector of the present invention preferably comprises a selection marker. Moreover, a signal peptide required for transferring an intracellularlly expressed polypeptide into the lumen of the endoplasmic reticulum, or the periplasm or extracellular space when the host is a Gram negative microbe, can also be incorporated into an expression vector by linking to a polypeptide of interest. Such a signal peptide may comprise the 17 amino acid residues seen in naturally-occurring 65B13. Alternatively, it can be a signal peptide derived from a heterogeneous protein. Moreover, a linker may be added, and a start (ATG) or stop codon (TAA, TAG or TGA) may be inserted as necessary.

A vector of the present invention is preferably an expression vector. An "expression vector" refers to a construct capable of expressing a polypeptide encoded in an expression vector in target host cells in vitro. The expression vectors of the present invention include cloning vectors, binary vectors, integration vectors, and such. Expression processes include transcription of the coding sequence comprised on an expression vector into translatable mRNA, translation of the mRNA into a polypeptide of the present invention, and in some cases, secretion of the expressed polypeptide into the lumen of the endoplasmic reticulum, the periplasm, or extracellular space.

pBEST (Promega) is an example of a vector capable of expressing polynucleotides in vitro. In addition, examples of promoters capable of expressing polynucleotides in prokaryotic cells such as E. coli, include $P_L$, araB (Better et al. (1988) Science 240: 1041-3), lacZ (Ward et al. (1989) Nature 341: 544-6; Ward et al. (1992) FASEB J. 6: 2422-7), trp, tac and trc (fusion of lac and trp). In addition, terminators derived from trpA, phages, and rrnB ribosomal RNAs can also be used. Moreover, vectors to be used in E. coli preferably have an "ori" for amplifying the vector within a host, and a marker gene for selecting a transformed host. The use of a drug resistance gene is preferred, which allows the host to be distinguished by drugs such as ampicillin, tetracyclin, kanamycin, and chloramphenicol. The pelB signal sequence can be used, particularly if the polypeptide is intended for secretion into the periplasm (Lei et al. (1987) J. Bacteriol. 169: 4379). Examples include M13 vectors, pUC vectors, pBR322, pCR-Script, pGEX-5X-1 (Pharmacia), pEGFP, pBluescript (Stratagene), and pET (Invitrogen; a preferable host for this vector is BL21 expressing the T7 polymerase). In addition, subcloning or excision vectors can be exemplified by pGEM-T, pDIRECT and pT7, in particular.

An example of a bacterial host other than E. coli is the genus Bacillus, and examples of vectors include pUB110 and pc194 vectors. Specific examples include pPL608 and pKTH50 derived from Bacillus subtilis. Vectors have also been developed for host bacteria, for example, genus Pseudomonas such as Pseudomonas putida and Pseudomonas cepacia, genus Brevibacterium such as Brevibacterium lactofermentum (pAJ43 (Gene 39: 281 (1985) etc.)), genus Corynebacterium such as Corynebacterium glutamicum (pCS11 (Unexamined Published Japanese Patent Application No. Sho 57-183799); pCB101 (Mol. Gen. Genet. 196: 175 (1984), etc.)), genus Streptococcus (pHV1301 (FEMS Microbiol. Lett. 26: 239 (1985)); pGK1 (Appl. Environ. Microbiol. 50: 94 (1985)), etc.), genus Lactobacillus (pAMβ1 (J. Bacteriol. 137: 614 (1979), etc.)), genus Rhodococcus such as Rhodococcus rhodochrous (J. Gen. Microbiol. 138: 1003 (1992)), and genus Streptomyces such as Streptomyces lividans and Streptomyces virginiae (see Genetic Manipulation of Streptomyces: A Laboratory Manual, Hopwood et al., Cold Spring Harbor Laboratories (1985); pIJ486 (Mol. Gen. Genet. 203: 468-478 (1986)), pKC1064 (Gene 103: 97-9 (1991)), pUWL-KS (Gene 165: 149-50 (1995))). See literatures such as "Basic Microbiology Course 8-Genetic Engineering" (Kyoritsu Publishing) for useful vectors in microbe hosts. Techniques such as the calcium chloride method (Mandel and Higa (1970) J. Mol. Biol. 53: 158-162; Hanahan (1983) J. Mol. Biol. 166: 557-580) and electroporation can be employed to introduce a vector into a host.

Further, regulatory elements for expression in eukaryotic cell hosts are exemplified by the AOX1 and GAL1 promoters for yeast hosts. Examples of expression vectors derived from yeasts include the Pichia Expression Kit (Invitrogen), pNV11 and SP-Q01. Vectors that can be used in yeasts are described in detail in, for example, Adv. Biochem. Eng. 43: 75-102 (1990) and Yeast 8: 423-88 (1992). More specifically, vectors such as YRp, YEp, Ycp, and YIp can be used in genus Saccharomyces such as Saccharomyces cerevisiae. Integration vectors (such as EP537456), which allow a large number of gene copies to be inserted, and can stably maintain the inserted genes, are particularly useful. Other examples of vectors include 2 μm vectors derived from S. cerevisiae, pKD1 vectors (J. Bacteriol. 145: 382-90 (1981), pGK11-derived vectors, and Kluyveromyces autonomous replication gene KARS vectors for genus Kluyveromyces such as Kluyveromyces lactis; vectors described in Mol. Cell. Biol. 6: 80 (1986) and pAUR224 (Takara Shuzo) for genus Schizosaccharomyces; pSB3-derived vectors (Nucleic Acids Res. 13: 4267 (1985)) for genus Zygosaccharomyces; vectors described in literatures such as Yeast 7: 431-43 (1991), Mol. Cell. Biol. 5: 3376 (1985) and Nucleic Acids Res. 15: 3859 (1987) for genus Pichia such as Pichia angusta and Pichia pastoris; vectors described in Unexamined Published Japanese Patent Application No. Hei 8-173170 or vectors using ARS derived from Candida maltosa (Agri. Biol. Chem. 51: 1587 (1987)) for C. maltosa, C. albicans, C. tropicalis or C. utilis; vectors described in Trends in Biotechnology 7: 283-7 (1989) for genus Aspergillus such as Aspergillus niger and A. oryzae; and vectors using promoters derived from the extracellular cellulase gene (Bio/technology 7: 596-603 (1989)) in genus Trichoderma.

For hosts of mammalian cells or other animal cells, the adenovirus late promoter (Kaufman et al. (1989) Mol. Cell. Biol. 9: 946), CAG promoter (Niwa et al. (1991) Gene 108: 193-200), CMV immediate-early promoter (Seed and Aruffo (1987) Proc. Natl. Acad. Sci. USA 84: 3365-9), EF1α promoter (Mizushima et al. (1990) Nucleic Acids Res. 18: 5322; Kim et al. (1990) Gene 91: 217-23), HSV TK promoter, SRα promoter (Takebe et al. (1988) Mol. Cell. Biol. 8: 466), SV40 promoter (Mulligan et al. (1979) Nature 277: 108), SV40 early promoter (Genetic Engineering Vol. 3, Williamson ed., Academic Press (1982) pp. 83-141), SV40 late promoter (Gheysen and Fiers (1982) J. Mol. Appl. Genet. 1: 385-94), RSV (Rous sarcoma virus)-LTR promoter (Cullen (1987) Methods Enzymol. 152: 684-704), MMLV-LTR promoter, CMV enhancer, SV40 enhancer and globin intron, and such can be used.

Moreover, the vector preferably comprises a drug resistance gene to allow cells to be distinguished by drugs such as neomycin or G418. To increase the number of gene copies within cells, the number of copies can be amplified by using methotrexate (MTX) in, for example, a CHO host which is defective in the nucleic acid synthesis pathway, and employing a vector such as pCHOI, which has a DHFR gene to compensate for the defect. On the other hand, in order to transiently express a gene, COS cells having an SV40 T antigen gene on their chromosomes can be used as the host, and a vector having an SV40 replication origin, such as pcD, or a vector having a replication origin of adenovirus, bovine papilloma virus (BPV), polyoma virus, and such can be used. Moreover, a gene encoding aminoglycoside transferase (APH), thymidine kinase (TK), xanthine-guanine phosphoribosyl transferase (Ecogpt), dihydrofolic acid reductase (dhfr), or such may be included as a selection marker for amplifying the gene copy number. Known examples of suitable vectors are the Okayama-Berg expression vector pcDV1 (Pharmacia), pCDM8 (Nature 329: 840-2 (1987)), pRc/CMV, pcDNA1, pcDNA3 (Invitrogen), pSPORT1 (GIBCO BRL), pSV2dhfr (Mol. Cell. Biol. 1: 854-64 (1981)), pEF-BOS (Nucleic Acids Res. 18: 5322 (1990)), pCEP4 (Invitrogen), pMAM, pDR2, pBK-RSV, pBK-CMV, pOPRSV, pOP13, and pME18S (Mol. Cell. Biol. 8: 466-72 (1988)).

In particular, examples of vectors used to express a polynucleotide of the present invention in animals in vivo include adenovirus vectors such as pAdexlcw and retrovirus vectors such as pZIPneo. A vector can be introduced into a host using methods such as the adenovirus methods, electroporation (Cytotechnology 3: 133 (1990)), cationic liposome methods (Cationic Liposome DOTAP (Boehringer Mannheim), etc.), introduction using positively charged polymers, electrostatic type liposome methods, internal type liposome methods, particle gun methods, liposome methods, lipofection (Proc. Natl. Acad. Sci. USA 84: 7413 (1987)), calcium phosphate methods (Unexamined Published Japanese Patent Application No. Hei 2-227075), receptor-mediated gene introduction methods, retrovirus methods, DEAE dextran methods, virus-liposome methods (Experimental Medicine Supplement, "Basic Technology of Gene Therapy", Yodosha (1997); Experimental Medicine Supplement, "Experimental Method of Gene Introduction and Expression Analysis", Yodosha (1997); J. Clin. Invest. 93: 1458-64 (1994); Am. J. Physiol. 271: R1212-20 (1996); Molecular Medicine 30: 1440-8 (1993); Experimental Medicine 12: 1822-6 (1994); Protein, Nucleic acid, and Enzyme 42: 1806-13 (1997); Circulation 92 (Suppl. II): 479-82 (1995)), and naked-DNA direct introduction methods. Vectors generated using virus vectors derived from viruses other than adenoviruses and retroviruses, such as adeno-associated virus, Sindbis virus, Sendai virus, Togavirus, Paramyxovirus, poxvirus, poliovirus, herpes virus, lentivirus and vaccinia virus, can also be used. Administration into the living body may be carried out using ex vivo or in vivo methods.

In addition, insect expression systems are also known as systems for expressing heterogeneous polypeptides. For example, exogenous genes can be expressed in *Spodoptera frugiperda* cells or *Trichoplusia larvae* cells, using the *Autographa california* nucleopolyhedrosis virus (AcNPV) as a vector. Here, an exogenous gene of interest is cloned into the non-essential region of a virus. For example, it may be linked to a region under the control of a polyhedrin promoter. In this case, the polyhedrin gene is deactivated, a recombinant virus lacking the coat protein is produced, and a polypeptide of interest is expressed in cells of *Spodoptera frugiperda, Trichoplusia larvae*, or such, that have been infected with the virus (Smith (1983) J. Virol. 46: 584; Engelhard (1994) Proc. Natl. Acad. Sci. USA 91: 3224-7). Other known examples of insect cell-derived expression vectors include the Bac-to-BAC Baculovirus Expression System (Bigco BRL) and pBacPAK8.

When plant cells are used as a host, for example, vectors that use the 35S promoter of cauliflower mosaic virus can be used. Known methods of introducing a vector into plant cells include the PEG, electroporation, *Agrobacterium* methods, and particle gun methods.

Insertion of a DNA into a vector can be carried out in a ligase reaction using restriction enzyme sites (Current Protocols in Molecular Biology, John Wiley & Sons (1987) Section 11.4-11.11; Molecular Cloning, A Laboratory Manual 2$^{nd}$ ed., Cold Spring Harbor Press (1989) Section 5.61-5.63).

<Hosts>

The present invention provides hosts that comprise a polynucleotide or vector of the present invention. An in vitro or in vivo production system may be employed for the production of a polypeptide of the present invention. Hosts of the present invention include archaebacterial, bacterial, fungal, plant, insect, fish, amphibian, reptilian, avian, and mammalian prokaryotic and eukaryotic cells. A host of the present invention comprises in its cells a polynucleotide that encodes a polypeptide of the present invention. As long as the polynucleotide does not exist at a naturally occurring position in the genome of a host cell, the polynucleotide may be regulated by its own promoter, incorporated into the host genome, or maintained as an extrachromosomal structure.

Examples of bacterial hosts include Gram positive and Gram negative bacteria belonging to the genus *Escherichia, Streptococcus, Staphylococcus, Serratia* or *Bacillus*, such as *E. coli* (JM109, DH5α, HB101 and XL1Blue), *Serratia marcescens*, and *Bacillus subtilis*.

Examples of a eukaryotic host include fungal cells such as yeasts, higher plants (*Nicotiana tabacum* derived cells), insects (*Drosophila* S2, *Spodoptera* Sf9, Sf21, Tn5), fish, amphibians (*Xenopus* oocytes (Valle et al. (1981) Nature 291: 358-40), reptiles, birds, and mammals (CHO (J. Exp. Med. 108: 945 (1995). Among them, DHFR gene-deficient dhfr-CHO (Proc. Natl. Acad. Sci. USA 77: 4216-20 (1980) and CHO K-1 (Proc. Natl. Acad. Sci. USA 60: 1275 (1968)), COS, Hela, C127, 3T3, BHK, HEK293 and Bowes melanoma cells), myeloma, Vero, Namalwa, Namalwa KJM-1 and HBT5637 (Unexamined Published Japanese Patent Application No. Sho 63-299), and plants (potato, tobacco, corn, rice, rape, soybean, tomato, wheat, barley, rye, alfalfa, and hemp), are included. In addition to *Saccharomyces cerevisiae* belonging to the genus *Saccharomyces*, and yeasts belonging to the genus *Pichia*, expression systems that use fungi as a host, such as the cells of *Aspergillus niger* belonging to the mold *Aspergillus*, are also known.

Introduction of a vector into host cells can be carried out using methods such as the electroporation (Chu et al. (1987) Nucleic Acids Res. 15: 1311-26), cationic liposome methods, electric pulse terebration (Current Protocols in Molecular Biology, John Wiley & Sons (1987) Sections 9.1 to 9.9), direct injection using a microscopic glass tube, microinjection, lipofection (Derijard (1994) Cell 7: 1025-37; Lamb (1993) Nature Genetics 5: 22-30; Rabindran et al. (1993) Science 259: 230-4), lipofectamine method (GIBCO-BRL), calcium phosphate method (Chen and Okayama (1987) Mol. Cell. Biol. 7: 2745-52), DEAE dextran method (Lopata et al. (1984) Nucleic Acids Res. 12: 5707-17; Sussman and Milman (1985) Mol. Cell. Biol. 4: 1642-3) and FuGene6 reagent (Boehringer-Mannheim).

<Polypeptides and Polypeptide Fragments>

A "polypeptide" of the present invention refers to a peptide polymer encoded by a polynucleotide of the present invention. Preferred examples include proteins having the amino acid sequence described in SEQ ID NOs: 3 or 4. The polypeptides of the present invention may comprise naturally occurring or modified amino acid residues. Examples of amino acid residue modifications include acylation, acetylation, amidation, arginylation, GPI anchor formation, crosslinking, γ-carboxylation, cyclization, covalent crosslink formation, glycosylation, oxidation, covalent bonding of a lipid or fat derivative, cystine formation, disulfide bond formation, selenoylation, demethylation, protein fragmentation treatment, covalent bonding of a nucleotide or nucleotide derivative, hydroxylation, pyroglutamate formation, covalent bonding of a flavin, prenylation, covalent bonding with a heme portion, covalent bonding of phosphatidyl inositol, formylation, myristoylation, methylation, ubiquitination, iodination, racemization, ADP-ribosylation, sulfation and phosphorylation. Moreover, the polypeptides of the present invention include precursors containing a signal peptide portion, mature proteins lacking a signal peptide portion, and fusion proteins modified with other peptide sequences. Peptide sequences to be added to a polypeptide of the present invention can be selected from sequences that facilitate protein purification using, for example, pcDNA3.1/Myc-His vector (Invitrogen), or those that confer stability in recombinant protein production. Examples of such sequences are influenza agglutinin (HA), glutathione S transferase (GST), substance P, multiple histidine tag (such as 6×His and 10×His), protein C fragment, maltose-binding protein (MBP), immunoglobulin constant region, α-tubulin fragment, β-galactosidase, B-tag, c-myc fragment, E-tag (epitope on a monoclonal phage), FLAG (Hopp et al. (1988) Bio/Technol. 6: 1204-10), lck tag, p18 HIV fragment, HSV-tag (human simple Herpes virus glycoprotein), SV40T antigen fragment, T7-tag (T7 gene 10 protein), and VSV-GP fragment (vesicular stomatitis virus glycoprotein).

Moreover, the present invention also provides fragments of the polypeptides of the present invention. A polypeptide fragment of the present invention is identical to a portion of a polypeptide of the present invention, and comprises at least eight amino acid residues or more (for example, 8, 10, 12 or 15 amino acid residues or more). A particularly preferable fragment can be exemplified by a polypeptide fragment lacking an amino terminus, carboxyl terminus, and transmembrane domain. The polypeptide fragments of the present invention include fragments containing an α-helix and α-helix forming region, α-amphipathic region, β-sheet and α-sheet forming region, β-amphipathic region, substrate binding region, high antigen index region, coil and coil forming region, hydrophilic region, hydrophobic region, turn and turn forming region, and surface forming region. A polypeptide fragment of the present invention may be any fragment, provided that it has the antigenicity of a polypeptide of the present invention. The antigen-determining site of a polypeptide can be predicted using methods for analyzing protein hydrophobicity and hydrophilicity of an amino acid sequence (Kyte-Doolittle (1982) J. Mol. Biol. 157: 105-22), or methods of secondary structure analysis (Chou-Fasman (1978) Ann. Rev. Biochem. 47: 251-76), and can be confirmed using a computer program (Anal. Biochem. 151: 540-6 (1985), or the PEPSCAN method in which a short peptide is synthesized followed by confirmation of its antigenicity (Published Japanese Translation of International Publication No. Sho 60-500684).

The polypeptides or polypeptide fragments of the present invention can be produced by using known genetic recombination techniques or chemical synthesis. When producing a polypeptide or polypeptide fragment of the present invention using genetic recombination techniques, the produced protein may or may not be subjected to glycosylation depending on the type of host selected, and may differ in molecular weight, isoelectric point or such. Normally when a polypeptide is expressed using a prokaryotic cell such as *E. coli* as the host, the resulting polypeptide is produced in a form that has a methionine residue attached to the N terminus of the original polypeptide. Polypeptides having different structures due to such differences in host are also included in the polypeptides of the present invention.

<Polypeptide Production>

For in vitro polypeptide production, polypeptides can be produced in an in vitro cell-free system using methods such as in vitro translation (Dasso and Jackson (1989) Nucleic Acids Res. 17: 3129-44). In contrast, when producing polypeptides using cells, a suitable cell host is first selected from those mentioned above, and then the cells are transformed with a DNA of interest. Subsequently, the transformed cells can be cultured to obtain a polypeptide of interest. Culturing is carried out using known methods that are appropriate for the cell host selected. For example, when animal cells are selected, culturing can be carried out at a pH of about 6 to 8 and a temperature of 30° C. to 40° C. for about 15 to 200 hours, using a medium such as DMEM (Virology 8: 396 (1959)), MEM (Science 122: 501 (1952)), RPMI1640 (J. Am. Med. Assoc. 199: 519 (1967)), 199 (Proc. Soc. Biol. Med. 73: 1 (1950)) or IMDM, and adding serum such as fetal calf serum (FCS), as necessary. In addition, the medium may be replaced, aerated, or stirred, during the course of culturing, as necessary.

On the other hand, in order to establish an in vivo polypeptide production system, a DNA of interest is introduced into an animal or plant, and the polypeptide is produced in vivo. Examples of known animal systems (Lubon (1998) Biotechnol. Annu. Rev. 4: 1-54) include mammals such as goats, pigs, sheep, mice, and cows, and insects such as silkworms (Susumu (1985) Nature 315: 592-4). In addition, transgenic animals can also be used in mammalian systems.

For example, when secreting a polypeptide of interest in goat milk, a DNA that encodes the polypeptide is linked to a DNA that encodes a protein such as β-casein, and a fusion protein of the polypeptide of interest is specifically expressed in milk. Next, the DNA that encodes the fusion protein is introduced into a goat embryo. The embryo harboring this DNA is then transferred back into the uterus of a female goat. The transgenic goats or their offspring born from this female goat secretes the polypeptide of interest in their milk. Hormones may also be administered to increase the amount of milk, as necessary (Ebert et al. (1994) Bio/Technology 12: 699-702).

Transgenic plant polypeptide production systems using plants such as tobacco are known. First, a DNA that encodes a polypeptide of interest is incorporated into a plant expression vector such as pMON530, and this vector is then introduced into a bacterium such as *Agrobacterium tumefaciens*. A bacterium harboring this DNA is then used to infect plants such as *Nicotina tabacum*, and the polypeptide of interest can be isolated from the leaves of the resulting transgenic plant upon regeneration of the plant body (Julian et al. (1994) Eur. J. Immunol. 24: 131-8). Examples of other established methods include methods in which a DNA is introduced into a protoplast using PEG followed by regeneration of the plant body (Gene Transfer to Plants, Potrykus and Spangenberg ed. (1995) pp. 66-74; suitable for Indian rice varieties), methods in which a DNA is introduced into a protoplast by electric pulse followed by regeneration of the plant body (Toki et al. (1992) Plant Physiol. 100: 1503-7; suitable for Japanese rice varieties), methods in which a DNA is directly introduced into plant cells using the particle gun method followed by regeneration of the plant body (Christou et al. (1991) Bio/Technology 9: 957-62), and methods in which a DNA is introduced into cells via *Agrobacterium* followed by regeneration of the plant body (Hiei et al. (1994) Plant J. 6: 271-82). See Toki et al. (1995) Plant Physiol. 100: 1503-7 for methods of plant regeneration.

Once a transgenic plant is obtained, a plant host that produces a polypeptide of the present invention can be propagated in the same manner, using the seeds, fruits, tubers, root tubers, stocks, cuttings, calluses, or protoplasts of the plant.

Normally, a polypeptide of the present invention produced by gene recombination techniques can be recovered from the medium if the polypeptide is secreted outside of a cell, or from the body fluid of a transgenic organism. When a polypeptide is produced inside of a cell, the cells are dissolved and the polypeptide is recovered from the dissolved product. The polypeptide of interest is then purified by suitably combining known methods of protein purification such as salting out, distillation, various types of chromatography, gel electrophoresis, gel filtration, ultrafiltration, recrystallization, acid extraction, dialysis, immunoprecipitation, solvent precipitation, solvent extraction, and ammonium sulfate or ethanol precipitation. Examples of chromatographies include ion exchange chromatography, such as anion or cation exchange chromatography, affinity chromatography, reversed-phase chromatography, adsorption chromatography, gel filtration chromatography, hydrophobic chromatography, hydroxyapatite chromatography, phosphocellulose chromatography, and lectin chromatography (Strategies for Protein Purification and Characterization: A Laboratory Course Manual, Marshak et al. ed., Cold Spring Harbor Laboratory Press (1996)). Chromatography can be carried out using a liquid phase chromatography such as HPLC or FPLC.

In addition, naturally-occurring polypeptides can also be purified and obtained. For example, polypeptides can be purified by affinity chromatography using antibodies against the polypeptides of the present invention to be described below (Current Protocols in Molecular Biology, John Wiley & Sons (1987) Section 16.1-16.19). In addition, purification can also be carried out using a glutathione column for GST-fusion proteins, or a nickel column for histidine-tagged fusion proteins. When producing a polypeptide of the present invention in the form of a fusion protein, unwanted portions can be cleaved using thrombin or factor Xa and such, following purification, as necessary. Moreover, the resulting polypeptide can also be modified using enzymes such as chymotrypsin, glucosidase, trypsin, protein kinase, and lysyl endopeptidase, as necessary.

In addition to the aforementioned synthesis and genetic engineering techniques, a polypeptide fragment of the present invention can also be produced by cleaving a polypeptide of the present invention, using suitable enzymes such as peptidase.

<Antibodies>

The present invention also provides antibodies against the polypeptides or polypeptide fragments of the present invention. Antibodies of the present invention also include polyclonal antibodies, monoclonal antibodies, chimeric antibodies, single-chain antibodies (scFV) (Huston et al. (1988) Proc. Natl. Acad. Sci. USA 85: 5879-83; The Pharmacology of Monoclonal Antibody, vol. 113, Rosenburg and Moore ed., Springer Verlag (1994) pp. 269-315), humanized antibodies, multispecific antibodies (LeDoussal et al. (1992) Int. J. Cancer Suppl. 7: 58-62; Paulus (1985) Behring Inst. Mitt. 78: 118-32; Millstein and Cuello (1983) Nature 305: 537-9; Zimmermann (1986) Rev. Physiol. Biochem. Pharmacol. 105: 176-260; Van Dijk et al. (1989) Int. J. Cancer 43: 944-9), and antibody fragments such as Fab, Fab', F(ab')2, Fc, and Fv. Moreover, an antibody of the present invention may also be modified by PEG and such, as necessary. An antibody of the present invention may also be produced in the form of a fusion protein with β-galactosidase, maltose-binding protein, GST, green fluorescent protein (GFP), or such, to allow detection without the use of a secondary antibody. In addition, an antibody may be modified by labeling with biotin or such to allow recovery using avidin, streptoavidin, or such.

An antibody of the present invention can be produced using a polypeptide of the present invention, a fragment thereof, or cells in which a polypeptide or polypeptide fragment of the present invention is expressed, as a sensitized antigen. In addition, a short polypeptide of the present invention, or a fragment thereof, may also be used as an immunogen by coupling to a carrier such as bovine serum albumin, Keyhole-limpet hemocyanin, and ovalbumin. In addition, a polypeptide of the present invention, or a fragment thereof, may be used in combination with a known adjuvant such as aluminum adjuvant, Freund's complete (or incomplete) adjuvant, or pertussis adjuvant, to enhance the immune response to an antigen.

Polyclonal antibodies can be obtained from, for example, the serum of an immunized animal after immunizing a mammal with a polypeptide of the present invention, or a fragment thereof, coupled to a desired adjuvant. Although there are no particular limitations on the mammals used, typical examples include rodents, lagomorphs, and primates. Specific examples include rodents such as mice, rats and hamsters, lagomorphs such as rabbits, and primates such as monkeys, including cynomolgus monkeys, rhesus monkeys, baboons and chimpanzees. Animal immunization is carried out by suitably diluting and suspending a sensitized antigen in phosphate-buffered saline (PBS) or physiological saline, mixing with an adjuvant as necessary until emulsified, and injecting into an animal intraperitoneally or subcutaneously. The sensitized antigen mixed with Freund's incomplete adjuvant is preferably administered several times, every 4 to 21 days. Antibody production can be confirmed by measuring the level of an antibody of interest in the serum using conventional methods. Finally, the serum itself may be used as a polyclonal antibody, or it may be further purified. See, for example, "Current Protocols in Molecular Biology" (John Wiley & Sons (1987) Sections 11.12-11.13), for specific methods.

A monoclonal antibody can be produced by removing the spleen from an animal immunized in the manner described above, separating immunocytes from the spleen, and fusing with a suitable myeloma cell using polyethylene glycol (PEG) or such to establish hybridomas. Cell fusion can be carried out according to the Milstein method (Galfre and Milstein (1981) Methods Enzymol. 73: 3-46). Here, suitable myeloma cells are exemplified particularly by cells that allow chemical selection of fused cells. When using such myeloma cells, fused hybridomas are selected by culturing in a culture medium (HAT culture medium) that contains hypoxanthine, aminopterin and thymidine, which destroy cells other than the fused cells. Next, a clone that produces an antibody against a polypeptide of the present invention, or a fragment thereof, is selected from the established hybridomas. Subsequently, the selected clone is introduced into the abdominal cavity of a mouse or such, and ascites is collected to obtain a monoclonal antibody. See, in addition, "Current Protocols in Molecular Biology" (John Wiley & Sons (1987) Section 11.4-11.11), for information on specific methods.

Hybridomas can also be obtained by first sensitizing human lymphocytes that have been infected by EB virus with an immunogen in vitro, and fusing the sensitized lymphocytes with human myeloma cells (such as U266) to obtain hybridomas that produce human antibodies (Unexamined Published Japanese Patent Application No. Sho 63-17688). In addition, human antibodies can also be obtained by using antibody-producing cells generated by sensitizing a transgenic animal with a human antibody gene repertoire (WO92/03918; WO93-02227; WO94/02602; WO94/25585; WO96/33735; WO96/34096; Mendez et al. (1997) Nat. Genet. 15: 146-156, etc.). Methods that do not use hybridomas can be exemplified by a method in which a cancer gene is introduced to immortalize immunocytes such as antibody producing lymphocytes.

In addition, antibodies can also be produced by genetic recombination techniques (see Borrebaeck and Larrick (1990) Therapeutic Monoclonal Antibodies, MacMillan Publishers Ltd., UK). First, a gene that encodes an antibody is cloned from hybridomas or antibody-producing cells (such as sensitized lymphocytes). The resulting gene is then inserted into a suitable vector, the vector is introduced into a host, and the host is then cultured to produce the antibody. This type of recombinant antibody is also included in the antibodies of the present invention. Typical examples of recombinant antibodies include chimeric antibodies comprising a non-human antibody-derived variable region and a human antibody-derived constant region, and humanized antibodies comprising a non-human-derived antibody complementarity determining region (CDR), human antibody-derived framework region (FR), and human antibody constant region (Jones et al. (1986) Nature 321: 522-5; Reichmann et al. (1988) Nature 332: 323-9; Presta (1992) Curr. Op. Struct. Biol. 2: 593-6; Methods Enzymol. 203: 99-121 (1991)).

Antibody fragments of the present invention can be produced by treating the aforementioned polyclonal or monoclonal antibodies with enzymes such as papain or pepsin. Alternatively, an antibody fragment can be produced by genetic engineering techniques using a gene that encodes an antibody fragment (see Co et al., (1994) J. Immunol. 152: 2968-76; Better and Horwitz (1989) Methods Enzymol. 178: 476-96; Pluckthun and Skerra (1989) Methods Enzymol. 178: 497-515; Lamoyi (1986) Methods Enzymol. 121: 652-63; Rousseaux et al. (1986) 121: 663-9; Bird and Walker (1991) Trends Biotechnol. 9: 132-7).

The multispecific antibodies of the present invention include bispecific antibodies (BsAb), diabodies (Db), and such. Multispecific antibodies can be produced by methods such as (1) chemically coupling antibodies having different specificities with different types of bifunctional linkers (Paulus (1985) Behring Inst. Mill. 78: 118-32), (2) fusing hybridomas that secrete different monoclonal antibodies (Millstein and Cuello (1983) Nature 305: 537-9), or (3) transfecting eukaryotic cell expression systems, such as mouse myeloma cells, with a light chain gene and a heavy chain gene of different polyclonal antibodies (four types of DNA), followed by the isolation of a bispecific monovalent portion (Zimmermann (1986) Rev. Physio. Biochem. Pharmacol. 105:176-260; Van Dijk et al. (1989) Int. J. Cancer 43: 944-9). On the other hand, diabodies are dimer antibody fragments comprising two bivalent polypeptide chains that can be constructed by gene fusion. These can be produced using known methods (see Holliger et al. (1993) Proc. Natl. Acad. Sci. USA 90: 6444-8; EP404097; WO93/11161).

Recovery and purification of antibodies and antibody fragments can be carried out using Protein A and Protein G, or according to the protein purification techniques described in detail under "Production of Polypeptides" (Antibodies: A Laboratory Manual, Ed Harlow and David Lane, Cold Spring Harbor Laboratory (1988)). For example, when using Protein A to purify an antibody of the present invention, known Protein A columns such as Hyper D, POROS or Sepharose F. F. (Pharmacia) can be used. The concentration of the resulting antibody can be determined by measuring the absorbance or by enzyme linked immunoadsorbent assay (ELISA).

Antigen binding activity of an antibody can be determined by absorbance measurement, or by using fluorescent antibody methods, enzyme immunoassay (EIA) methods, radioimmunoassay (RIA) methods, or ELISA. When ELISA is used, an antibody of the present invention is first immobilized onto a support such as a plate. A polypeptide of the present invention is added, and then a sample containing the antibody of interest is added. Here, samples containing an antibody of interest include, for example, culture supernatants of antibody-producing cells, purified antibodies, and such. Next, a secondary antibody that recognizes an antibody of the present invention is added, followed by the incubation of the plate. Subsequently, the plate is washed and the label attached to the secondary antibody is detected. Namely, if a secondary antibody is labeled with alkaline phosphatase, the antigen binding activity can be determined by adding an enzyme substrate such as p-nitrophenyl phosphate, and measuring the absorbance. In addition, a commercially available system such as BLAcore (Pharmacia) can also be used to evaluate antibody activities.

The antibodies of the present invention can be used to purify polypeptides of the present invention, or fragments thereof. In addition, the antibodies of this invention can also be used to obtain dopaminergic neuron precursor cells that can be suitably used in cell transplant therapy for diseases such as Parkinson's disease.

<Selection of Dopaminergic Neurons>

The present invention provides a method of selectively obtaining homogenous populations of dopaminergic neuron precursor cells immediately after the cell cycle exit. More specifically, cells that express a polypeptide of the present invention, namely, immediate postmitotic dopaminergic neuron precursor cells, can be obtained by contacting an antibody against a 65B13 polypeptide of the present invention with a cell sample containing potential dopaminergic neuron precursor cells, and then selecting those cells that have bound to the antibody (see FIGS. 12 through 14). The antibody may also be immobilized on a suitable support prior to cellular contact. Alternatively, cells that bind to the antibody can be selectively recovered, by contacting cells with an antibody and allowing them to bind, and purifying by affinity chromatography for the antibody. For example, if an antibody of the present invention is conjugated to biotin, it can be purified on a plate or column bound with avidin or streptoavidin.

In addition, 65B13 has an adhesion molecule-like structure with an Ig domain (see FIG. 6) and when it is expressed in cultured cells, cells that express 65B13 adhere to each other, but not to those that do not express 65B13. Therefore, the 65B13-mediated adhesion is considered to involve homophilic binding. Based on such properties of the 65B13 polypeptide, dopaminergic neuron precursor cells can also be selected by utilizing the 65B13 polypeptide, particularly the extracellular portion thereof. For example, dopaminergic neuron precursor cells can be obtained by fixing the extracellular portion of the 65B13 polypeptide on a suitable support, and then contacting the support with cells. Thus, the present invention provides methods of selecting dopaminergic neuron precursor cells, wherein the methods comprise the step of contacting a peptide comprising at least the extracellular portion of a polypeptide of the present invention with a cell sample containing dopaminergic neuron precursor cells.

In the present invention, immediate postmitotic dopaminergic neuron precursor cells can be efficiently separated by flow cytometry using an anti-65B13 antibody (Example 4, FIG. 14).

In addition, dopaminergic neuron precursor cells can also be selected using a promoter for 65B13 (see, for example, Unexamined Published Japanese Patent Application No. 2002-51775). For example, a vector harboring a construct that comprises a gene encoding a detection marker, such as GFP, linked to a promoter region obtained from analyzing the 65B13 expression regulatory regions to be described later, can be transfected into cells. In addition, a gene encoding a marker can also be knocked in at the 65B13 gene locus. In either case, specific cells can be selected by detecting the expression of a marker gene specific for dopaminergic neuron precursor cells.

The cell sample used here preferably comprises cells of the ventral midbrain region or cell culture containing in vitro differentiated dopaminergic neurons. In vitro differentiation of dopaminergic neurons can be carried out by known methods using cells such as known ES cells, bone marrow interstitial cells, immortalized neuron-derived cell lines (Published Japanese Translation of International Publication No. Hei 8-5092 15; Published Japanese Translation of International Publication No. Hei 11-506930; Published Japanese Translation of International Publication No. 2002-522070), or primordial neuron cells (Published Japanese Translation of International Publication No. Hei 11-509729), as the starting material. Normally, dopaminergic neurons can be differentiated by co-culturing a tissue obtained from a dopaminergic neuron region of the brain, with a sustentacular cell layer derived from neural tissues. Moreover, methods are also known for deriving dopaminergic cells from neural tissues that normally do not produce dopamine, such as the striatum and cortex (Published Japanese Translation of International Publication No. Hei 10-509319). In addition, culturing under hypoxic conditions has been reported to produce cells containing a greater number of dopaminergic neurons (Published Japanese Translation of International Publication No. 2002-530068). A cell sample used in the selection of dopaminergic neuron precursor cells of the present invention may be a cell population isolated or cultured by any method.

In addition, it is necessary that a support used in immobilizing an antibody or a polypeptide of the present invention be safe to cells. Examples of such a support include synthetic or naturally-occurring organic polymer compounds, inorganic materials such as glass beads, silica gel, alumina, and activated charcoal, and those that have their surfaces coated with a polysaccharide or synthetic polymer. There are no particular limitations on the form of the support, examples of which include films, fibers, granules, hollow fibers, non-woven fabric, porous supports, or honeycombed supports, and the contact surface area can be controlled by changing its thickness, surface area, width, length, shape, and size in various ways.

<Dopaminergic Neuron Precursor Cells>

Since cells obtained in this manner are postmitotic neuron precursor cells, they are preferable in transplant therapy for neurodegenerative diseases, such as Parkinson's disease, in terms of their safety, survival rate, and network formation ability, compared to conventional mixed cell populations or dopaminergic neurons carrying an exogenous gene. Moreover, since cells (or cell populations) of the present invention obtained according to the methods of this invention are immediate postmitotic precursor cells, they can also be differentiated into a suitable stage by selecting in vitro conditions such as media, and are preferable materials for various types of neural transplant therapy. When neuron precursor cells obtained using the methods of the present invention are used in transplants, preferably $1\times10^3$ to $1\times10^6$ cells, and more preferably $5\times10^4$ to $6\times10^4$ cells, are transplanted. The primary method is stereotaxic surgery in which a cell suspension is transplanted into the brain. In addition, cells may also be transplanted by microsurgery. See, Backlund et al. (Backlund et al. (1985) J. Neurosurg. 62: 169-73), Lindvall et al. (Lindvall et al. (1987) Ann. Neurol. 22: 457-68) or Madrazo et al. (Madrazo et al. (1987) New Engl. J. Med. 316: 831-4), for methods of transplanting neuron tissues.

Moreover, the cells of the present invention can also be used to isolate genes specific to dopaminergic neuron precursor cells, and genes specific to each stage of the maturation from precursor cells into dopaminergic neurons. They can also be used for searching therapeutic targets for Parkinson's disease, elucidating the maturation process of dopaminergic neurons, and in screenings using maturation as an indicator.

<Comparison of Gene Expression Levels>

Postmitotic dopaminergic neuron precursor cells, which were obtained using an antibody of the present invention can be used as a material to isolate genes specifically expressed in these cells. They can also be used to investigate and isolate genes specifically expressed in cells that have differentiated, induced, or proliferated from the dopaminergic neuron precursor cells of the present invention. In addition, they can also be used to investigate genes required for in vivo differentiation of dopaminergic neurons, by investigating genes that have different expression levels in cells that have differentiated, induced, or proliferated from the original precursor cells. Since such genes are potential candidates for treating diseases caused by defects in dopaminergic neurons, their determination and isolation are extremely useful.

Comparison of gene expression levels in dopaminergic neuron precursor cells of the present invention with those of cells that have differentiated, induced, or proliferated therefrom, or other cells; or comparison of gene expression levels of the differentiated, induced, or proliferated cells with those of other cells, can be done by commonly used methods, such as cell in situ hybridization, Northern blot hybridization, RNA dot blot hybridization, reverse transcription PCR, RNase protection assay, DNA microarray hybridization, serial analysis of gene expression (SAGE) (Velculescu et al. (1995) Science 270: 484-487), subtractive hybridization, and representation difference analysis (RDA) (Lisitsyn (1995) Trends Genet. 11: 303-307).

For cellular in situ hybridization, locations where RNA processing, transport, and localization into the cytoplasm occur in individual cells can be investigated, by hybridizing total RNA or poly $A^+$ RNA prepared from cells with a labeling probe specific to a given RNA sequence. In addition, RNA size can be determined by size fraction using gel electrophoresis. Moreover, RNA transcription products can be visualized in situ by using quantitative fluorescent in situ hybridization (FISH) and a digital imaging microscope (Femino et al. (1998) Science 280: 585-90), which are applicable to the present invention.

When using reverse transcription PCR for gene expression analysis, the expression of a specific gene can be roughly quantified. Various isoforms of a single RNA transcription product can be also be detected and analyzed using the present method. For reverse transcription PCR, when the reaction is carried out using exon-specific primers, and amplification products other than the predicted product are detected, mRNA isoforms produced by alternative splicing can be identified by analyzing these products. See, for example, the method described in Pykett et al. (1994) Hum. Mol. Genet. 3: 559-64, for details. When a quick and rough analysis of expression pattern is demanded, the present method which uses the PCR of the present invention is particularly preferred, in terms of its high speed, high sensitivity, and simplicity.

The efficiency of gene expression screening can be improved by using a DNA chip. Here, a DNA chip refers to a miniature array, in which oligonucleotides, DNA clones, or such, are immobilized at a high density on a support surface such as glass. For example, in order to carry out multiple expression screening, cDNA clones for each gene of interest, or oligonucleotides specific to each gene, are immobilized on a chip to produce a microarray. Next, RNAs are prepared from dopamine-specific neuron precursor cells of the present invention, or cells differentiated, induced, or proliferated therefrom, and treated with reverse transcriptase to yield cDNAs. Next, the resulting cDNA sample is labeled with fluorescent tags or other tags, and then hybridized to the microarray. As a result, genes that are actively expressed in the cells have a higher percentage of the total labeled cDNA, while genes that are not significantly expressed have a lower percentage. Namely, the fluorescent signal intensity which represents hybridization between a labeled cDNA and a cDNA clone or an oligonucleotide on the chip, reflects the expression level of each sequence in the labeled cDNA, and thereby enables the quantification of gene expression.

In addition, multiple genes in dopaminergic neuron precursor cells of the present invention, or cells differentiated, induced, or proliferated therefrom, can be simultaneously analyzed by mRNA differential display, which involves reverse transcription PCR using degenerate PCR primers.

First, a modified oligo dT primer is prepared, in which one or two nucleotides at the 3' terminus in the poly A tail of a given mRNA have been altered. Then, a reverse transcription reaction is carried out using the total RNAs isolated from the precursor cells of the present invention, cells differentiated or proliferated therefrom, or control cells to be used for expression comparison (Liang et al. (1993) Nucleic Acids Res. 21: 3269-3275). If the altered nucleotide is a "G", then mRNA having a "C" immediately before the poly A tail can be selectively amplified. If the altered nucleotides are "CA", then mRNA having "TG" immediately before the poly A tail can be selectively amplified. Next, an arbitrary nucleotide sequence of about 10 nucleotides in length is prepared for use as a second primer, and a PCR amplification reaction is carried out using the modified oligo dT primer and this second primer. The amplification product is subjected to size fractionation by electrophoresis using a long polyacrylamide gel. By using such a method, cDNA derived from mRNA specifically expressed in either the cells of the present invention or the control cells can be detected as a band only present in the either sample that has been electrophoresed. This method can also be used to analyze expression of unidentified genes.

SAGE analysis does not require a special device for detection, and is one of the preferable analytical methods for simultaneously detecting the expression of a large number of transcription products. First, poly $A^+$ RNA is extracted from the dopaminergic neuron precursor cells of the present invention, or cells differentiated, induced, or proliferated therefrom, using standard methods. Next, the RNA is converted into cDNA using a biotinylated oligo (dT) primer, and then treated with a four-base recognizing restriction enzyme (Anchoring Enzyme: AE). Here, the AE-treated fragments contain a biotin group at their 3' terminus. Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. Here, the linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified once from the determination of the clone's nucleotide sequence and information on the sequence tags thus obtained.

Subtraction hybridization is frequently used for cloning a gene with different expression levels in various tissues or cells, and can also be used to clone a gene specifically expressed in dopaminergic neuron precursor cells of the present invention, or cells differentiated, induced, or proliferated therefrom. First, from the aforementioned cells of the present invention, a DNA sample of cells to be tested is prepared (hereinafter referred to as test DNA). Next, DNA of cells to be compared is prepared (hereinafter referred to as driver DNA). The test DNA and the driver DNA can also be used interchangeably. In any case, genes present in the test DNA but not present in the driver DNA are detected. Next, the prepared test DNA is mixed with a large excess of driver DNA, and denatured to form single-stranded DNA, followed by annealing. A specific sequence not present in the driver DNA can be isolated as double-stranded DNA comprising only the test DNA sequence by regulating the annealing conditions. See, Swaroop et al. (1991) Nucleic Acids Res. 19: 1954 and Yasunaga et al. (1999) Nature Genet. 21: 363-9, for further details on this method.

The RDA method is a method that uses PCR to selectively amplify a sequence of the test DNA that is not present in the driver DNA, and can be similarly used in the present invention like the other previously described methods. See, Lisitsyn (1995) Trends Genet. 11: 303-7 and Schutte et al. (1995) Proc. Natl. Acad. Sci. USA 92: 5950-4, for more details on the procedure.

Genes specific to dopaminergic neuron precursor cells, or cells differentiated, induced, or proliferated therefrom, are detected and isolated as described, and can be inserted into vectors or such, for sequence determination and expression analysis using the various known methods described above.

<Screening Using Precursor Cell Maturation as an Index>

The present invention provides a screening method that comprises a step of contacting a test substance with dopaminergic neuron precursor cells of the present invention, and a step of detecting differentiation or proliferation of the precursor cells resulting from that contact. Since compounds obtained by this screening method demonstrate a regulatory function in the differentiation, proliferation, and such, of dopaminergic neurons, they are considered useful as potential therapeutic candidates for diseases caused by defects in dopaminergic neurons.

Here, the "test substance" may be any type of compound, examples of which include the expression products of gene libraries, synthetic low molecular weight compound libraries, synthetic peptide libraries, antibodies, substances released by bacteria, cell (microbial, plant, or animal) extracts, cell (microbial, plant, or animal) culture supernatants, purified or partially purified polypeptides, marine organisms, plant or animal extracts, soil, random phage peptide display libraries, and such.

Cell differentiation and proliferation can be detected by comparing with the status of the cell in the absence of the test substance. Cell differentiation and proliferation may be detected by morphological observation under a microscope or by detection and quantification of substances produced in cells, such as dopamine.

<Analysis of 65B13 Expression Regulatory Region>

The present invention provides an expression regulatory region of 65B13. An expression regulatory region of the present invention can be cloned from genomic DNA by known methods using a polynucleotide of the present invention. For example, a method for establishing the transcriptional start site, such as the SI mapping method, is known and can be used in the present invention (Cell Engineering, Supplement 8, New Cell Engineering Experiment Protocol, Cancer Research Division, The Institute of Medical Science, The University of Tokyo ed., Shujunsha Publishing (1993) pp. 362-374). In general, the expression regulatory region of a gene can be cloned by screening a genomic DNA library, using a probe DNA comprising a 15-100 bp segment, and preferably a 30-50 bp segment, of the gene's 5' terminus (in the present invention, all or a portion of nucleotides 1 to 176 of SEQ ID NO: 1, or nucleotides 1 to 126 of SEQ ID NO: 2). A clone obtained in this manner contains a 5' non-coding region of 10 kbp or more, and is shortened or fragmented by exonuclease treatment, or such. Finally, the shortened sequence portion comprising a potential expression regulatory region is evaluated for its expression, strength, regulation, and such, using a reporter gene, thereby making it possible to determine the minimum unit required for maintaining the activity of the 65B13 expression regulatory region of the present invention.

Gene expression regulatory regions can be predicted using a program such as Neural Network (http://www.fruitfly.org./seg_tools/promoter.html; Reese et al., Biocomputing: Proceedings of the 1996 Pacific Symposium, Hunter and Klein ed., World Scientific Publishing Co., Singapore, (1996)). Moreover, a program for predicting the minimum unit required for the activity of an expression regulatory region is also known, (http://biosci.cbs.umn.edu./software/proscan/promoterscan.htm; Prestridge (1995) J. Mol. Biol. 249: 923-932), and can be used in the present invention.

The expression regulatory region of the 65B13 gene isolated in this manner can be used to produce a protein of interest specific for postmitotic dopaminergic neuron precursor cells in vivo.

<Ligand Identification>

The present invention provides ligands against the polypeptides of the present invention. The polypeptides of the present invention have a transmembrane domain, and thus are thought to exist embedded within the cell membrane in nature. These polypeptides are believed to be involved in neuron maturation because of their transient expression in dopaminergic neuron precursor cells immediately after cell cycle exit. Thus, potential ligands that may demonstrate an agonistic or antagonistic function towards a polypeptide of the present invention may be used for regulating the differentiation of dopaminergic neurons in vivo, ex vivo, and in vitro. In identifying a ligand for a polypeptide of the present invention, a polypeptide of the present invention and a candidate compound are first contacted and tested for the presence of binding. In this case, a polypeptide of the present invention can be used when immobilized on a support, or embedded in the cell membrane. There are no particular limitations on the candidate compounds, examples of which include expression products of gene libraries, natural substances derived from marine organisms, extracts of various types of cells, known compounds and peptides, natural substances derived from plants, body tissue extracts, microbial culture supernatants and peptide groups randomly produced by the phage display method (J. Mol. Biol. 222: 301-10 (1991)). In addition, the candidate compound may be labeled for detection of binding.

BRIEF DESCRIPTION OF THE DRAWINGS

FIG. 1 shows the cDNA sequence and the amino acid sequence of 65B13-a. The signal sequence and transmembrane domain are underlined.

FIG. 2 shows the cDNA sequence and the amino acid sequence of 65B13-a. The signal sequence and transmembrane domain are underlined. This drawing is a continuation of FIG. 1.

FIG. 3 shows the cDNA sequence and the amino acid sequence of 65B13-b. The signal sequence and transmembrane domain are underlined.

FIG. 4 shows the cDNA sequence and the amino acid sequence of 65B13-b. The signal sequence and transmembrane domain are underlined. This drawing is a continuation of FIG. 3.

FIG. 5 is comparison of the amino acid sequences of 65B13-a and 65B13-b.

FIG. 9 is a set of photographs showing the results of 65B13 mRNA expression analysis in the ventral midbrain region of E12.5 mice, and tyrosine hydroxylase (TH) mRNA expression analysis by in situ hybridization. A: 65B13, B: TH.

FIG. 14 is a set of graphs showing the flow-cytometric analysis results of detecting 65B13-expressing cells with a 65B13 monoclonal antibody in the (A) ventral midbrain region of E12.5 mouse embryo, and (B) cell populations comprising dopaminergic neuron precursor cells differentiated from ES cells in vitro.

BEST MODE FOR CARRYING OUT THE INVENTION

Figure 6:
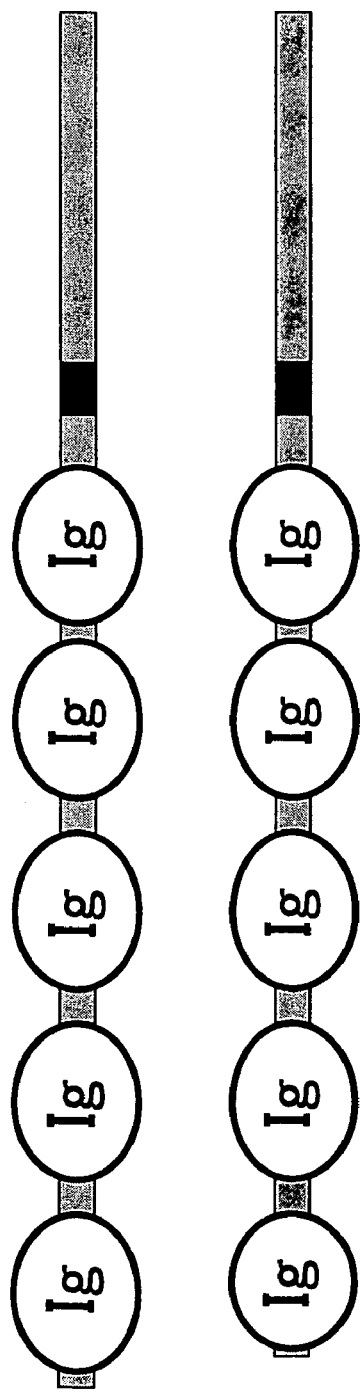
FIG. 6 is a schematic diagram of 65B13 structure. The shaded areas indicate the transmembrane domain, while Ig represents the Ig domain.

The present invention will be explained in more detail with reference to examples, but it is not to be construed as being limited thereto.

Example 1

Isolation and Sequence Analysis of a Gene Specific for Dopaminergic Neuron Precursor Cells To isolate a gene specific to dopaminergic neuron precursor cells, genes with differences in expression were amplified by the subtraction (N-RDA) method using RNA from ventral and dorsal midbrain of E12.5 mice, and sequences of the resulting genes were analyzed.

1. N-RDA Method

1-1. Adapter Preparation

The following oligonucleotides were annealed to each other, and prepared at 100 μM. (ad2: ad2S+ad2A, ad3: ad3S+ad3A, ad4: ad4S+ad4A, ad5: ad5S+ad5A, ad13: ad13S+ad13A)

```
ad2S:
cagctccacaacctacatcattccgt      (SEQ ID NO:11)

ad2A:
acggaatgatgt                    (SEQ ID NO:12)

ad3S:
gtccatcttctctctgagactctggt      (SEQ ID NO:13)

ad3A:
accagagtctca                    (SEQ ID NO:14)

ad4S:
ctgatgggtgtcttctgtgagtgtgt      (SEQ ID NO:15)

ad4A:
acacactcacag                    (SEQ ID NO:16)

ad5S:
ccagcatcgagaatcagtgtgacagt      (SEQ ID NO:17)

ad5A:
actgtcacactg                    (SEQ ID NO:18)

ad13S:
gtcgatgaacttcgactgtcgatcgt      (SEQ ID NO:19)

ad13A:
acgatcgacagt.                   (SEQ ID NO:20)
```

1-2. cDNA Synthesis

Total RNA was prepared from the ventral and dorsal midbrain regions of E12.5 mouse embryos (Japan SLC) using the RNeasy Mini Kit (Qiagen), and double-stranded cDNA is synthesized using a cDNA Synthesis Kit (Takara). After digestion with restriction enzyme RsaI, ad2 was added. The cDNA was amplified by a 5-minute incubation at 72° C., 15 PCR cycles of 30 seconds at 94° C., 30 seconds at 65° C., and 2 minutes at 72° C., and a final 2-minute incubation at 72° C. using ad2S as the primer. In all cases, N-RDA PCR was carried out using a reaction solution containing the following components.

10× ExTaq 5 μl
2.5 mM dNTP 4 μl
ExTaq 0.25 μl
100 μM primer 0.5 μl
cDNA 2 μl
Distilled water 38.25 μl

1-3. Driver Production

The ad2S amplified cDNA was further amplified by incubating at 94° C. for 2 minutes, and then performing five PCR cycles of 30 seconds at 94° C., 30 seconds at 65° C., and 2 minutes at 72° C., and a final 2-minute incubation at 72° C. The cDNA was purified using the Qiaquick PCR Purification Kit (Qiagen), and digested with RsaI. 3 μg was used for each round of subtraction.

1-4. Tester Production

The ad2S amplified cDNA was further amplified by incubating at 94° C. for 2 minutes, and then performing five PCR cycles of 30 seconds at 94° C., 30 seconds at 65° C., and 2 minutes at 72° C., and a final 2-minute incubation at 72° C. The cDNA was purified using the Qiaquick PCR Purification Kit (Qiagen), and digested with RsaI. ad3 was added to 60 ng of the RsaI-digested cDNA.

1-5. First Round of Subtraction

The tester and the driver produced in Sections 1-3 and 1-4 above were mixed, ethanol precipitated, and then dissolved in 1 μl of 1×PCR buffer. After a 5-minute incubation at 98° C., 1 μl of 1×PCR buffer+1M NaCl was added. After another 5 minutes of incubation at 98° C., the tester and the driver were hybridized at 68° C. for 16 hours.

With ad3 S as the primer, the hybridized cDNA was amplified by incubating at 72° C. for 5 minutes, and performing 10 cycles of 30 seconds at 94° C., 30 seconds at 65° C., and 2 minutes at 72° C. Next, the amplified cDNA was digested with the Mung Bean Nuclease (Takara) and purified using the Qiaquick PCR Purification Kit. Then, it was amplified by incubating at 94° C. for 2 minutes, and performing 13 PCR cycles of 30 seconds at 94° C., 30 seconds at 65° C., and 2 minutes at 72° C., and a final 2-minute incubation at 72° C.

1-6. Normalization

1 μl of 2×PCR buffer was added to 8 ng of the cDNA amplified in the first round of subtraction. After incubating at 98° C. for 5 minutes, 2 μl of 1×PCR buffer+1 M NaCl was added. After another 5 minutes of incubation at 98° C., the cDNA was hybridized at 68° C. for 16 hours.

The hybridized cDNA was digested with RsaI, and purified using the Qiaquick PCR Purification Kit. Then, it was amplified with ad3 S as the primer by incubating at 94° C. for 2 minutes, and performing 11 PCR cycles of 30 seconds at 94° C., 30 seconds at 65° C., and 2 minutes at 72° C., and a final 2-minute incubation at 72° C. The PCR product was then digested with RsaI, followed by the addition of ad4.

1-7. Second Round of Subtraction 20 ng of cDNA to which ad4 was added in Section 1-6 above was used as the tester and mixed with the driver of 1-3 above, and the same subtraction procedure used in Section 1-5 above was performed. Finally, ad5 was added to the cDNA following RsaI digestion.

1-8. Third Round of Subtraction 2 ng of cDNA to which ad5 was added in section 1-7 above was used as the tester and mixed with the driver of 1-3 above, and the same subtraction procedure used in section 1-5 above was carried out. Finally, ad13 was added to the RsaI-digested cDNA.

1-9. Fourth Round of Subtraction 2 ng of cDNA to which ad13 was added in section 1-8 above was used as the tester and mixed with the driver of 1-3 above, and the same subtraction procedure used in Section 1-5 above was carried out. The amplified cDNA was cloned into pCRII vector (Invitrogen), and its nucleotide sequence was analyzed using the ABI3100 sequence analyzer.

Next, RACE was carried out according to the method described below, using the 65B13 fragment sequence obtained by the N-RDA method.

2. RACE Method

Total RNA was prepared from the brain of a E12.5 mouse embryo by RNeasy Mini Kit (Qiagen) to prepare mRNA using the 1M ACS mRNA Isolation Kit (Miltenyi Biotec). A cDNA library was then prepared from the prepared mRNA using the Superscript Choice System (Invitrogen) and pCRII vector (Invitrogen). Plasmid DNA was then prepared from this cDNA library. PCR was carried out using the following primers:

```
TAU2:     GGCTTTACACTTTATGCTTCCGGCTC (SEQ ID NO:21)

TAU4:     CAGCTATGACCATGATTACGCCAAGC (SEQ ID NO:22)

TAD3:     AGGCGATTAAGTTGGGTAACGCCAGG (SEQ ID NO:23)

TAD4:     CCAGTCACGACGTTGTAAAACGACGG (SEQ ID NO:24)

65B13 F1: CTTCCCGTATGCTACCTTGTCTCCAC (SEQ ID NO:25)

65B13 F2: TCCATCTCTCCAAGTGAAGGGTCTTG (SEQ ID NO:26)

65B13 R1: CCAACAGTCCTGCATGCTTGTAATGA (SEQ ID NO:27)

65B13 R2: TCCTTCAATGTTCAGTTTTGGAGGGG (SEQ ID NO:28)
```

The PCR conditions are indicated below.
1 st Round PCR:
10× ExTaq 2 µl
2.5 mM dNTP 1.6 µl
ExTaq 0.1 µl
100 µM TAU2 or TAD3 0.04 µl
100 µM 65B13 F1 or R1 0.2 µl
cDNA (10 ng/µl) 1 µl
Distilled water 15.06 µl After incubating at 94° C. for 5 minutes, 25 cycles of 30 seconds at 94° C., 30 seconds at 65° C., and 5 minutes at 72° C., and a final 2-minute incubation at 72° C. were carried out. Next, the second round of PCR was carried out using the 100-fold-diluted product obtained from first round PCR. Conditions for the second round PCR are as shown below.

2nd Round of PCR:
10× ExTaq 5 µl
2.5 mM dNTP 4 µL
ExTaq 0.25 µl
100 µM TAU4 or TAD4 0.1 µl
100 µM 65B13 F2 or R2 0.5 µl
1/100 1st PCR product 1 µl
Distilled water 15.06 µl After incubating for 5 minutes at 94° C., 25 cycles of 30 seconds at 94° C., 30 seconds at 65° C., and 5 minutes at 72° C., and a final 2-minute incubation at 72° C. were carried out. The amplified cDNA fragment was cloned into the pCRII vector and its sequence was analyzed using the ABI3100 sequence analyzer.

The nucleotide sequences of the resulting two genes of 65B13-a and 65B13-b are shown as SEQ ID NO: 1 (FIGS. 1 and 2) and SEQ ID NO: 2 (FIGS. 3 and 4). The coding region of 65B13-a begins at the 177th "A" of SEQ ID NO: 1 and ends with the stop codon at nucleotides 2278 to 2280, yielding a protein comprising 700 amino acids. The 17 amino acid residues encoded by the sequence of nucleotides 177 to 228 is the signal sequence. The 17 amino acid residues encoded by the sequence of nucleotides 1717 to 1767 is the transmembrane domain. In contrast, the coding region of 65B13-b begins at the 127th "A" of SEQ ID NO: 2 and ends at the stop codon of nucleotides 2077 to 2079, yielding a protein comprising 650 amino acids. The 17 amino acid residues encoded by the sequence of nucleotides 127 to 177 is the signal sequence, and the 17 amino acid residues encoded by the sequence of nucleotides 1516 to 1566 is the transmembrane domain. The amino acid sequences encoded by the 65B13-a and 65B13-b genes are shown in SEQ ID NOs: 3 and 4. As shown in FIG. 5, a comparison of the amino acid sequences encoded by both genes revealed that 65B13-a and 65B13-b are isoforms that have resulted from alternative splicing, and that 65B13-b lacks 50 amino acids at the N-terminus compared to 65B13-a. Based on the homology search results, the proteins encoded by the 65B13 genes are believed to be single transmembrane proteins with five Ig domains as shown in FIG. 6.

Example 2

Expression Analysis of the 65B13 Genes

Next, an expression analysis of these genes by in situ hybridization was carried out according to the following protocol.

First, E12.5 mouse embryos were embedded in O.C.T., and fresh frozen sections of 16 µm thickness were prepared. After drying on a slide glass, the sections were fixed in 4% PFA at room temperature for 30 minutes. After washing with PBS, hybridization was carried out at 65° C. for 40 hours (1 µg/ml DIG-labeled RNA probe, 50% formamide, 5×SSC, 1% SDS, 50 µg/ml yeast RNA, 50 µg/ml Heparin); Subsequently, the sections were washed at 65° C. (50% formamide, 5×SSC, 1% SDS) and then treated with RNase (5 µg/ml RNase) at room temperature for 5 minutes. After washing with 0.2×SSC at 65° C. and washing with 1×TBST at room temperature, blocking was carried out (Blocking reagent: Roche). The sections were then reacted with alkaline phosphatase-labeled anti-DIG antibody (DAKO), washed (1×TBST, 2 mM Levamisole), and color developed using NBT/BCIP (DAKO) as the substrate.

Figure 7:
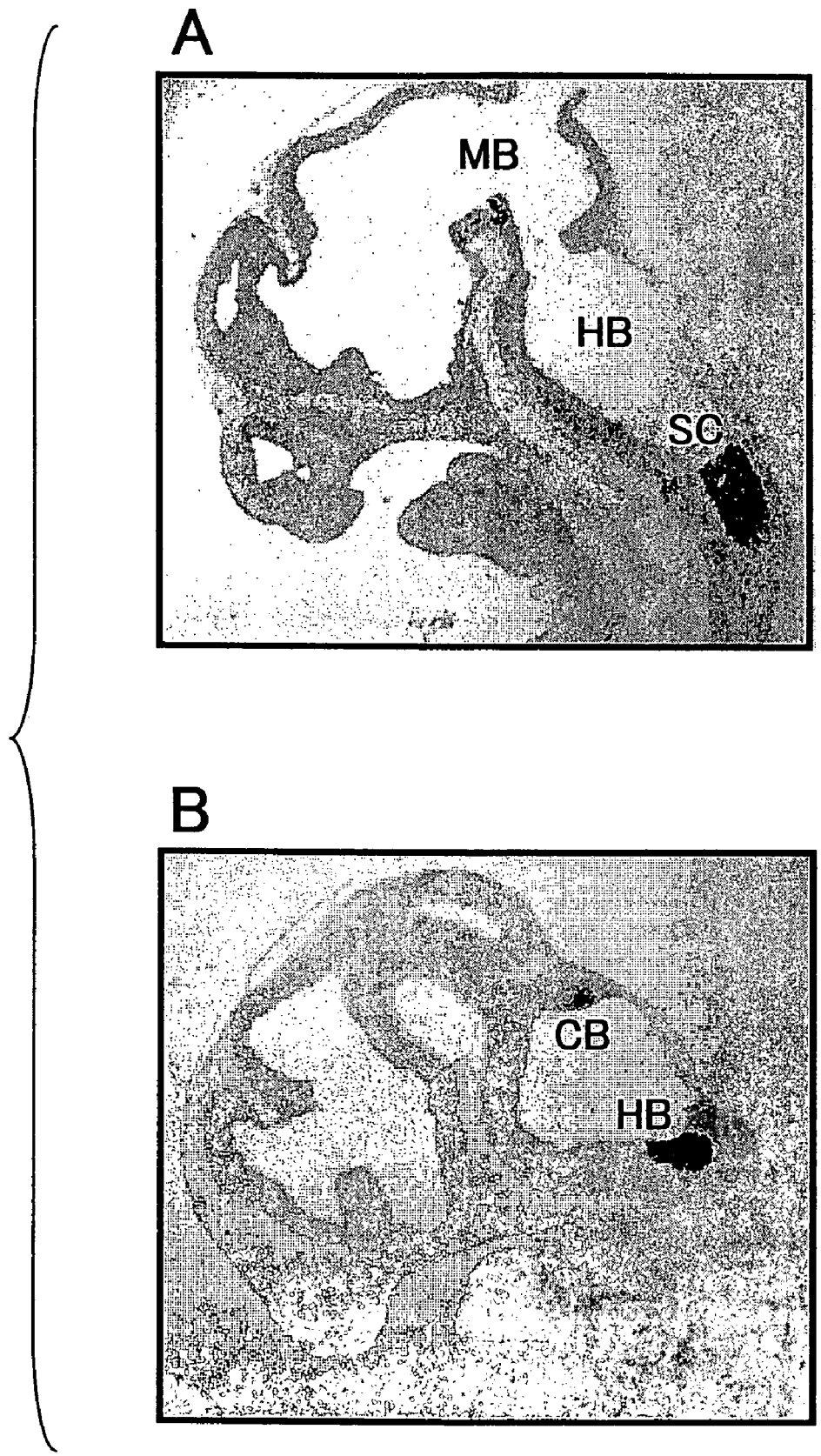
FIG. 7 is a set of photographs showing the results of 65B13 mRNA expression analysis in E12.5 mouse brain by in situ hybridization. A: Sagittal cross-section, B: Parasagittal cross-section, HB: Hindbrain, MB: Midbrain, SC: Spinal cord, CB: Cerebellar primordium.
Figure 8:
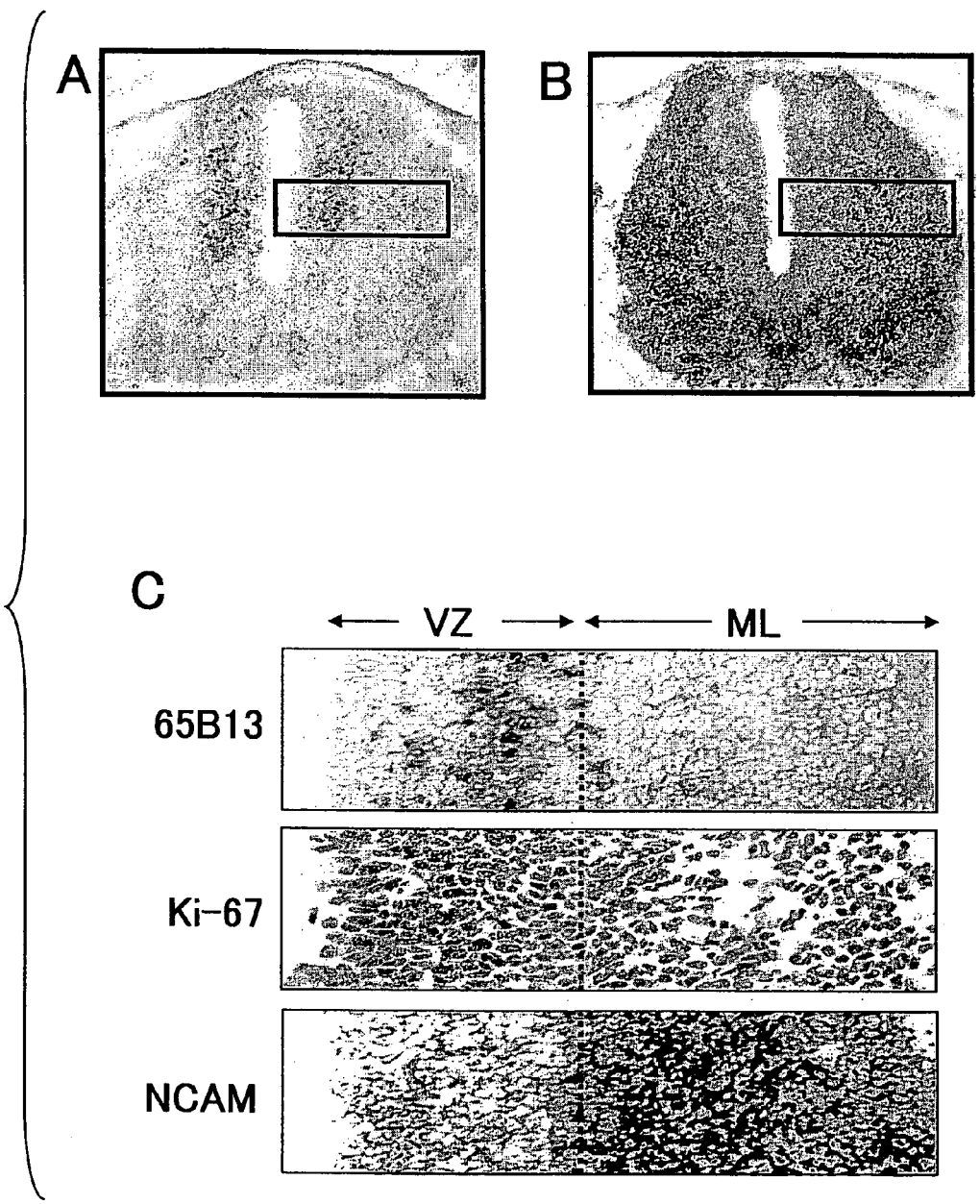
FIG. 8 is a set of photographs showing the results of 65B13 mRNA expression analysis in E12.5 mouse spinal cord by in situ hybridization. A: 65B13, B: NCAM, C: Comparison of the expression regions of 65B13, Ki67, and NCAM (shown as enlarged pictures of framed regions in A and B).

The expression analysis results of these genes by in situ hybridization showed that 65B13 is expressed in the ventral midbrain region, cerebellar primordium, hindbrain, and spinal cord, at the stage E12.5 which corresponds to the time of dopaminergic neuron development (FIG. 7). 65B13 expression in the spinal cord was further compared with those of the growth marker Ki67 and the maturation marker NCAM. In the ventricular zone (VZ) where Ki67-positive neural progenitors proliferate, 65B13 was expressed in some cells. In contrast, 65B13 expression was not observed in the mantle layer (ML), where matured NCAM-positive precursors that have exited from the cell cycle exit (FIG. 8). Similarly in zones outside the spinal cord, expression was observed in some cells within VZ. According to these expression patterns, 65B13 was thought to be expressed transiently in neural precursor cells immediately after cell cycle exit.

Figure 10:
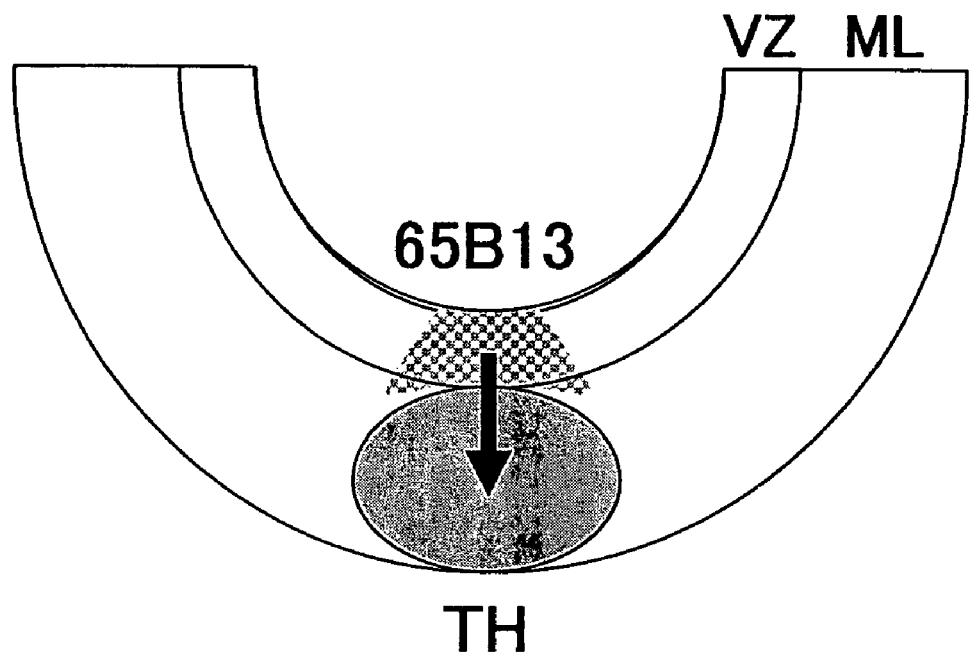
FIG. 10 is a schematic diagram showing the expression pattern of 65B13 in the midbrain.
Figure 11:
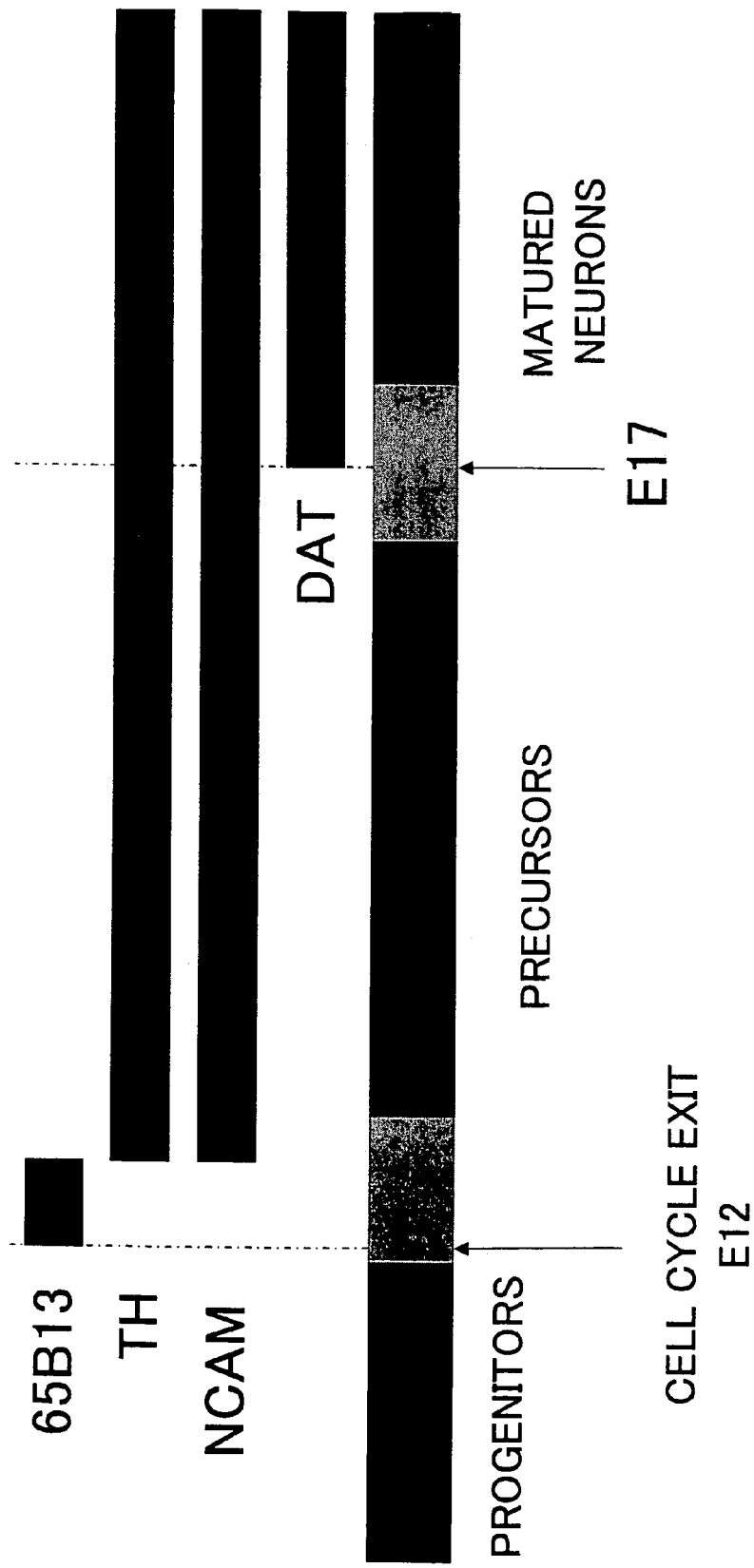
FIG. 11 is a schematic diagram showing the 65B13 expression pattern over time.
Figure 12:
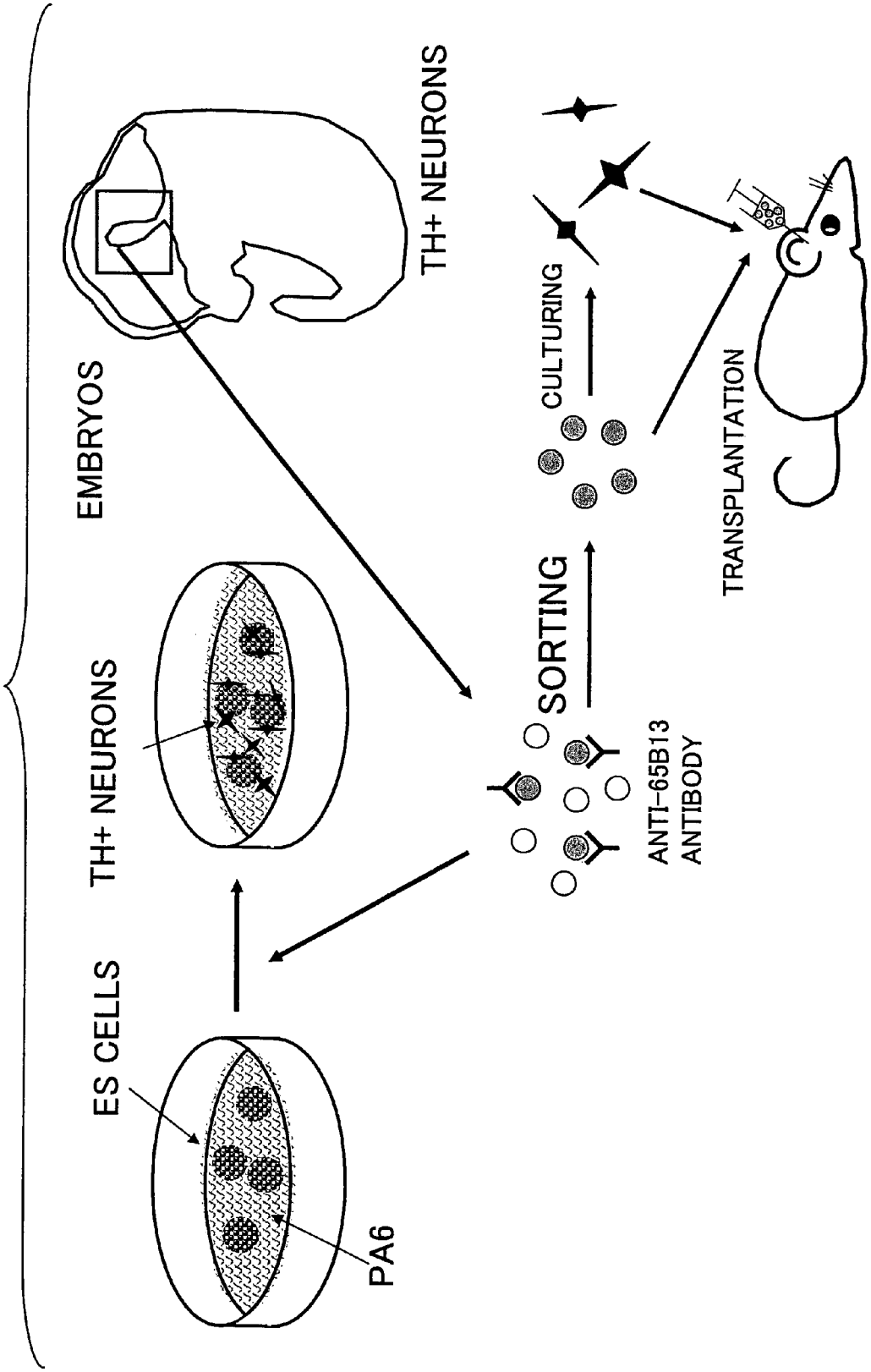
FIG. 12 is a schematic diagram demonstrating the methods for separating and utilizing dopaminergic neuron precursor cells using an anti-65B13 antibody.

In the midbrain, expression was only observed in the most ventral region of the ventricular zone. Since tyrosine hydroxylase (TH), a marker gene for dopaminergic neurons, is only expressed in the ML, a comparison of the TH expression and the 65B13 expression showed that both were not expressed in the same cells, however, their expression regions along the dorsal-ventral axis were completely overlapped (FIG. 9). In general, nerve cells present in neural tubes are known to proliferate in the VZ, stop cell division with the commencement of differentiation, and then mature after migrating to the ML, which is just outside of the VZ. Thus, progenitors of dopaminergic neurons are believed to proliferate in the VZ adjacent to the TH expression zone, and express TH after having migrated to the outside following the cell cycle exit. Since this VZ region where these progenitors proliferate overlaps with the 65B13 expression region, 65B13 is thought to express specifically and transiently in dopaminergic neuron precursor cells in the midbrain immediately after cell cycle exit (FIGS. 10 and 11).

Example 3

Expression Analysis of the 65B13 Proteins

Next, a portion of the 65B13 gene sequence that encodes the extracellular region was used to generate an anti-65B13 antibody to be used for expression analysis by immunohistochemical staining.

First, a partial sequence of the 65B13 gene that encodes the extracellular region was introduced into 293E cells, and the extracellular region of the 65B13 protein was expressed and recovered. After immunizing hamsters with the recovered protein, lymphocytes were extracted and fused with myeloma cells. The fused cells were then transplanted into the abdominal cavities of mice, ascites was obtained, and an anti-65B13 monoclonal antibody was purified. Next, E12.5 mouse embryos were fixed in 4% PFA/PBS(-) at 4° C. for 2 hours, and then stood overnight at 4° C. in 20% sucrose/PBS(-), followed by O.C.T. embedding. Sections of 12 um thickness were produced. After affixing to slide glasses, the sections were dried for 30 minutes at room temperature and then re-moistened with PBS(-). Subsequently, blocking (Block Ace) was carried out at room temperature for 20 minutes. The tissue section glasses were incubated with the generated anti-65B13 monoclonal antibody (10 ug/ml, 2.5% Block Ace/PBS), anti-TH antibody (Chemicon, 0.7 ug/ml, 2.5% Block Ace/PBS), and anti-Nurr1 antibody (Santa Cruz, 4 ug/ml, 2.5% Block Ace/PBS) for 1 hour at room temperature, and overnight at 4° C. The tissue section glasses were then washed four times with 0.1% Triton X-100/PBS(-) at room temperature for 10 minutes each, and incubated with Cy3-labeled anti-hamster IgG antibody, FITC-labeled anti-rabbit IgG antibody, and Cy5-labeled anti-mouse IgG antibody (Jackson, 10 ug/ml, 2.5% Block Ace) at room temperature for 1 hour. The glasses were washed in the same manner, followed by an additional 10-minute wash with PBS(-) at room temperature, and were then embedded.

Figure 13:
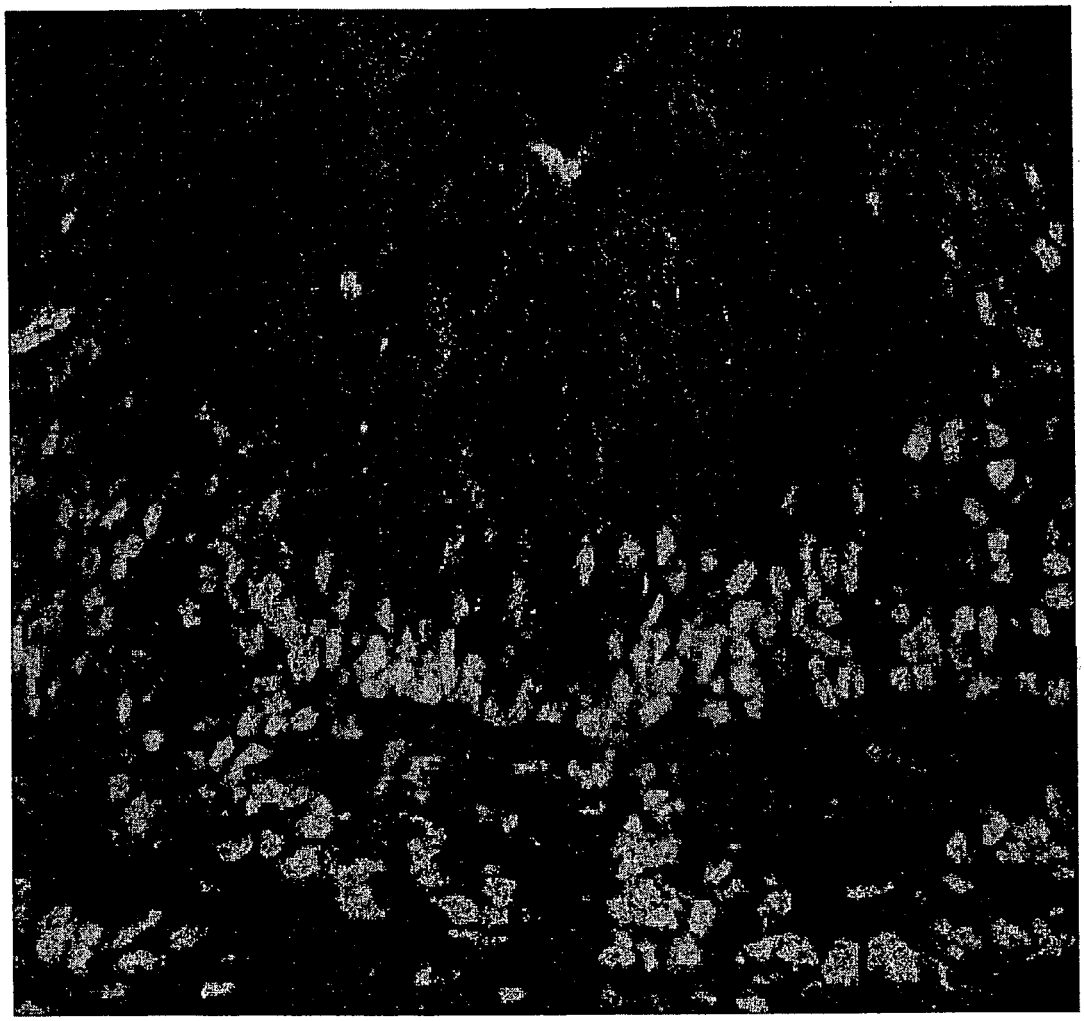
FIG. 13 is a photograph showing the expression analysis results of 65B13 (Cy3), Nurr1 (FITC), and TH (Cy5) proteins, by the immunofluorescent staining method using antibodies against each protein.

Similarly to the expression analysis by in situ hybridization, expression analysis by immunohistochemical staining using the produced anti-65B13 monoclonal antibody showed that 65B13 was expressed in the ventral midbrain region at E12.5, which corresponds to the time of dopaminergic neuron development (FIG. 13). A comparison of the 65B13 protein expression with those of the dopaminergic neuron markers TH and Nurr1 protein, revealed that 65B13 protein was expressed in the VZ side of the ventral-most region of the midbrain where TH and Nurr1 protein are expressed. Thus, 65B13 protein was thought to express in dopaminergic neuron precursor cells.

Example 4

Detection of 65B13-Expressing Cells by Flow Cytometry

Next, cells that express 65B13 were detected by flow cytometry using an anti-65B13 monoclonal antibody.

First, the ventral midbrain region excised from E12.5 mouse embryos, or cell populations comprising dopaminergic neuron precursor cells that have differentiated from ES cells in vitro, were dispersed in a cell dissociation buffer (Invitrogen). Then, the samples were stained for 20 minutes at 4° C. with an anti-65B13 monoclonal antibody (10 ug/ml, 1% fetal calf serum, 1 mM EDTA/PBS), without prior fixation or permeation. Subsequently, the samples were washed three times with 1% fetal calf serum and 1 mM EDTA/PBS(-) at 4° C. for 3 minutes, stained with PE-labeled anti-hamster IgG antibody (Pharmingen, 4 ug/ml, 1% fetal calf serum, 1 mM EDTA/PBS) at 4° C. for 20 minutes, and then washed in the same manner. The 65B13-expressing cells were then detected by flow cytometry.

Populations of cells expressing the 65B13 proteins were detected by flow cytometry using the generated anti-65B13 monoclonal antibody (FIG. 14). Since 65B13-expressing cells can be detected without fixation or permeation, 65B13-expressing cells are believed to be separable as viable cells, by using a flow cytometer equipped with a cell sorter. Since 65B13 protein is thought to express in dopaminergic neuron precursor cells, 65B13 is believed to be useful for the separation of dopaminergic neuron precursor cells.

INDUSTRIAL APPLICABILITY

A novel 65B13 gene expressed specifically and transiently in dopaminergic neuron precursor cells immediately after cell cycle exit was obtained according to the present invention. The cellular expression of 65B13 can be used as an indicator in selecting suitable cells to be used in transplant therapy for neurodegenerative diseases such as Parkinson's disease, in terms of their safety, survival rate, and network formation ability. In addition, since dopaminergic neuron precursor cells immediately after cell cycle exit are selectively obtained, they can be easily differentiated into an appropriate state in vitro when used in therapy that require mature cells. Moreover, dopaminergic neuron precursor cells obtained using the genes of the present invention can also be used to isolate genes specifically expressed in these cells. The cells are also thought to be useful in developing pharmaceuticals for neurodegenerative diseases such as Parkinson's disease. Since dopaminergic neuron precursor cells immediately after cell cycle exit are precursor cells involved in early neuron formation, they are useful in elucidating the neuron maturation process, namely, identifying various factors involved in the maturation process. Elucidation of these factors is expected to contribute greatly to the treatment of neurodegenerative diseases. Moreover, maturation of these cells can be used as an index for screening substances that may regulate (inhibit or promote) the maturation process.

The invention claimed is:

1. A method of selecting a dopaminergic neuron precursor cell, wherein the method comprises:
   contacting a cell sample comprising ventral midbrain cells with an antibody that binds to a polypeptide
   encoded by a polynucleotide comprising a sequence selected from
   (i) a nucleotide sequence comprising nucleotides 178 to 2280 of SEQ ID NO: 1 or nucleotides 127 to 2079 of SEQ ID NO: 2;
   (ii) a nucleotide sequence encoding the amino acid sequence of SEQ ID NO: 3 or 4;
   (iii) a nucleotide encoding residues 18-700 of SEQ ID NO:3 or residues 18-650 of SEQ ID NO:4
   (iv) a nucleotide sequence encoding an amino acid sequence which has 80% or more identity with the amino acid sequence of SEQ ID NO: 3 or 4; and or
   a fragment of said polypeptide comprising at least eight amino acid residues; and
   isolating the dopaminergic neuron precursor cell, wherein the dopaminergic neuron precursor cell has bound to the antibody.

2. The method according to claim 1, wherein the method comprises the step of separating the dopaminergic neuron precursor cell by flow cytometry.

3. The method according to claim 1, wherein the antibody binds to an extracellular region of the polypeptide.

4. The method according to claim 1, wherein the nucleotide sequence of (iv) encodes a protein having the amino acid sequence having 95% or more identity with the amino acid sequence of SEQ ID NO: 3 or 4.

5. The method according to claim 1 wherein the polypeptide is encoded by a polynucleotide comprising a sequence selected from the group consisting of:
   (i) a nucleotide sequence comprising nucleotides 178 to 2280 of SEQ ID NO: 1 or nucleotides 127 to 2079 of SEQ ID NO: 2;
   (ii) a nucleotide sequence encoding the amino acid sequence of SEQ ID NO: 3 or 4; and
   (iii) a nucleotide encoding residues 18-700 of SEQ ID NO:3 or residues 18-650 of SEQ ID NO:4.

6. A method of producing a cell population comprising dopaminergic neuron precursor cells, wherein the method comprises contacting a cell sample comprising ventral midbrain cells with an antibody that binds to a polypeptide
   encoded by a polynucleotide comprising a sequence selected from
   (i) a nucleotide sequence comprising nucleotides 178 to 2280 of SEQ ID NO: 1 or nucleotides 127 to 2079 of SEQ ID NO: 2;
   (ii) a nucleotide sequence encoding the amino acid sequence of SEQ ID NO: 3 or 4;
   (iii) a nucleotide encoding residues 18-700 of SEQ ID NO:3 or residues 18-650 of SEQ ID NO:4
   (iv) a nucleotide sequence encoding an amino acid sequence which has 80% or more identity with the amino acid sequence of SEQ ID NO: 3 or 4; and or
   a fragment of said polypeptide comprising at least eight amino acid residues; and
   isolating the cell population comprising dopaminergic neuron precursor cells, wherein the dopaminergic neuron precursor cells have bound to the antibody.

7. The method according to claim 6, wherein the method comprises the step of separating the dopaminergic neuron precursor cell by flow cytometry.

8. The method according to claim 6, wherein the antibody binds to an extracellular region of the polypeptide.

9. The method according to claim 6, wherein the nucleotide sequence of (iv) encodes a protein having the amino acid sequence having 95% or more identity with the amino acid sequence of SEQ ID NO: 3 or 4.

10. The method according to claim 6, wherein the polypeptide is encoded by a polynucleotide comprising a sequence selected from the group consisting of:
    (i) a nucleotide sequence comprising nucleotides 178 to 2280 of SEQ ED NO: 1 or nucleotides 127 to 2079 of SEQ ID NO: 2;
    (ii) a nucleotide sequence encoding the amino acid sequence of SEQ ID NO: 3 or 4; and
    (iii) a nucleotide encoding residues 18-700 of SEQ ID NO:3 or residues 18-650 of SEQ ID NO:4.

* * * * *

UNITED STATES PATENT AND TRADEMARK OFFICE
CERTIFICATE OF CORRECTION

| | | |
|---|---|---|
| PATENT NO. | : 7,622,270 B2 | Page 1 of 1 |
| APPLICATION NO. | : 10/532264 | |
| DATED | : November 24, 2009 | |
| INVENTOR(S) | : Nakagawa et al. | |

It is certified that error appears in the above-identified patent and that said Letters Patent is hereby corrected as shown below:

At column 1, line 65, please delete "Steroli's" and insert --Sertoli's--.

At column 63, Claim 1, (iv), lines 25-27, please delete "or a fragment of said polypeptide comprising at least eight amino acid residues; and".

At column 64, claim 6, (iv), lines 24-26, please delete "or a fragment of said polypeptide comprising at least eight amino acid residues; and".

At column 63, claim 10, (i), line 43, please delete "ED" and insert --ID--.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,622,270 B2 Page 1 of 1
APPLICATION NO. : 10/532264
DATED : November 24, 2009
INVENTOR(S) : Nakagawa et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 319 days Delete the phrase "by 319 days" and insert -- by 900 days --

Signed and Sealed this

Seventh Day of September, 2010

David J. Kappos
*Director of the United States Patent and Trademark Office*

SEQUENCE LISTING

<160> NUMBER OF SEQ ID NOS: 28

<210> SEQ ID NO 1
<211> LENGTH: 2876

<212> TYPE: DNA
<213> ORGANISM: Mus musculus

<400> SEQUENCE: 1

```
gatgagccag atttcgggga ctctgggcca gacataaaat cttccagccc ggagagaatt     60
gtgtgcagag agggctcca gtccagcgtg gtgtgagagg cgtgctatca agaaagaagt    120
tggagggaa ccagtgcaac cctaactcta cgagatcttg gggtacacac actcgggatg    180
ctggcctccg ccctcctcgt tttcctttgc tgtttcaaag gacatgcagg ctcatcgccc    240
catttcctac aacagccaga ggacatggtg gtgctgttgg gggaggaagc ccggctgccc    300
tgcgctctgg gcgcgtacag ggggctcgtg cagtggacta aggatgggct ggctctaggg    360
ggcgaaagag accttccagg gtggtcccgg tactggatat cggggaattc agccagtggc    420
cagcatgacc tccacattaa gcctgtggaa ttgaagatg aggcatcgta tgagtgccag    480
gcttcgcaag caggtctccg atcacgacca gcccaactgc acgtgatggt cccccagaa    540
gctccccagg tactaggcgg cccctctgtg tctctggttg ctggagttcc tggaaatctg    600
acctgtcgga gtcgtgggga ttcccgacct gcccctgaac tactgtggtt ccagatgggg    660
atccggctgg atgcgagcag cttccaccag accacgctga aggacaaggc cactggaaca    720
gtggaaaaca ccttattcct gaccccttcc agtcatgatg atggcgccac cttgatctgc    780
agagcgcgaa gccaggccct gcccacaggg agggacacag ctgttacact gagccttcag    840
tatcccccaa tggtgactct gtctgctgag ccccagactg tgcaggaggg agagaaggtg    900
actttcctgt gtcaagccac tgcccagcct cctgtcactg gctacaggtg ggcgaagggg    960
ggatccccgg tgctcgggc acgtgggcca aggttggagg tcgttgcaga tgccactttc   1020
ctgactgagc cggtgtcctg cgaggtcagc aacgcggtcg gaagcgccaa ccgcagcacg   1080
gcgctggaag tgttgtatgg acccattctg caggcaaaac ctaagtccgt gtccgtggac   1140
gtggggaaag atgcctcctt cagctgtgtc tggcgcggga acccacttcc acggataacc   1200
tggacccgca tgggtggctc tcaggtgctg agctccgggc ccacgctgcg gcttccgtcc   1260
gtggcactgg aggatgcggg cgactatgta tgcagggctg agccgaggag aacgggtctg   1320
ggaggcggca aagcgcaggc gaggctgact gtgaacgcac cccctgtagt gacagccctg   1380
caacctgcac cagcctttct gaggggtcct gctcgcctcc agtgtgtggt gtttgcctcc   1440
cctgccccag actcggtggt ttggtcttgg gacgagggct tcttggaggc aggctcactg   1500
ggcaggttcc tagtggaagc cttcccagcc ccggaagtgg agggggaca gggccctggc   1560
cttatttctg tgctacacat ttccggaacc caggagtccg actttaccac cggcttcaac   1620
tgcagtgccc gcaaccggct aggagaggga cgagtccaga tccacttggg ccgtagagat   1680
ttgctgccta ctgtccggat tgtggctggt gcagcatctg cagccacctc tctccttatg   1740
gtcatcactg gagtggtcct ctgctgctgg cgccatggcc ctctctctaa gcaaaagaac   1800
ttggtccgga tcccaggaag cagcgagggt tccagttcac gtggccctga ggaggagaca   1860
ggcagcagtg aggaccgggg tcccattgtg cacaccgacc acagtgattt ggttcttgag   1920
gaaaaagagg ctctggagac aaaggatcca accaacggtt actacaaggt tcgaggggtc   1980
agtgtgagcc ttagccttgg ggaagctcct ggaggaggcc tcttcttgcc accgccctct   2040
ccgatcggtc tcccagggac tcctacttac tatgacttca agccacatct ggacttagtc   2100
cctccctgca gactgtacag agcgagggca ggttatctta ccaccccca tccccgtgcc   2160
ttcaccagct acatgaaacc cacatccttt ggacccccag atttgagctc tggaactccc   2220
```

| | |
|---|---|
| cccttcccgt atgctacctt gtctccaccc agccaccagc gtctccagac tcatgtgtga | 2280 |
| atccatctct ccaagtgaag ggtcttggaa tcttctgttt gccatatagt gtgttgtcca | 2340 |
| gatttctggg gagtcagaac aagttgatga ccaacccctc caaaactgaa cattgaagga | 2400 |
| gggaaagatc attacaagca tcaggactgt tggtgtacac tcagttcagc caaagtggat | 2460 |
| tctccaagtg ggagcaatat ggccgctttc ccatgagaaa gacattcaag atggtgacta | 2520 |
| aatgactaaa tactttgcag agggacaaag atgggaacta gggatacgga tggaagtagt | 2580 |
| agagaagata tatgaccatc tgcatcaaga ggaaggataa catatgacaa atcaagatga | 2640 |
| aagaaataat ccaccccacc cccaccgcgt cctggccaat aagtatagcc tacatggctg | 2700 |
| ttcattatct gggaaccaaa atggccacta tcttgactcc ttccttaaag atacagaaag | 2760 |
| aattgaatcc aaggaatggg gtagggtgga aatagaagaa atgaagggga ctcttgggct | 2820 |
| aagaatactt atgtttaata ataaaagggg gaggcaaaga tgcaaaaaaa aaaaaa | 2876 |

<210> SEQ ID NO 2
<211> LENGTH: 2243
<212> TYPE: DNA
<213> ORGANISM: Mus musculus

<400> SEQUENCE: 2

| | |
|---|---|
| gagagaattg tgtgcagaga gaggctccag tccagcgtgg tgtgagaggc gtgctatcaa | 60 |
| gaaagaagtt ggaggggaac cagtgcaacc ctaactctac gagatcttgg ggtacacaca | 120 |
| ctcgggatgc tggcctccgc cctcctcgtt ttcctttgct gtttcaaagg acatgcaggg | 180 |
| tggtcccggt actggatatc ggggaattca gccagtggcc agcatgacct ccacattaag | 240 |
| cctgtggaat tggaagatga ggcatcgtat gagtgccagg cttcgcaagc aggtctccga | 300 |
| tcacgaccag cccaactgca cgtgatggtc cccccagaag ctccccaggt actaggcggc | 360 |
| ccctctgtgt ctctggttgc tggagttcct ggaaatctga cctgtcggag tcgtggggat | 420 |
| tcccgacctg cccctgaact actgtggttc cgagatggga tccggctgga tgcgagcagc | 480 |
| ttccaccaga ccacgctgaa ggacaaggcc actggaacag tggaaaacac cttattcctg | 540 |
| accccttcca gtcatgatga tggcgccacc ttgatctgca gagcgcgaag ccaggccctg | 600 |
| cccacaggga gggacacagc tgttacactg agccttcagt atcccccaat ggtgactctg | 660 |
| tctgctgagc cccagactgt gcaggaggga gagaaggtga cttttcctgtg tcaagccact | 720 |
| gcccagcctc ctgtcactgg ctacaggtgg gcgaagggg gatccccggt gctcggggca | 780 |
| cgtgggccaa ggttggaggt cgttgcagat gccacttttcc tgactgagcc ggtgtcctgc | 840 |
| gaggtcagca cgcggtcgg aagcgccaac cgcagcacgg cgctggaagt gttgtatgga | 900 |
| cccattctgc aggcaaaacc taagtccgtg tccgtggacg tggggaaaga tgcctccttc | 960 |
| agctgtgtct ggcgcgggaa cccacttcca cggataacct ggaccgcat gggtggctct | 1020 |
| caggtgctga gctccgggcc cacgctgcgg cttccgtccg tggcactgga ggatgcgggc | 1080 |
| gactatgtat gcagggctga gccgaggaga acgggtctgg gaggcggcaa agcgcaggcg | 1140 |
| aggctgactg tgaacgcacc ccctgtagtg acagccctgc aacctgcacc agcctttctg | 1200 |
| aggggtcctg ctcgcctcca gtgtgtggtg tttgcctccc ctgccccaga ctcggtggtt | 1260 |
| tggtcttggg acgagggctt cttggaggca ggctcactgg gcaggttcct agtgaagcc | 1320 |
| ttcccagccc cggaagtgga gggggacag ggccctggcc ttatttctgt gctacacatt | 1380 |
| tccggaaccc aggagtccga ctttaccacc ggcttcaact gcagtgcccg caaccggcta | 1440 |
| ggagagggac gagtccagat ccacttgggc cgtagagatt tgctgcctac tgtccggatt | 1500 |

-continued

```
gtggctggtg cagcatctgc agccacctct ctccttatgg tcatcactgg agtggtcctc    1560
tgctgctggc gccatggctc tctctctaag caaaagaact tggtccggat cccaggaagc    1620
agcgagggtt ccagttcacg tggccctgag gaggagacag gcagcagtga ggaccggggt    1680
cccattgtgc acaccgacca cagtgatttg gttcttgagg aaaagaggc tctggagaca     1740 aaggatccaa ccaacggtta ctacaaggtt cgagggtca gtgtgagcct tagccttggg     1800
gaagctcctg gaggaggcct cttcttgcca ccgccctctc cgatcggtct cccagggact    1860
cctacttact atgacttcaa gccacatcag gacttagtcc ctccctgcag actgtacaga    1920
gcgagggcag gttatcttac cacccccat ccccgtgcct tcaccagcta catgaaaccc     1980
acatcctttg accccagga tttgagctct ggaactcccc ccttcccgta tgctaccttg     2040
tctccaccca gccaccagcg tctccagact catgtgtgaa tccatctctc caagtgaagg    2100
gtcttggaat cttctgtttg ccatatagtg tgttgtccag atttctgggg agtcagaaca    2160
agttgatgac caacccctcc aaaactgaac attgaaggag ggaaagatca ttacaagcat    2220
caggactgtt ggtgtacact cag                                            2243
```

<210> SEQ ID NO 3
<211> LENGTH: 700
<212> TYPE: PRT
<213> ORGANISM: Mus musculus

<400> SEQUENCE: 3

```
Met Leu Ala Ser Ala Leu Leu Val Phe Leu Cys Cys Phe Lys Gly His
  1               5                  10                  15

Ala Gly Ser Ser Pro His Phe Leu Gln Gln Pro Glu Asp Met Val Val
             20                  25                  30

Leu Leu Gly Glu Glu Ala Arg Leu Pro Cys Ala Leu Gly Ala Tyr Arg
         35                  40                  45

Gly Leu Val Gln Trp Thr Lys Asp Gly Leu Ala Leu Gly Gly Glu Arg
     50                  55                  60

Asp Leu Pro Gly Trp Ser Arg Tyr Trp Ile Ser Gly Asn Ser Ala Ser
 65                  70                  75                  80

Gly Gln His Asp Leu His Ile Lys Pro Val Glu Leu Glu Asp Glu Ala
                 85                  90                  95

Ser Tyr Glu Cys Gln Ala Ser Gln Ala Gly Leu Arg Ser Arg Pro Ala
            100                 105                 110

Gln Leu His Val Met Val Pro Pro Glu Ala Pro Gln Val Leu Gly Gly
        115                 120                 125

Pro Ser Val Ser Leu Val Ala Gly Val Pro Gly Asn Leu Thr Cys Arg
    130                 135                 140

Ser Arg Gly Asp Ser Arg Pro Ala Pro Glu Leu Leu Trp Phe Arg Asp
145                 150                 155                 160

Gly Ile Arg Leu Asp Ala Ser Ser Phe His Gln Thr Thr Leu Lys Asp
                165                 170                 175

Lys Ala Thr Gly Thr Val Glu Asn Thr Leu Phe Leu Thr Pro Ser Ser
            180                 185                 190

His Asp Asp Gly Ala Thr Leu Ile Cys Arg Ala Arg Ser Gln Ala Leu
        195                 200                 205

Pro Thr Gly Arg Asp Thr Ala Val Thr Leu Ser Leu Gln Tyr Pro Pro
    210                 215                 220

Met Val Thr Leu Ser Ala Glu Pro Gln Thr Val Gln Glu Gly Glu Lys
225                 230                 235                 240
```

```
Val Thr Phe Leu Cys Gln Ala Thr Ala Gln Pro Pro Val Thr Gly Tyr
            245                 250                 255

Arg Trp Ala Lys Gly Gly Ser Pro Val Leu Gly Ala Arg Gly Pro Arg
            260                 265                 270

Leu Glu Val Val Ala Asp Ala Thr Phe Leu Thr Glu Pro Val Ser Cys
            275                 280                 285

Glu Val Ser Asn Ala Val Gly Ser Ala Asn Arg Ser Thr Ala Leu Glu
            290                 295                 300

Val Leu Tyr Gly Pro Ile Leu Gln Ala Lys Pro Lys Ser Val Ser Val
305                 310                 315                 320

Asp Val Gly Lys Asp Ala Ser Phe Ser Cys Val Trp Arg Gly Asn Pro
                325                 330                 335

Leu Pro Arg Ile Thr Trp Thr Arg Met Gly Gly Ser Gln Val Leu Ser
            340                 345                 350

Ser Gly Pro Thr Leu Arg Leu Pro Ser Val Ala Leu Glu Asp Ala Gly
            355                 360                 365

Asp Tyr Val Cys Arg Ala Glu Pro Arg Arg Thr Gly Leu Gly Gly Gly
            370                 375                 380

Lys Ala Gln Ala Arg Leu Thr Val Asn Ala Pro Pro Val Val Thr Ala
385                 390                 395                 400

Leu Gln Pro Ala Pro Ala Phe Leu Arg Gly Pro Ala Arg Leu Gln Cys
            405                 410                 415

Val Val Phe Ala Ser Pro Ala Pro Asp Ser Val Val Trp Ser Trp Asp
            420                 425                 430

Glu Gly Phe Leu Glu Ala Gly Ser Leu Gly Arg Phe Leu Val Glu Ala
            435                 440                 445

Phe Pro Ala Pro Glu Val Glu Gly Gly Gln Gly Pro Gly Leu Ile Ser
            450                 455                 460

Val Leu His Ile Ser Gly Thr Gln Glu Ser Asp Phe Thr Thr Gly Phe
465                 470                 475                 480

Asn Cys Ser Ala Arg Asn Arg Leu Gly Glu Gly Arg Val Gln Ile His
            485                 490                 495

Leu Gly Arg Arg Asp Leu Leu Pro Thr Val Arg Ile Val Ala Gly Ala
            500                 505                 510

Ala Ser Ala Ala Thr Ser Leu Leu Met Val Ile Thr Gly Val Val Leu
            515                 520                 525

Cys Cys Trp Arg His Gly Ser Leu Ser Lys Gln Lys Asn Leu Val Arg
            530                 535                 540

Ile Pro Gly Ser Ser Glu Gly Ser Ser Arg Gly Pro Glu Glu Glu Glu
545                 550                 555                 560

Thr Gly Ser Ser Glu Asp Arg Gly Pro Ile Val His Thr Asp His Ser
                565                 570                 575

Asp Leu Val Leu Glu Glu Lys Glu Ala Leu Glu Thr Lys Asp Pro Thr
            580                 585                 590

Asn Gly Tyr Tyr Lys Val Arg Gly Val Ser Val Ser Leu Ser Leu Gly
            595                 600                 605

Glu Ala Pro Gly Gly Gly Leu Phe Leu Pro Pro Ser Pro Ile Gly
            610                 615                 620

Leu Pro Gly Thr Pro Thr Tyr Tyr Asp Phe Lys Pro His Leu Asp Leu
625                 630                 635                 640

Val Pro Pro Cys Arg Leu Tyr Arg Ala Arg Ala Gly Tyr Leu Thr Thr
            645                 650                 655
```

```
Pro His Pro Arg Ala Phe Thr Ser Tyr Met Lys Pro Thr Ser Phe Gly
            660                 665                 670

Pro Pro Asp Leu Ser Ser Gly Thr Pro Pro Phe Pro Tyr Ala Thr Leu
            675                 680                 685

Ser Pro Pro Ser His Gln Arg Leu Gln Thr His Val
            690                 695                 700

<210> SEQ ID NO 4
<211> LENGTH: 650
<212> TYPE: PRT
<213> ORGANISM: Mus musculus

<400> SEQUENCE: 4

Met Leu Ala Ser Ala Leu Leu Val Phe Leu Cys Cys Phe Lys Gly His
 1               5                  10                  15

Ala Gly Trp Ser Arg Tyr Trp Ile Ser Gly Asn Ser Ala Ser Gly Gln
            20                  25                  30

His Asp Leu His Ile Lys Pro Val Glu Leu Glu Asp Glu Ala Ser Tyr
         35                 40                  45

Glu Cys Gln Ala Ser Gln Ala Gly Leu Arg Ser Arg Pro Ala Gln Leu
 50                  55                  60

His Val Met Val Pro Glu Ala Pro Gln Val Leu Gly Gly Pro Ser
65                  70                  75                  80

Val Ser Leu Val Ala Gly Val Pro Gly Asn Leu Thr Cys Arg Ser Arg
                85                  90                  95

Gly Asp Ser Arg Pro Ala Pro Glu Leu Leu Trp Phe Arg Asp Gly Ile
            100                 105                 110

Arg Leu Asp Ala Ser Ser Phe His Gln Thr Thr Leu Lys Asp Lys Ala
        115                 120                 125

Thr Gly Thr Val Glu Asn Thr Leu Phe Leu Thr Pro Ser Ser His Asp
130                 135                 140

Asp Gly Ala Thr Leu Ile Cys Arg Ala Arg Ser Gln Ala Leu Pro Thr
145                 150                 155                 160

Gly Arg Asp Thr Ala Val Thr Leu Ser Leu Gln Tyr Pro Pro Met Val
                165                 170                 175

Thr Leu Ser Ala Glu Pro Gln Thr Val Gln Glu Gly Glu Lys Val Thr
            180                 185                 190

Phe Leu Cys Gln Ala Thr Ala Gln Pro Pro Val Thr Gly Tyr Arg Trp
        195                 200                 205

Ala Lys Gly Gly Ser Pro Val Leu Gly Ala Arg Gly Pro Arg Leu Glu
    210                 215                 220

Val Val Ala Asp Ala Thr Phe Leu Thr Glu Pro Val Ser Cys Glu Val
225                 230                 235                 240

Ser Asn Ala Val Gly Ser Ala Asn Arg Ser Thr Ala Leu Glu Val Leu
                245                 250                 255

Tyr Gly Pro Ile Leu Gln Ala Lys Pro Lys Ser Val Ser Val Asp Val
            260                 265                 270

Gly Lys Asp Ala Ser Phe Ser Cys Val Trp Arg Gly Asn Pro Leu Pro
        275                 280                 285

Arg Ile Thr Trp Thr Arg Met Gly Gly Ser Gln Val Leu Ser Ser Gly
    290                 295                 300

Pro Thr Leu Arg Leu Pro Ser Val Ala Leu Glu Asp Ala Gly Asp Tyr
305                 310                 315                 320

Val Cys Arg Ala Glu Pro Arg Thr Gly Leu Gly Gly Gly Lys Ala
                325                 330                 335
```

```
Gln Ala Arg Leu Thr Val Asn Ala Pro Pro Val Thr Ala Leu Gln
            340                 345                 350

Pro Ala Pro Ala Phe Leu Arg Gly Pro Ala Arg Leu Gln Cys Val Val
            355                 360                 365

Phe Ala Ser Pro Ala Pro Asp Ser Val Val Trp Ser Trp Asp Glu Gly
            370                 375                 380

Phe Leu Glu Ala Gly Ser Leu Gly Arg Phe Leu Val Glu Ala Phe Pro
385                 390                 395                 400

Ala Pro Glu Val Glu Gly Gly Gln Gly Pro Gly Leu Ile Ser Val Leu
                405                 410                 415

His Ile Ser Gly Thr Gln Glu Ser Asp Phe Thr Thr Gly Phe Asn Cys
                420                 425                 430

Ser Ala Arg Asn Arg Leu Gly Glu Gly Arg Val Gln Ile His Leu Gly
                435                 440                 445

Arg Arg Asp Leu Leu Pro Thr Val Arg Ile Val Ala Gly Ala Ala Ser
            450                 455                 460

Ala Ala Thr Ser Leu Leu Met Val Ile Thr Gly Val Val Leu Cys Cys
465                 470                 475                 480

Trp Arg His Gly Ser Leu Ser Lys Gln Lys Asn Leu Val Arg Ile Pro
                485                 490                 495

Gly Ser Ser Glu Gly Ser Ser Ser Arg Gly Pro Glu Glu Thr Gly
                500                 505                 510

Ser Ser Glu Asp Arg Gly Pro Ile Val His Thr Asp His Ser Asp Leu
            515                 520                 525

Val Leu Glu Glu Lys Glu Ala Leu Glu Thr Lys Asp Pro Thr Asn Gly
            530                 535                 540

Tyr Tyr Lys Val Arg Gly Val Ser Val Ser Leu Ser Leu Gly Glu Ala
545                 550                 555                 560

Pro Gly Gly Gly Leu Phe Leu Pro Pro Ser Pro Ile Gly Leu Pro
                565                 570                 575

Gly Thr Pro Thr Tyr Tyr Asp Phe Lys Pro His Gln Asp Leu Val Pro
            580                 585                 590

Pro Cys Arg Leu Tyr Arg Ala Arg Ala Gly Tyr Leu Thr Thr Pro His
            595                 600                 605

Pro Arg Ala Phe Thr Ser Tyr Met Lys Pro Thr Ser Phe Gly Pro Pro
            610                 615                 620

Asp Leu Ser Ser Gly Thr Pro Pro Phe Pro Tyr Ala Thr Leu Ser Pro
625                 630                 635                 640

Pro Ser His Gln Arg Leu Gln Thr His Val
                645                 650

<210> SEQ ID NO 5
<211> LENGTH: 2980
<212> TYPE: DNA
<213> ORGANISM: Homo sapiens

<400> SEQUENCE: 5
cccagagacc caggccgcgg aactggcagg cgtttcagag cgtcagaggc tgcggatgag    60
cagacttgga ggactccagg ccagagacta ggctgggcga agagtcgagc gtgaaggggg   120
ctccgggcca gggtgacagg aggcgtgctt gagaggaaga agttgacggg aaggccagtg   180
cgacggcaaa tctcgtgaac cttgggggac gaatgctcag gatgcgggtc ccgccctcc   240 tcgtcctcct cttctgcttc agagggagag caggcccgtc gccccatttc ctgcaacagc   300
```

```
cagaggacct ggtggtgctg ctggggagg aagcccggct gccgtgtgct ctgggcgcct    360
actgggggct agttcagtgg actaagagtg ggctggccct aggggccaa agggacctac    420 cagggtggtc ccggtactgg atatcaggga atgcagccaa tggccagcat gacctccaca    480
ttaggcccgt ggagctagag gatgaagcat catatgaatg tcaggctaca caagcaggcc    540
tccgctccag accagcccaa ctgcacgtgc tggtccccc agaagccccc caggtgctgg    600
gcggcccctc tgtgtctctg gttgctggag ttcctgcgaa cctgacatgt cggagccgtg    660
gggatgcccg ccctacccct gaattgctgt ggttccgaga tggggtcctg ttggatggag    720
ccaccttcca tcagacctg ctgaaggaag ggacccctgg gtcagtggag agcaccttaa    780
ccctgacccc tttcagccat gatgatggag ccacctttgt ctgccgggcc cggagccagg    840
ccctgcccac aggaagagac acagctatca cactgagcct gcagtacccc ccagaggtga    900
ctctgtctgc ttcgccacac actgtgcagg agggagagaa ggtcattttc ctgtgccagg    960
ccacagccca gcctcctgtc acaggctaca ggtgggcaaa agggggctct ccggtgctcg   1020 ggcccgcgg gccaaggtta gaggtcgtgg cagacgcctc gttcctgact gagcccgtgt   1080
cctgcgaggt cagcaacgcc gtgggtagcg ccaaccgcag tactgcgctg gatgtgctgt   1140
ttgggccgat tctgcaggca aagccggagc ccgtgtccgt ggacgtgggg gaagacgctt   1200
ccttcagctg cgcctggcgc gggaacccgc ttccacgggt aacctggacc cgccgcggtg   1260
gcgcgcaggt gctgggctct ggagccacac tgcgtcttcc gtcggtgggg cccgaggacg   1320
caggcgacta tgtgtgcaga gctgaggctg ggctatcggg cctgcgggc ggcgccgcgg   1380 aggctcggct gactgtgaac gctcccccag tagtgaccgc cctgcactct gcgcctgcct   1440
tcctgagggg ccctgctcgc ctccagtgtc tggttttcgc ctctcccgcc cagatgccg    1500 tggtctggtc ttgggatgag ggcttcctgg aggcggggtc gcagggccgg ttcctggtgg   1560
agacattccc tgccccagag agccgcgggg gactgggtcc gggcctgatc tctgtgctac   1620
acatttcggg gacccaggag tctgacttta gcaggagctt taactgcagt gcccggaacc   1680
ggctgggcga gggaggtgcc caggccagcc tgggccgtag agacttgctg cccactgtgc   1740
ggatagtggc cggagtggcc gctgccacca caactctcct tatggtcatc actggggtgg   1800
ccctctgctg ctggcgccac agcaaggcct cagcctcttt ctccgagcaa aagaacctga   1860
tgcgaatccc tggcagcagc gacggctcca gttcacgagg tcctgaagaa gaggagacag   1920
gcagccgcga ggaccggggc cccattgtgc acactgacca cagtgatctg gttctggagg   1980
agaaagggac tctggagacc aaggacccaa ccaacgttta ctacaaggtc cgaggagtca   2040
gtgtgagcct gagccttggc gaagcccctg gaggaggtct cttcctgcca ccaccctccc   2100
cccttgggcc cccagggacc cctaccttct atgacttcaa cccacacctg gcatggtcc    2160 ccccctgcag actttacaga gccagggcag gctatctcac cacaccccac cctcgagctt   2220
tcaccagcta catcaaaccc acatcctttg gccccagga tctggccccc gggactcccc   2280
ccttcccata tgctgccttc cccacaccta gccacccgcg tctccagact cacgtgtgac   2340
atctttccaa tggaagagtc ctgggatctc caacttgcca taatggattg ttctgatttc   2400
tgaggcgcca ggacaagttg gcgaccttac tcctccaaaa ctgaacacaa ggggagggaa   2460
agatcattac atttgtcagg agcatttgta tacagtcagc tcagccaaag gagatgcccc   2520
aagtgggagc aacatggcca cccaatatgc ccacctattc cccggtgtaa aagagattca   2580
agatggcagg taggcccttt gaggagagat ggggacaggg cagtgggtgt tgggagtttg   2640
gggccgggat ggaagttgtt tctagccact gaaagaagat atttcaagat gaccatctgc   2700
```

-continued

```
attgagagga aaggtagcat aggatagatg aagatgaaga gcataccagg ccccaccctg    2760
gctctccctg aggggaactt tgctcggcca atggaaatgc agccaagatg gccatatact    2820
ccctaggaac ccaagatggc caccatcttg attttacttt ccttaaagac tcagaaagac    2880
ttggacccaa ggagtgggga tacagtgaga attaccactg ttggggcaaa atattgggat    2940
aaaaatattt atgtttaata ataaaaaaaa gtcaaagagg                          2980
```

```
<210> SEQ ID NO 6
<211> LENGTH: 708
<212> TYPE: PRT
<213> ORGANISM: Homo sapiens

<400> SEQUENCE: 6
```

| | | | | | | | | | | | | | | |
|---|---|---|---|---|---|---|---|---|---|---|---|---|---|---|
| Met | Leu | Arg | Met | Arg | Val | Pro | Ala | Leu | Leu | Val | Leu | Leu | Phe | Cys | Phe |
| 1 | | | | 5 | | | | | 10 | | | | | 15 | |

Arg Gly Arg Ala Gly Pro Ser Pro His Phe Leu Gln Gln Pro Glu Asp
                20                  25                  30

Leu Val Val Leu Gly Glu Glu Ala Arg Leu Pro Cys Ala Leu Gly
            35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240

Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
        275                 280                 285

Val Ser Cys Glu Val Ser Asn Ala Val Gly Ser Ala Asn Arg Ser Thr
    290                 295                 300

Ala Leu Asp Val Leu Phe Gly Pro Ile Leu Gln Ala Lys Pro Glu Pro
305                 310                 315                 320

```
Val Ser Val Asp Val Gly Glu Asp Ala Ser Phe Ser Cys Ala Trp Arg
            325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
            355                 360                 365

Asp Ala Gly Asp Tyr Val Cys Arg Ala Glu Ala Gly Leu Ser Gly Leu
        370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
            405                 410                 415

Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
            450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
            485                 490                 495

Gln Ala Ser Leu Gly Arg Arg Asp Leu Leu Pro Thr Val Arg Ile Val
            500                 505                 510

Ala Gly Val Ala Ala Ala Thr Thr Thr Leu Leu Met Val Ile Thr Gly
            515                 520                 525

Val Ala Leu Cys Cys Trp Arg His Ser Lys Ala Ser Ala Ser Phe Ser
            530                 535                 540

Glu Gln Lys Asn Leu Met Arg Ile Pro Gly Ser Ser Asp Gly Ser Ser
545                 550                 555                 560

Ser Arg Gly Pro Glu Glu Glu Thr Gly Ser Arg Glu Asp Arg Gly
            565                 570                 575

Pro Ile Val His Thr Asp His Ser Asp Leu Val Leu Glu Glu Lys Gly
            580                 585                 590

Thr Leu Glu Thr Lys Asp Pro Thr Asn Gly Tyr Tyr Lys Val Arg Gly
            595                 600                 605

Val Ser Val Ser Leu Ser Leu Gly Glu Ala Pro Gly Gly Gly Leu Phe
            610                 615                 620

Leu Pro Pro Pro Ser Pro Leu Gly Pro Pro Gly Thr Pro Thr Phe Tyr
625                 630                 635                 640

Asp Phe Asn Pro His Leu Gly Met Val Pro Pro Cys Arg Leu Tyr Arg
            645                 650                 655

Ala Arg Ala Gly Tyr Leu Thr Thr Pro His Pro Arg Ala Phe Thr Ser
            660                 665                 670

Tyr Ile Lys Pro Thr Ser Phe Gly Pro Pro Asp Leu Ala Pro Gly Thr
        675                 680                 685

Pro Pro Phe Pro Tyr Ala Ala Phe Pro Thr Pro Ser His Pro Arg Leu
            690                 695                 700

Gln Thr His Val
705

<210> SEQ ID NO 7
<211> LENGTH: 2976
<212> TYPE: DNA
```

<213> ORGANISM: Homo sapiens

<400> SEQUENCE: 7

```
gggaactggc aggcgtttca gagcgtcaga ggctgcggat gagcagactt ggaggactcc    60
aggccagaga ctaggctggg cgaagagtcg agcgtgaagg gggctccggg ccagggtgac   120
aggaggcgtg cttgagagga agaagttgac gggaaggcca gtgcgacggc aaatctcgtg   180
aaccttgggg gacgaatgct caggatgcgg gtccccgccc tcctcgtcct cctcttctgc   240
ttcagaggga gagcaggccc gtcgccccat ttcctgcaac agccagagga cctggtggtg   300
ctgctggggg aggaagcccg gctgccgtgt gctctgggcg cctactgggg gctagttcag   360
tggactaaga gtgggctggc cctagggggc caaagggacc taccagggtg gtcccggtac   420
tggatatcag ggaatgcagc caatggccag catgacctcc acattaggcc cgtggagcta   480
gaggatgaag catcatatga atgtcaggct acacaagcag gcctccgctc cagaccagcc   540
caactgcacg tgctggtccc cccagaagcc cccaggtgc tgggcggccc ctctgtgtct   600
ctggttgctg gagttcctgc gaacctgaca tgtcggagcc gtggggatgc ccgccctgcc   660
cctgaattgc tgtggttccg agatgggtc ctgttggatg gagccacctt ccatcagacc   720
ctgctgaagg aagggacccc tgggtcagtg gagagcacct taaccctgac cccctttcag   780
ccatgatgat ggagccacct ttgtctgccg ggcccggagc caggccctgc ccacaggaag   840
agacacagct atcacactga gcctgcagta cccccccagag gtgactctgt ctgcttcgcc   900
acacactgtg caggagggag agaaggtcat tttcctgtgc caggccacag cccagcctcc   960
tgtcacaggc tacaggtggg caaaaggggg ctctccggtg ctcggggccc gcgggccaag  1020
gttagaggtc gtggcagacg cctcgttcct gactgagccc gtgtcctgcg aggtcagcaa  1080
cgccgtgggt agcgccaacc gcagtactgc gctggatgtg ctgtttgggc cgattctgca  1140
ggcaaagccg gagcccgtgt ccgtggacgt ggggggaagac gcttccttca gctgcgcctg  1200
gcgcgggaac ccgcttccac gggtaacctg gacccgccgc ggtggcgcgc aggtgctggg  1260
ctctggagcc acactgcgtc ttccgtcggt ggggcccgag gacgcaggcg actatgtgtg  1320
cagagctgag gctgggctat cgggcctgcg gggcggcgcc gcggaggctc ggctgactgt  1380
gaacgctccc ccagtagtga ccgccctgca ctctgcgcct gccttcctga ggggccctgc  1440
tcgcctccag tgtctggttt tcgcctctcc cgccccagat gccgtggtct ggtcttggga  1500
tgagggcttc ctggaggcgg ggtcgcaggg ccggttcctg gtggagacat tccctgcccc  1560
agagagccgc gggggactgg gtccgggcct gatctctgtg ctacacattt cggggaccca  1620
ggagtctgac tttagcagga gctttaactg cagtgcccgg aaccggctgg gcgagggagg  1680
tgcccaggcc agcctgggcc gtagagactt gctgcccact gtgcggatag tggccggagt  1740
ggccgctgcc accacaactc tccttatggt catcactggg gtggccctct gctgctggcg  1800
ccacagcaag gcctcagcct ctttctccga gcaaaagaac ctgatgcgaa tccctggcag  1860
cagcgacggc tccagttcac gaggtcctga agaagaggag acaggcagcc gcgaggaccg  1920
gggcccatt gtgcacactg accacagtga tctggttctg gaggaggaag ggactctgga  1980
gaccaaggac ccaaccaacg gttactacaa ggtccgagga gtcagtgtga gcctgagcct  2040
tggcgaagcc cctggaggag gtctcttcct gccaccaccc tcccccctg ggcccccagg  2100
gaccctacc ttctatgact tcaacccaca cctgggcatg gtccccccct gcagacttta  2160
cagagccagg gcaggctatc tcaccacacc ccacccctcga gctttcacca gctacatcaa  2220
acccacatcc tttgggcccc cagatctggc ccccgggact cccccccttcc catatgctgc  2280
```

-continued

```
cttccccaca cctagccacc cgcgtctcca gactcacgtg tgacatcttt ccaatggaag    2340
agtcctggga tctccaactt gccatcctgg attgttctga tttctgagga gccaggacaa    2400
gttggcgacc ttactcctcc aaaactgaac acaaggggag ggaaagatca ttacatttgt    2460
caggagcatt tgtatacagt cagctcagcc aaaggagatg ccccaagtgg gagcaacatg    2520
gccacccaat atgcccacct attccccggt gtaaaagaga ttcaagatgg caggtaggcc    2580
ctttgaggag agatggggac agggcagtgg gtgttgggag tttggggccg ggatggaagt    2640
tgtttctagc cactgaaaga agatatttca agatgaccat ctgcattgag aggaaaggta    2700
gcataggata gatgaagatg aagagcatac caggccccac cctggctctc cctgagggga    2760
actttgctcg gccaatggaa atgcagccaa gatggcccta tactccctag gaacccaaga    2820
tggccaccat cttgatttta ctttccttaa agacacagaa agacttggac ccaaggagtg    2880
gggatacagt gagaattacc actgttgggg caaatattg ggataaaaat atttatgttt    2940
aataataaaa aaaagtcaaa aaaaaaaaaa aaaaaa                              2976
```

<210> SEQ ID NO 8
<211> LENGTH: 196
<212> TYPE: PRT
<213> ORGANISM: Homo sapiens

<400> SEQUENCE: 8

```
Met Leu Arg Met Arg Val Pro Ala Leu Leu Val Leu Leu Phe Cys Phe
 1               5                  10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Ala Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Gln Pro
        195
```

<210> SEQ ID NO 9
<211> LENGTH: 1532
<212> TYPE: DNA
<213> ORGANISM: Homo sapiens

<400> SEQUENCE: 9

```
cccagagacc caggccgcgg aactggcagg cgtttcagag cgtcagaggc tgcggatgag      60
cagacttgga ggactccagg ccagagacta ggctgggcga agagtcgagc gtgaaggggg     120
ctccgggcca gggtgacagg aggcgtgctt gagaggaaga agttgacggg aaggccagtg     180
cgacggcaaa tctcgtgaac cttggggggac gaatgctcag gatgcgggtc ccgccctcc     240
tcgtcctcct cttctgcttc agagggagag caggcccgtc gccccatttc tgcaacagc     300
cagaggacct ggtggtgctg ctgggcgagg gaggtgccca ggccagcctg ggccgtagag     360
cctcagcctc tttctccgag caaaagaacc tgatgcgaat ccctggcagc agcgacggct     420
ccagttcacg aggtcctgaa gaagaggaga caggcagccg cgaggaccgg ggccccattg     480
tgcacactga ccacagtgat ctggttctgg aggaggaagg gactctggag accaaggacc     540
caaccaacgg ttactacaag gtccgaggag tcagtgtgag cctgagcctt ggcgaagccc     600
ctggaggagg tctcttcctg ccaccaccct ccccccttgg gccccaggg accctacct     660
tctatgactt caacccacac ctgggcatgg tccccccctg cagactttac agagccaggg     720
caggctctct caccacaccc caccctcgag cttcaccag ctacatcaaa cccacatcct     780
ttgggccccc agatctggcc cccgggactc cccccttccc atatgctgcc ttccccacac     840
ctagccaccc gcgtctccag actcacgtgt gacatctttc caatggaaga gtcctgggat     900
ctccaacttg ccataatgga ttgttctgat ttctgaggag ccaggacaag ttggcgacct     960
tactcctcca aaactgaaca caaggggagg gaaagatcat tacatttgtc aggagcattt    1020
gtatacagtc agctcagcca aaggagatgc cccaagtggg agcaacatgg ccacccaata    1080
tgcccaccta ttccccggtg taaaagagat tcaagatggc aggtaggccc tttgaggaga    1140
gatgggggaca gggcagtggg tgttggggagt ttggggccgg gatggaagtt gtttctagcc    1200
actgaaagaa gatatttcaa gatgaccatc tgcattgaga ggaaaggtag cataggatag    1260
atgaagatga agagcatacc aggccccacc ctggctctcc ctgaggggaa ctttgctcgg    1320
ccaatggaaa tgcagccaag atggccatat actccctagg aacccaagat ggccaccatc    1380
ttgattttac tttccttaaa gactcagaaa gacttggacc caaggagtgg ggatacagtg    1440
agaattacca ctgttggggc aaaatattgg gataaaaata tttatgttta ataataaaaa    1500
aaagtcaaag aggcaaaaaa aaaaaaaaaa aa                                  1532
```

<210> SEQ ID NO 10
<211> LENGTH: 219
<212> TYPE: PRT
<213> ORGANISM: Homo sapiens

<400> SEQUENCE: 10

```
Met Leu Arg Met Arg Val Pro Ala Leu Leu Val Leu Leu Phe Cys Phe
 1               5                  10                  15

Arg Gly Arg Ala Gly Pro Ser Pro His Phe Leu Gln Gln Pro Glu Asp
                20                  25                  30

Leu Val Val Leu Leu Gly Glu Gly Gly Ala Gln Ala Ser Leu Gly Arg
            35                  40                  45

Arg Ala Ser Ala Ser Phe Ser Glu Gln Lys Asn Leu Met Arg Ile Pro
        50                  55                  60

Gly Ser Ser Asp Gly Ser Ser Arg Gly Pro Glu Glu Glu Glu Thr
 65                  70                  75                  80

Gly Ser Arg Glu Asp Arg Gly Pro Ile Val His Thr Asp His Ser Asp
                85                  90                  95
```

```
Leu Val Leu Glu Glu Gly Thr Leu Glu Thr Lys Asp Pro Thr Asn
            100                 105                 110

Gly Tyr Tyr Lys Val Arg Gly Val Ser Val Ser Leu Ser Leu Gly Glu
        115                 120                 125

Ala Pro Gly Gly Gly Leu Phe Leu Pro Pro Ser Pro Leu Gly Pro
    130                 135                 140

Pro Gly Thr Pro Thr Phe Tyr Asp Phe Asn Pro His Leu Gly Met Val
145                 150                 155                 160

Pro Pro Cys Arg Leu Tyr Arg Ala Arg Ala Gly Tyr Leu Thr Thr Pro
            165                 170                 175

His Pro Arg Ala Phe Thr Ser Tyr Ile Lys Pro Thr Ser Phe Gly Pro
            180                 185                 190

Pro Asp Leu Ala Pro Gly Thr Pro Pro Phe Pro Tyr Ala Ala Phe Pro
            195                 200                 205

Thr Pro Ser His Pro Arg Leu Gln Thr His Val
        210                 215
```

<210> SEQ ID NO 11
<211> LENGTH: 26
<212> TYPE: DNA
<213> ORGANISM: Artificial Sequence
<220> FEATURE:
<223> OTHER INFORMATION: Adapter for cDNA amplification

<400> SEQUENCE: 11
cagctccaca acctacatca ttccgt                                      26

<210> SEQ ID NO 12
<211> LENGTH: 12
<212> TYPE: DNA
<213> ORGANISM: Artificial Sequence
<220> FEATURE:
<223> OTHER INFORMATION: Adapter for cDNA amplification

<400> SEQUENCE: 12
acggaatgat gt                                                     12

<210> SEQ ID NO 13
<211> LENGTH: 26
<212> TYPE: DNA
<213> ORGANISM: Artificial Sequence
<220> FEATURE:
<223> OTHER INFORMATION: Adapter for cDNA amplification

<400> SEQUENCE: 13
gtccatcttc tctctgagac tctggt                                      26

<210> SEQ ID NO 14
<211> LENGTH: 12
<212> TYPE: DNA
<213> ORGANISM: Artificial Sequence
<220> FEATURE:
<223> OTHER INFORMATION: Adapter for cDNA amplification

<400> SEQUENCE: 14
accagagtct ca                                                     12

<210> SEQ ID NO 15
<211> LENGTH: 26
<212> TYPE: DNA
<213> ORGANISM: Artificial Sequence
<220> FEATURE:
<223> OTHER INFORMATION: Adapter for cDNA amplification

```
<400> SEQUENCE: 15
ctgatgggtg tcttctgtga gtgtgt                                        26

<210> SEQ ID NO 16
<211> LENGTH: 12
<212> TYPE: DNA
<213> ORGANISM: Artificial Sequence
<220> FEATURE:
<223> OTHER INFORMATION: Adapter for cDNA amplification

<400> SEQUENCE: 16
acacactcac ag                                                       12

<210> SEQ ID NO 17
<211> LENGTH: 26
<212> TYPE: DNA
<213> ORGANISM: Artificial Sequence
<220> FEATURE:
<223> OTHER INFORMATION: Adapter for cDNA amplification

<400> SEQUENCE: 17
ccagcatcga gaatcagtgt gacagt                                        26

<210> SEQ ID NO 18
<211> LENGTH: 12
<212> TYPE: DNA
<213> ORGANISM: Artificial Sequence
<220> FEATURE:
<223> OTHER INFORMATION: Adapter for cDNA amplification

<400> SEQUENCE: 18
actgtcacac tg                                                       12

<210> SEQ ID NO 19
<211> LENGTH: 26
<212> TYPE: DNA
<213> ORGANISM: Artificial Sequence
<220> FEATURE:
<223> OTHER INFORMATION: Adapter for cDNA amplification

<400> SEQUENCE: 19
gtcgatgaac ttcgactgtc gatcgt                                        26

<210> SEQ ID NO 20
<211> LENGTH: 12
<212> TYPE: DNA
<213> ORGANISM: Artificial Sequence
<220> FEATURE:
<223> OTHER INFORMATION: Adapter for cDNA amplification

<400> SEQUENCE: 20
acgatcgaca gt                                                       12

<210> SEQ ID NO 21
<211> LENGTH: 26
<212> TYPE: DNA
<213> ORGANISM: Artificial Sequence
<220> FEATURE:
<223> OTHER INFORMATION: Primer for RACE method

<400> SEQUENCE: 21
ggctttacac tttatgcttc cggctc                                        26

<210> SEQ ID NO 22
```

<211> LENGTH: 26
<212> TYPE: DNA
<213> ORGANISM: Artificial Sequence
<220> FEATURE:
<223> OTHER INFORMATION: Primer for RACE method

<400> SEQUENCE: 22
cagctatgac catgattacg ccaagc                                           26

<210> SEQ ID NO 23
<211> LENGTH: 26
<212> TYPE: DNA
<213> ORGANISM: Artificial Sequence
<220> FEATURE:
<223> OTHER INFORMATION: Primer for RACE method

<400> SEQUENCE: 23
aggcgattaa gttgggtaac gccagg                                           26

<210> SEQ ID NO 24
<211> LENGTH: 26
<212> TYPE: DNA
<213> ORGANISM: Artificial Sequence
<220> FEATURE:
<223> OTHER INFORMATION: Primer for RACE method

<400> SEQUENCE: 24
ccagtcacga cgttgtaaaa cgacgg                                           26

<210> SEQ ID NO 25
<211> LENGTH: 26
<212> TYPE: DNA
<213> ORGANISM: Artificial Sequence
<220> FEATURE:
<223> OTHER INFORMATION: Primer for RACE method

<400> SEQUENCE: 25
cttcccgtat gctaccttgt ctccac                                           26

<210> SEQ ID NO 26
<211> LENGTH: 26
<212> TYPE: DNA
<213> ORGANISM: Artificial Sequence
<220> FEATURE:
<223> OTHER INFORMATION: Primer for RACE method

<400> SEQUENCE: 26
tccatctctc caagtgaagg gtcttg                                           26

<210> SEQ ID NO 27
<211> LENGTH: 26
<212> TYPE: DNA
<213> ORGANISM: Artificial Sequence
<220> FEATURE:
<223> OTHER INFORMATION: Primer for RACE method

<400> SEQUENCE: 27
ccaacagtcc tgcatgcttg taatga                                           26

<210> SEQ ID NO 28
<211> LENGTH: 26
<212> TYPE: DNA
<213> ORGANISM: Artificial Sequence
<220> FEATURE:
<223> OTHER INFORMATION: Primer for RACE method -continued

```
<400> SEQUENCE: 28
tccttcaatg ttcagttttg gagggg                                        26
```